US012589083B2

(12) United States Patent
Moe et al.

(10) Patent No.: US 12,589,083 B2
(45) Date of Patent: Mar. 31, 2026

(54) ABUSE-DETERRENT DOSAGE FORMS CONTAINING ESKETAMINE

(71) Applicant: Clexio Biosciences Ltd., Jerusalem (IL)

(72) Inventors: Derek Moe, Mound, MN (US); Randal Seburg, Louisville, KY (US); Sagar Rane, Bellevue, WA (US)

(73) Assignee: CLEXIO BIOSCIENCES LTD., Yokne'am (IL)

(*) Notice: Subject to any disclaimer, the term of this patent is extended or adjusted under 35 U.S.C. 154(b) by 1177 days.

(21) Appl. No.: 17/523,193

(22) Filed: Nov. 10, 2021

(65) Prior Publication Data

US 2022/0062200 A1 Mar. 3, 2022

Related U.S. Application Data

(62) Division of application No. 16/869,309, filed on May 7, 2020, now Pat. No. 11,324,707.

(60) Provisional application No. 62/844,286, filed on May 7, 2019.

(51) Int. Cl.

| | |
|---|---|
| ***A61K 31/135*** | (2006.01) |
| ***A61K 9/20*** | (2006.01) |
| ***G01N 30/02*** | (2006.01) |

(52) U.S. Cl.

CPC .......... *A61K 31/135* (2013.01); *A61K 9/2009* (2013.01); *A61K 9/2013* (2013.01); *A61K 9/2018* (2013.01); *A61K 9/2027* (2013.01); *A61K 9/2054* (2013.01); *G01N 2030/027* (2013.01)

(58) Field of Classification Search

CPC ........ A61K 31/135; A61K 33/10; A61P 25/24
See application file for complete search history.

(56) References Cited

U.S. PATENT DOCUMENTS

| | | | |
|---|---|---|---|
| 2,798,053 | A | 7/1957 | Brown |
| 2,909,462 | A | 10/1959 | Warfield et al. |
| 5,169,645 | A | 12/1992 | Shukla et al. |
| 5,248,669 | A | 9/1993 | Amer |
| 5,472,712 | A | 12/1995 | Oshlack et al. |
| 5,500,227 | A | 3/1996 | Oshlack et al. |
| 5,958,459 | A | 9/1999 | Chasin et al. |
| 5,965,161 | A | 10/1999 | Oshlack et al. |
| 5,968,551 | A | 10/1999 | Oshlack et al. |
| 6,024,981 | A | 2/2000 | Khankari et al. |
| 6,033,686 | A | 3/2000 | Seth |
| 6,103,261 | A | 8/2000 | Chasin et al. |
| 6,129,933 | A | 10/2000 | Oshlack et al. |
| 6,143,353 | A | 11/2000 | Oshlack et al. |
| 6,159,501 | A | 12/2000 | Skinhoj |
| 6,245,351 | B1 | 6/2001 | Nara et al. |
| 6,251,430 | B1 | 6/2001 | Zhang et al. |
| 6,261,599 | B1 | 7/2001 | Oshlack et al. |
| 6,290,990 | B1 | 9/2001 | Grabowski et al. |
| 6,294,195 | B1 | 9/2001 | Oshlack et al. |
| 6,309,668 | B1 | 10/2001 | Bastin et al. |
| 6,316,031 | B1 | 11/2001 | Oshlack et al. |
| 6,335,033 | B2 | 1/2002 | Oshlack et al. |
| 6,375,987 | B1 | 4/2002 | Farah et al. |
| 6,387,404 | B2 | 5/2002 | Oshlack et al. |
| 6,399,096 | B1 | 6/2002 | Miller et al. |
| 6,419,954 | B1 | 7/2002 | Chu et al. |
| 6,500,459 | B1 | 12/2002 | Chhabra et al. |
| 6,534,091 | B1 | 3/2003 | Garces et al. |
| 6,572,885 | B2 | 6/2003 | Oshlack et al. |
| 6,680,071 | B1 | 1/2004 | Johnson et al. |
| 6,685,964 | B1 | 2/2004 | Bartholomaeus et al. |
| 6,699,502 | B1 | 3/2004 | Fanara et al. |
| 6,706,281 | B2 | 3/2004 | Oshlack et al. |
| 6,708,822 | B1 | 3/2004 | Muni |
| 6,730,321 | B2 | 5/2004 | Ting et al. |
| 6,730,325 | B2 | 5/2004 | Devane et al. |
| 6,733,783 | B2 | 5/2004 | Oshlack et al. |
| 6,733,790 | B1 | 5/2004 | Garces Garces |
| 6,743,442 | B2 | 6/2004 | Oshlack et al. |
| 6,753,014 | B1 | 6/2004 | Sjoeblom |
| 6,759,059 | B1 | 7/2004 | Pettersson et al. |

(Continued)

FOREIGN PATENT DOCUMENTS

| | | |
|---|---|---|
| EP | 1103256 A1 | 5/2001 |
| EP | 1419766 A1 | 5/2004 |

(Continued)

OTHER PUBLICATIONS

Co-pending U.S. Appl. No. 17/523,193, filed Nov. 10, 2021.
Drug Discovery Trends Editor (DDT Editor) (Drug Discovery and Development, Testing Drug Stability for Long-Term Storage, Oct. 2012) (Year: 2012).
ICH Harmonised Tripartite Guideline (ICH) (International Conference on Harmonisation of Technical Requirements for Registration of Pharmaceuticals for Human Use, Feb. 2003, pp. 1-18) (Year: 2003).
Loh et al (Asian Journal of Pharmaceutical Sciences, 2015, vol. 10, pp. 255-27 4) (Year: 2015).

(Continued)

*Primary Examiner* — Mark V Stevens
(74) *Attorney, Agent, or Firm* — BakerHostetler

(57) ABSTRACT

Disclosed herein are immediate release oral dosage forms that contain abuse-deterrent and abuse-resistant features. In particular, the disclosed dosage forms can provide deterrence of abuse by ingestion of multiple individual doses. The disclosed dosage forms can likewise provide protection from overdose in the event of accidental or intentional ingestion of multiple individual doses. The dosage forms may also exhibit abuse resistant properties when physically manipulated, and also when physically manipulated and then administered in a manner not consistent with oral dosing. The dosage forms may also exhibit abuse resistant properties when administered in a manner intended to result in administration of the esketamine in a higher than therapeutic dose.

11 Claims, 5 Drawing Sheets

(56) References Cited

U.S. PATENT DOCUMENTS

| | | | | |
|---|---|---|---|---|
| 6,780,504 | B2 | 8/2004 | Rupprecht et al. | |
| 6,793,936 | B2 | 9/2004 | Devane et al. | |
| 6,855,735 | B2 | 2/2005 | Friedman | |
| 6,863,901 | B2 | 3/2005 | Hirsh et al. | |
| 6,902,742 | B2 | 6/2005 | Devane et al. | |
| 6,905,709 | B2 | 6/2005 | Oshlack et al. | |
| 7,022,313 | B2 | 4/2006 | O'Connor et al. | |
| 7,090,867 | B2 | 8/2006 | Odidi et al. | |
| 7,375,083 | B2 | 5/2008 | Mickle et al. | |
| 7,387,792 | B2 | 6/2008 | Hirsh et al. | |
| 7,399,488 | B2 | 7/2008 | Hirsh et al. | |
| 7,514,100 | B2 | 4/2009 | Oshlack et al. | |
| 7,658,939 | B2 | 2/2010 | Oshlack et al. | |
| 7,682,633 | B2 | 3/2010 | Matthews et al. | |
| 7,776,314 | B2 | 8/2010 | Bartholomaeus et al. | |
| 8,187,636 | B2 | 5/2012 | Soscia et al. | |
| 8,309,060 | B2 | 11/2012 | Bartholomaus et al. | |
| 8,349,362 | B2 | 1/2013 | Soscia et al. | |
| 8,445,018 | B2 | 5/2013 | Habib et al. | |
| 8,465,776 | B2 | 6/2013 | Hoarau | |
| 8,603,525 | B2 | 12/2013 | Oury et al. | |
| 8,637,540 | B2 | 1/2014 | Kumar et al. | |
| 8,647,669 | B2 | 2/2014 | Soscia et al. | |
| 9,707,224 | B2 | 7/2017 | Haswani et al. | |
| 9,757,371 | B2 | 9/2017 | Haswani et al. | |
| 9,827,204 | B2 | 11/2017 | Haswani et al. | |
| 9,913,803 | B2 | 3/2018 | Nivorozhkin et al. | |
| 10,034,832 | B2 | 7/2018 | Salce et al. | |
| 10,172,810 | B2 | 1/2019 | Mccarty | |
| 10,201,505 | B2 | 2/2019 | Haswani et al. | |
| 10,252,982 | B2 | 4/2019 | Nivorozhkin et al. | |
| 10,335,379 | B2 | 7/2019 | Manthei et al. | |
| 10,441,544 | B2 | 10/2019 | Glue et al. | |
| 10,568,881 | B2 | 2/2020 | Haswani et al. | |
| 10,888,528 | B2 * | 1/2021 | Haswani | A61K 31/165 |
| 11,207,318 | B2 | 12/2021 | Haswani et al. | |
| 11,324,707 | B2 | 5/2022 | Moe et al. | |
| 11,534,409 | B2 * | 12/2022 | Haswani | A61K 31/00 |
| 11,730,702 | B2 * | 8/2023 | Haswani | A61K 47/58 424/490 |
| 12,268,658 | B2 * | 4/2025 | Schumann | A61K 31/135 |
| 2002/0006919 | A1 | 1/2002 | Thosar et al. | |
| 2002/0044966 | A1 | 4/2002 | Bartholomaeus et al. | |
| 2002/0110595 | A1 | 8/2002 | Chang et al. | |
| 2003/0065002 | A1 | 4/2003 | Caruso et al. | |
| 2003/0068375 | A1 | 4/2003 | Wright et al. | |
| 2003/0077297 | A1 | 4/2003 | Chen et al. | |
| 2003/0125347 | A1 | 7/2003 | Anderson et al. | |
| 2003/0180362 | A1 | 9/2003 | Park et al. | |
| 2003/0190358 | A1 | 10/2003 | Oshlack et al. | |
| 2004/0009219 | A1 | 1/2004 | Odidi et al. | |
| 2004/0028735 | A1 | 2/2004 | Kositprapa | |
| 2004/0052844 | A1 | 3/2004 | Hsiao et al. | |
| 2004/0092531 | A1 | 5/2004 | Chizh et al. | |
| 2004/0096499 | A1 | 5/2004 | Vaya et al. | |
| 2004/0096500 | A1 | 5/2004 | Oshlack et al. | |
| 2004/0105887 | A1 | 6/2004 | Oshlack et al. | |
| 2004/0121001 | A1 | 6/2004 | Oshlack et al. | |
| 2004/0131552 | A1 | 7/2004 | Boehm | |
| 2004/0170680 | A1 | 9/2004 | Oshlack et al. | |
| 2004/0185098 | A1 | 9/2004 | Oshlack et al. | |
| 2004/0253310 | A1 | 12/2004 | Fischer et al. | |
| 2005/0020613 | A1 | 1/2005 | Boehm et al. | |
| 2005/0074493 | A1 | 4/2005 | Mehta et al. | |
| 2005/0089568 | A1 | 4/2005 | Oshlack et al. | |
| 2005/0106249 | A1 | 5/2005 | Hwang et al. | |
| 2005/0163856 | A1 | 7/2005 | Maloney et al. | |
| 2005/0165038 | A1 | 7/2005 | Gordon | |
| 2005/0245483 | A1 | 11/2005 | Brogmann et al. | |
| 2006/0024361 | A1 | 2/2006 | Odidi et al. | |
| 2006/0104909 | A1 | 5/2006 | Vaghefi et al. | |
| 2006/0251721 | A1 | 11/2006 | Cruz et al. | |
| 2007/0009589 | A1 | 1/2007 | Raghupathi et al. | |
| 2007/0203165 | A1 | 8/2007 | Shafer et al. | |
| 2008/0069891 | A1 | 3/2008 | Habib et al. | |
| 2008/0311205 | A1 | 12/2008 | Habib et al. | |
| 2009/0022798 | A1 | 1/2009 | Rosenberg et al. | |
| 2009/0202634 | A1 | 8/2009 | Jans et al. | |
| 2009/0238868 | A1 | 9/2009 | Mehta | |
| 2009/0297617 | A1 | 12/2009 | Rariy et al. | |
| 2009/0304793 | A1 | 12/2009 | Boehm | |
| 2009/0317355 | A1 | 12/2009 | Roth et al. | |
| 2010/0015223 | A1 | 1/2010 | Cailly-Dufestel et al. | |
| 2010/0055133 | A1 | 3/2010 | Duffield et al. | |
| 2010/0098771 | A1 | 4/2010 | Mehta | |
| 2010/0099696 | A1 | 4/2010 | Soscia et al. | |
| 2011/0002985 | A1 | 1/2011 | Shah et al. | |
| 2012/0164228 | A1 | 6/2012 | Suplie et al. | |
| 2012/0202838 | A1 | 8/2012 | Ghosh et al. | |
| 2012/0321716 | A1 | 12/2012 | Vachon et al. | |
| 2013/0034503 | A1 | 2/2013 | Howard et al. | |
| 2014/0079740 | A1 | 3/2014 | Salama | |
| 2014/0093592 | A1 * | 4/2014 | Singh | A61K 45/06 424/734 |
| 2014/0275276 | A1 * | 9/2014 | Basstanie | A61K 47/26 514/646 |
| 2015/0030677 | A1 | 1/2015 | Adjei et al. | |
| 2015/0057304 | A1 | 2/2015 | Thompson et al. | |
| 2015/0118303 | A1 | 4/2015 | Haswani et al. | |
| 2015/0328168 | A1 | 11/2015 | Daviaud-Venet et al. | |
| 2016/0310418 | A1 | 10/2016 | Fanda et al. | |
| 2017/0143637 | A1 | 5/2017 | Haswani et al. | |
| 2017/0157052 | A1 * | 6/2017 | Haswani | A61K 31/485 |
| 2017/0354654 | A1 | 12/2017 | Sackler | |
| 2018/0185354 | A1 * | 7/2018 | Haswani | A61K 31/485 |
| 2018/0296501 | A1 | 10/2018 | During | |
| 2019/0380978 | A1 | 12/2019 | Rands et al. | |
| 2020/0121619 | A1 | 4/2020 | Rey | |
| 2020/0147005 | A1 | 5/2020 | Kagan et al. | |

FOREIGN PATENT DOCUMENTS

| | | | |
|---|---|---|---|
| EP | 1504757 | A2 | 2/2005 |
| EP | 1694724 | A1 | 8/2006 |
| EP | 1782834 | A2 | 5/2007 |
| JP | 2015-511953 | | 4/2015 |
| WO | 99/39698 | A1 | 8/1999 |
| WO | 01/80826 | A2 | 11/2001 |
| WO | 02/36099 | A1 | 5/2002 |
| WO | 2002/092059 | A1 | 11/2002 |
| WO | 2004/026256 | A2 | 4/2004 |
| WO | 2004/026262 | A2 | 4/2004 |
| WO | 2004/064807 | A1 | 8/2004 |
| WO | 2004/093819 | A2 | 11/2004 |
| WO | 2005/034930 | A1 | 4/2005 |
| WO | 2007/103293 | A2 | 9/2007 |
| WO | 2008/024490 | A2 | 2/2008 |
| WO | 2008/134071 | A1 | 11/2008 |
| WO | 2009/036812 | A1 | 3/2009 |
| WO | 2009/059701 | A2 | 5/2009 |
| WO | 2010/033195 | A1 | 3/2010 |
| WO | 2013/077851 | A1 | 5/2013 |
| WO | 2013/128276 | A2 | 9/2013 |
| WO | 2014/057351 | A1 | 4/2014 |
| WO | 2015/066172 | A1 | 5/2015 |
| WO | 2015/120201 | A1 | 8/2015 |
| WO | 2016/094358 | A1 | 6/2016 |
| WO | 2017/059374 | A1 | 4/2017 |
| WO | 2020/075134 | A1 | 4/2020 |

OTHER PUBLICATIONS

Yanagihara et al (Yakugaku Zasshi (Journal of the Pharmaceutical Society of Japan), 1999, vol. 119, pp. 980-987) (Year: 1999).

Bannwarth, B. "Will Abuse-Deterrent Formulations of Opioid Analgesics Be Successful In Achieving Their Purpose?" Drugs, 2012, vol. 72, pp. 1713-1723.

Esin et al., "Neuropathic cancer pain: What we are dealing with? How to manage it?", OncoTargets and Therapy (2014), vol. 7, pp. 599-618.

Frohoff-Hulsmann et al., "Aqueous Ethyl Cellulose Dispersion Containing Plasticizers of Different Water Solubility and Hydroxypropyl

(56) References Cited

OTHER PUBLICATIONS

Methyl-Cellulose as Coating Material for Diffusion Pellets II: Properties of Sprayed Films", Euro. J. of Pharma and Biopharma. 1999, vol. 48, pp. 67-75.
Gustafsson et al., "Characterisation of Particle Properties and Compaction Behaviour of Hydroxypropyl Methylcellulose with Different Degrees of Methoxyl/Hydroxypropl Substitution", Euro. J. of Pharmaceutical Sci. (1999), vol. 9, pp. 171-184.
Hyppola et al.,"Evaluation of Physical Properties of Plasticized Ethyl Cellulose Films Cast From Ethanol Solution Part I", Int'l J. of Pharma. (1996), vol. 133, pp. 161-170.
Siepmann et al., "A New Model Describing the Swelling and Drug Release Kinetics from Hydroxypropyl Methylcellulose Tablets", J. of Pharma. Sci. (1999), vol. 88, No. 1, pp. 65-72.
Sung et al., "Effect of Formulation Variables on Drug and Polymer Release from HPMC-Based Matrix Tablets", International Journal of Pharmaceutics (1996), vol. 142, pp. 53-60.
Viriden et al., "Investigation of Critical Polymer Properties for Polymer Release and Swelling of HPMC Matrix Tablets", Euro. J. Pharma. Sci. (2009), vol. 36, pp. 297-309.

* cited by examiner

ABUSE-DETERRENT DOSAGE FORMS CONTAINING ESKETAMINE

CROSS-REFERENCE TO RELATED APPLICATIONS

The present application is a continuation-in-part of U.S. patent application Ser. No. 16/869,309, filed May 7, 2020, which claims the benefit of priority to U.S. Provisional App. No. 62/844,286, filed May 7, 2019, the entire contents of which are hereby incorporated by reference.

TECHNICAL FIELD

The present disclosure pertains to oral dosage forms that contain abuse-deterrent features.

BACKGROUND

Pharmaceutical products, including both prescription and over-the-counter pharmaceutical products, while useful for improving health or alleviating undesirable symptoms of a person in need, are also susceptible to intentional and unintentional abuse and overdosing. Commonly abused active pharmaceutical ingredients include psychoactive drugs, anxiolytics, sedative hypnotics, stimulants, depressants, and analgesics such as narcotic analgesics, among others.

Some common techniques for intentionally abusing a drug may begin with a prospective abuser obtaining a solid dosage form, such as an orally administered tablet or capsule, and crushing the solid dosage form into a powder. The powder may be administered by an abuser by nasal insufflation to introduce the drug to the abuser's bloodstream intranasally. Alternately, the crushed dosage form may be combined with a solvent that is capable of dissolving the drug (active pharmaceutical ingredient, or "API") and the solvent containing the dissolved drug may then be injected directly into an abuser's bloodstream. In the case of immediate release oral dosage forms, an abuser might simply ingest multiple units (e.g., tablets) of the dosage form together, e.g., simultaneously, or over an abbreviated period of time. Each one of the multiple dosage form units immediately releases an amount of drug, thereby producing a short-term concentration spike of the drug in the user's bloodstream and the desired "high" in the user.

The pharmaceutical industry has identified various mechanisms of adapting drug compositions and oral dosage forms to discourage abuse of oral dosage forms. Pharmaceutical companies have studied dosage forms that contain a nasal irritant or an effervescent agent, which can cause irritation or pain in a nasal passage if the dosage form is crushed and then snorted, thus discouraging abuse by nasal insufflation.

Pharmaceutical companies studied adding gelling polymers to dosage forms to prevent abuse by injection. If the dosage form is crushed to a powder and combined with a small amount of solvent, the gelling polymer can cause the combination to take the form of a highly viscous liquid or gel that cannot be administered by injection. Another possible abuse deterrent may be addition of an emetic agent which can deter abuse by causing emesis on ingestion of multiple doses. Another abuse deterrent involves adding an antagonist of an API to a dosage form that will substantially block the effect of the drug.

Although the pharmaceutical industry has identified of a variety of abuse deterrent (sometimes referred to as "abuse-resistant") features useful with oral dosage forms, there is continuing need to improve abuse deterrent features in order to prevent abuse or overdosing of active pharmaceutical ingredients.

SUMMARY

Disclosed herein are oral dosage forms comprising: (i) a first population of core-shell particles, each of the core-shell particles of the first population comprising a core that includes a gelling polymer and a wax; an active pharmaceutical layer surrounding the core, the active pharmaceutical layer comprising esketamine; and at least one layer surrounding the active pharmaceutical layer, the at least one layer comprising a pH-sensitive film comprising a pH-sensitive polymer that is insoluble in water at a pH greater than 5; and, (ii) a matrix comprising a carbomer gelling polymer and sodium bicarbonate, wherein the carbomer gelling polymer and sodium bicarbonate are present in said dosage form in a ratio by weight percentage of about 2:2 based on the total weight of the dosage form; wherein the dosage form exhibits an immediate release profile of the esketamine when administered to a human in therapeutic doses, and an extended release profile of the esketamine when administered to a human in supratherapeutic doses.

Also disclosed herein are abuse resistant oral dosage forms for the administration of esketamine to a subject comprising: (i) a first population of core-shell particles, each of the core-shell particles of the first population comprising a core, an active pharmaceutical layer surrounding the core comprising esketamine or a pharmaceutically acceptable salt thereof, and at least one layer surrounding the active pharmaceutical layer, the at least one layer comprising a pH-sensitive film comprising a pH-sensitive polymer that is insoluble in water at a pH greater than 5; and, (ii) a matrix comprising a carbomer gelling polymer and sodium bicarbonate, wherein the carbomer gelling polymer and sodium bicarbonate are present in a ratio by weight percentage of about 2:2 based on the total weight of the dosage form; wherein the dosage form exhibits an immediate release profile of esketamine having not less than 90% of the esketamine released in 60 minutes, wherein the release profile is evaluated by dissolution of the tablet in 300 mL of 0.1N HCl media using USP II apparatus at 50 RPM paddle speed and 37° C.; wherein the dosage form exhibits an immediate release profile of the esketamine when administered to a human in therapeutic doses, and an extended release profile of the esketamine when administered to a human in supratherapeutic doses, or wherein the dosage form exhibits abuse resistant properties when physically manipulated, or wherein the dosage form exhibits abuse resistant properties when physically manipulated and administered in a manner not consistent with oral dosing, or wherein the dosage form exhibits abuse resistant properties when administered in a manner intended to result in administration of the esketamine in a higher than therapeutic dose.

The present disclosure also provides oral tablets for the administration of esketamine to a subject comprising: a total weight of not less than 800 mg, and having 40 mg of esketamine (base equivalent), the esketamine (base equivalent) representing less than 5.0% by weight of the total weight of the tablet, or a total weight of not less than 571 mg, and having 20 mg of esketamine (base equivalent), the esketamine (base equivalent) representing less than 3.5% by weight of the total weight of the tablet; wherein the tablet exhibits an immediate release profile of esketamine having not less than 90% of the esketamine released in 60 minutes, and wherein the release profile is evaluated by dissolution of the tablet in 300 mL of 0.1N HCl media using USP II apparatus at 50 RPM paddle speed and 37° C.; and wherein the dosage form exhibits an immediate release profile of the esketamine when administered to a human in therapeutic doses, and an extended release profile of the esketamine when administered to a human in supratherapeutic doses, or wherein the tablet exhibits abuse resistant properties when physically manipulated, or wherein the tablet exhibits abuse resistant properties when physically manipulated and administered in a manner not consistent with oral dosing, or wherein the tablet exhibits abuse resistant properties when administered in a manner intended to result in administration of the esketamine in a higher than therapeutic dose.

Also disclosed are methods of reducing the potential for abuse by a human of an active pharmaceutical ingredient comprising esketamine, comprising providing to the human a dosage form as described herein.

Also provided are methods of reducing the potential for abuse by a human of an active pharmaceutical ingredient comprising esketamine by simultaneous oral ingestion of multiple dosage units comprising the active pharmaceutical ingredient, comprising providing to the human a dosage form as described herein.

The present disclosure also provides methods for treating or preventing pain or discomfort in a subject in need thereof by administering to the subject a dosage form as described herein.

Also disclosed are methods for treating depression in a subject in need thereof by administering to the subject a dosage form as described herein.

The present disclosure also provides methods of reducing the potential for abuse by nasal insufflation by a human of an active pharmaceutical ingredient comprising esketamine, comprising providing to the human a dosage form as described herein.

DETAILED DESCRIPTION OF ILLUSTRATIVE EMBODIMENTS

Figure 1A:
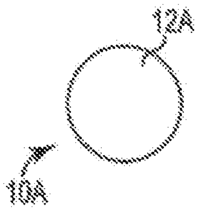
FIG. 1A, FIG. 1B, and FIG. 1C illustrate embodiments of core-shell particles, in cross section, for inclusion in the presently disclosed dosage forms.

Abuse deterrent and resistant features can include the ability of a dosage form to produce a highly viscous liquid or gel when crushed and exposed to a solvent, when administered in supratherapeutic doses (in doses that are higher than what is prescribed pursuant to a legitimate treatment regimen), or both, in order to prevent abuse by such methods as intravenous injection, nasal insufflation, and oral supratherapeutic dosing. One challenge associated with incorporating this type of abuse-deterrent feature is whether the resulting viscous liquid or gel possesses characteristics that are required for preventing the above-noted abuse modalities. For example, in order to prevent drug from being released in a dosage form in sufficient quantities to produce the desired effect of the abuse, a gel must be appropriately viscous and uniform. A gel that is runny or non-uniform (e.g., containing portions that are more fluid and portions that are less fluid) will be less effective in blocking commonly-attempted forms of abuse and release of drug. The present disclosure pertains to dosage forms that produce high quality abuse deterrent features when subjected to attempted abuse. In basic terms, the dosage forms that are disclosed herein exhibit an immediate release profile of drug when administered to a human in therapeutic doses, and an extended release profile of drug when administered to a human in supratherapeutic doses.

More particularly, it has been discovered that specific ratios of gelling polymer, particularly carbomer gelling polymer, to pH adjusting compound within the matrix of the dosage forms can be critical for allowing the dosage form, when administered in supratherapeutic doses, to produce a gel having superior physical characteristics for purposes of thwarting abuse of esketamine from the dosage forms. This finding, among others, is described more fully, infra.

Ideally, the abuse resistant and deterrent features include those that thwart other commonly used approaches for extracting higher doses of active ingredient than would be appropriate pursuant to a therapeutic dosing regimen. One commonly used approach for abusing an active ingredient involves crushing a dosage form and nasally insufflating the crushed dosage form. As disclosed more fully herein, the presently disclosed dosage forms are capable of resisting attempts of this type by limiting the amount of active ingredient that diffuses across nasal membranes when the dosage form is crushed and then nasally insufflated.

Another commonly used approach for extracting a higher than therapeutically appropriate dose of an active ingredient involves physically manipulating the dosage form (e.g., crushing it) followed by heating the material that results from the physical manipulation. The heating step can function to defeat a gelling mechanism that otherwise prevents the extraction of active ingredient. However, as also described more fully herein, the presently disclosed dosage forms prevent extraction of active ingredient even when physically manipulated (e.g., crushed) and subjected to heating.

A further commonly used approach for extracting active ingredient involves physically manipulating (e.g., crushing) a dosage form and selectively ingesting particles that have a higher concentration of active ingredient and a lower concentration of inactive excipient. The present inventors have discovered that the dosage forms disclosed herein are able to resist attempts to abuse the dosage form in this additional manner, and this feature is described more fully infra.

In the present disclosure, the singular forms “a”, “an”, and “the” include the plural reference, and reference to a particular numerical value includes at least that particular value, unless the context clearly indicates otherwise. Thus, for example, a reference to “a filler” is a reference to one or more of such reagents and equivalents thereof known to those skilled in the art, and so forth. Furthermore, when indicating that a certain element “may be” X, Y, or Z, it is not intended by such usage to exclude in all instances other choices for the element.

When values are expressed as approximations, by use of the antecedent “about”, it will be understood that the particular value forms another embodiment. As used herein, “about X” (where X is a numerical value) preferably refers to ±10% of the recited value, inclusive. For example, the phrase “about 8” can refer to a value of 7.2 to 8.8, inclusive. This value may include “exactly 8”. Where present, all ranges are inclusive and combinable. For example, when a range of “1 to 5” is recited, the recited range should be construed as optionally including ranges “1 to 4”, “1 to 3”, “1-2”, “1-2 & 4-5”, “1-3 & 5”, and the like. In addition, when a list of alternatives is positively provided, such a listing can also include embodiments where any of the alternatives may be excluded. For example, when a range of “1 to 5” is described, such a description can support situations whereby any of 1, 2, 3, 4, or 5 are excluded; thus, a recitation of “1 to 5” may support “1 and 3-5, but not 2”, or simply “wherein 2 is not included.”

The entire disclosures of each patent, patent application, and publication cited or described in this document are hereby incorporated herein by reference.

Esketamine is the S-enantiomer of the racemic cyclohexanone derivative ketamine, a glutamate N-Methyl-D-aspartate (NMDA) receptor antagonist. It is indicated as an anesthetic, and is approximately twice as potent as an anesthetic as racemic ketamine. The chemical structure of esketamine is shown below:

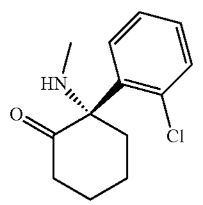 [SMILES: CN[C@]1(c2ccccc2Cl)CCCCC1=O]

Esketamine

Esketamine is a schedule III controlled substance, and can produce dissociative and hallucinogenic effects when subjected to misuse or abuse. Thus, there exists a risk of abuse with respect to dosage forms containing esketamine.

The present disclosure relates, inter alia, to oral dosage forms comprising: (i) a first population of core-shell particles, each of the core-shell particles of the first population comprising a core that includes a gelling polymer and a wax; an active pharmaceutical layer surrounding the core comprising esketamine; and at least one layer surrounding the active pharmaceutical layer, the at least one layer comprising a pH-sensitive film comprising a pH-sensitive polymer that is insoluble in water at a pH greater than 5; and, (ii) a matrix comprising a carbomer gelling polymer and sodium bicarbonate, wherein the carbomer gelling polymer and sodium bicarbonate are present in said dosage form in a ratio by weight percentage of about 2:2 based on the total weight of the dosage form. The disclosed dosage forms can exhibit an immediate release profile of the esketamine when administered to a human in therapeutic doses, and an extended release profile of the esketamine when administered to a human in supratherapeutic doses. The term “wt %” as used herein, refers to the weight percentage of a substance, or combination of substances, based on the total weight of all substances weighed.

Unless otherwise specified, “esketamine” as used throughout the present disclosure can also refer to isotopically-enriched esketamine. “Esketamine” as used herein may also refer to that compound in its free base form (i.e., base equivalent), or to a salt of the compound, such as esketamine hydrochloride.

As used herein, esketamine that is “isotopically-enriched” refers to a condition in which the abundance of deuterium ($^{2}H$), $^{13}C$, or $^{15}N$ at any relevant site of the compound is substantially more than the abundance of deuterium, $^{13}C$, or $^{15}N$ naturally occurring at that site in an amount of the compound. A relevant site in a compound as used above is a site which would be designated as “H” or “C” or “N” in a chemical structure representation of the compound when not enriched. The expression, “naturally occurring,” as used above refers to the abundance of the particular atom which would be present at a relevant site in a compound if the compound was prepared without any affirmative synthesis step to enrich the abundance of a different isotope. Thus, for example in a “deuterium-enriched” compound, the abundance of deuterium at any relevant site in the chemical structure of the esketamine can range from an amount that is substantially more than the natural abundance of deuterium (about 0.0115%) all the way up to 100%, for example, from about 1% to about 100%, or from about 10% to about 100%, or from about 50% to about 100%, or from about 90% to about 100%.

Similarly, for a “$^{13}C$-enriched” compound, the abundance of $^{13}C$ at any relevant site in the chemical structure of the API can range from an amount that is substantially more than the natural abundance of $^{13}C$ (about 1.109%) all the way up to 100%, for example, from about 5% to about 100%, or from about 10% to about 100%, or from about 50% to about 100%, or from about 90% to about 100%. Similarly for a “$^{15}N$-enriched” compound, the abundance of $^{15}N$ at any relevant site in the chemical structure of the esketamine can range from an amount that is substantially more than the natural abundance of $^{15}N$ (about 0.364%) all the way up to 100%, for example, from about 1% to about 100%, or from about 10% to about 100%, or from about 50% to about 100%, or from about 90% to about 100%.

Isotopically-enriched compounds can generally be prepared by conventional techniques known to those skilled in the art. Such isotopically-enriched compounds can also be prepared by adapting conventional processes as described in the scientific literature for synthesis of esketamine as suitable for formulation according to the invention, and using an appropriate isotopically-substituted reagent (or reagents) in place of the corresponding non isotopically-substituted reagent(s) employed in the conventional synthesis of the non isotopically-enriched compounds. Examples of ways to obtain a deuterium-enriched compound include exchanging hydrogen with deuterium or synthesizing the compound with deuterium-enriched starting materials.

As used herein, expressions such as “abuse deterrent” and “abuse resistant”, and “preventing”, “deterring”, “resisting”, or “inhibiting” abuse, relate to the ability of features of the claimed formulations to provide significant physical or chemical impediments to the use of an active pharmaceutical ingredient for objectives other than its primary therapeutic indications. The objective in such deterrence includes both making abuse practices significantly more difficult to carry out, and making any product resulting from an attempt to carry out such abuse practices on the claimed formulations significantly less desirable, less profitable, and less abusable to the potential abuser.

The term “immediate release”, as used herein, refers to a dosage form that upon oral ingestion by a human releases substantially all of a contained active pharmaceutical ingredient into a gastrointestinal tract for biological uptake in a short time. In vitro methods of measuring a release profile of a dosage form, for the purpose of determining whether a dosage form exhibits an immediate release or extended release dissolution profile, are known in the pharmaceutical arts. By such methods, examples of immediate release dosage forms as described herein can be measured to be capable of releasing substantially all of a total amount of at least one type of active pharmaceutical ingredient (“API”) (e.g., esketamine), contained in the dosage form (e.g., at least 75, 80, 90, 95, 97 or 100 weight percent of the total amount of the API in a dosage form) into a solution (e.g., acidic aqueous solution) of a suitable pH within 240 minutes, e.g., in less than 180 minutes, less than 90 minutes, or less than 60, 30, 15, or 5 minutes. For example, a release profile of a dosage form of the present description may be measured by a method that exposes the dosage form to a volume of up to 900 mL (e.g., 300 mL, 500 mL, or 900 mL, based on various test methods) of hydrochloric acid (from 0.01N to 0.1N), e.g., aqueous hydrochloric acid, at a pH of from 1 to 2, and at a temperature of 37 degrees Celsius. According to some embodiments, the dosage forms described herein release at least 90% or at least 95% of API in less than 30 minutes when administered at therapeutic doses (e.g., as one single dosage unit), wherein the release profiles may be evaluated, for example, by dissolution in 500 mL of 0.01N HCl media using USP II apparatus at 50 RPM paddle speed and 37° C. In some embodiments, the 0.01N HCl medium is subjected to deaeration based on the recommendations of USP <1092>. A release profile of a dosage form of the present description may alternatively be measured by a method that exposes the dosage form to a volume of up to 900 mL (e.g., 200 mL, 300 mL, 400 mL, 500 mL, 600 mL, 700 mL, 800 mL, or 900 mL, based on various test methods) of an aqueous buffer solution (e.g., an acetate buffer solution) at a pH that is representative of the pH conditions of a fed stomach, e.g., at a pH of about 4.5, and at a temperature of 37 degrees Celsius, with or without deaeration.

The term “extended release” can be defined as not more than 75% release of the API at 30 minutes, wherein the release profiles may be evaluated, for example, by dissolution in 400 mL of 0.1N HCl media using USP II apparatus at 50 RPM paddle speed and 37° C. In some embodiments, the 0.1N HCl medium is subjected to deaeration based on the recommendations of USP <1092>.

As used herein, the phrase, “administered in a manner intended to result in administration of the esketamine in a higher than therapeutic dose” includes administration in a manner that would result in a $C_{max}$ of esketamine that is higher or significantly higher than a therapeutic $C_{max}$ of esketamine considered to be safe and efficacious for treating a particular disease or disorder, if the esketamine was administered in a dosage form that did not include the features of a dosage form described herein.

According to some embodiments, the dosage forms described herein demonstrate (i) not less than 95% of API released in 30 minutes when administered at therapeutic doses, wherein the release profile is evaluated by dissolution in 500 mL of deaerated 0.01N HCl media using USP II apparatus at 50 RPM paddle speed and 37° C.; and (ii) not more than 75% release of the API at 30 minutes when administered at supratherapeutic doses, wherein the release profiles may be evaluated by dissolution in 400 mL of deaerated 0.1N HCl media using USP II apparatus at 50 RPM paddle speed and 37° C. In this context, a “supratherapeutic dose” can be understood to correspond to administration of five or more, six or more, seven or more, eight or more, nine or more, ten or more, eleven or more, or twelve or more individual dose units, e.g., tablets, simultaneously. It will also be understood that administering multiple individual dose units simultaneously would reasonably include administering those multiple doses sequentially over a short time interval, e.g., over an interval of less than 60 minutes, less than 30 minutes, less than 15 minutes, less than 5 minutes, or less than one minute.

Dosage forms as described herein can be formulated to provide an immediate release profile of esketamine, while including effective or advantageous abuse deterrent features that are effective to deter abuse of the API. The combination of immediate release of esketamine with broad abuse resistance of the same API for multiple abuse modalities including multi-tablet dosing, as described herein, is not believed to be previously known. The present dosage forms can also be more specifically characterized as resistant to certain common methods of abuse, such as 1) abuse by injection (e.g., by steps that include grinding a dosage form and dissolving it), 2) abuse by nasal insufflation (e.g., also by grinding and optionally dissolving the dosage form), and 3) abuse by multi-tablet dosing by oral consumption, meaning simultaneous oral ingestion of multiple, supratherapeutic quantities of orally administered dosage forms such as tablets or capsules. The third mode of abuse, multi-tablet dosing, is particularly common with immediate release dosage forms and is particularly difficult to defend against by design of a dosage form structure or by formulation. Accordingly, the ability of the presently-described dosage forms to prevent or deter abuse (or even accidental overdose) by multi-tablet dosing represents a particularly noteworthy feature.

Figure 4:
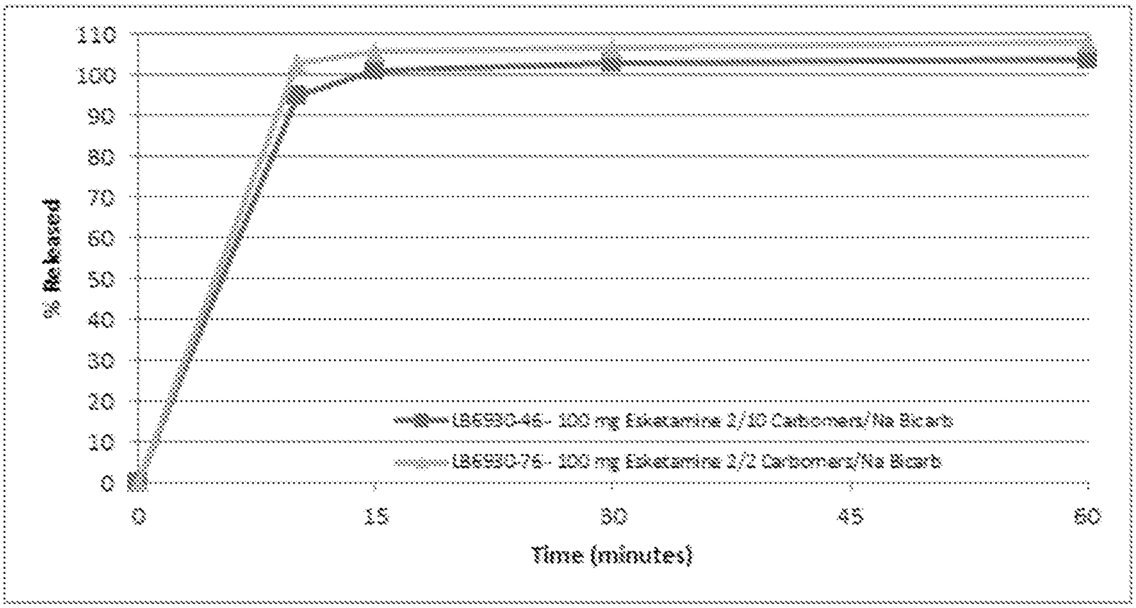
FIG. 4 shows the results of single-tablet dissolution testing of an inventive dosage form according to the present disclosure and of a comparative dosage form.
Figure 5:
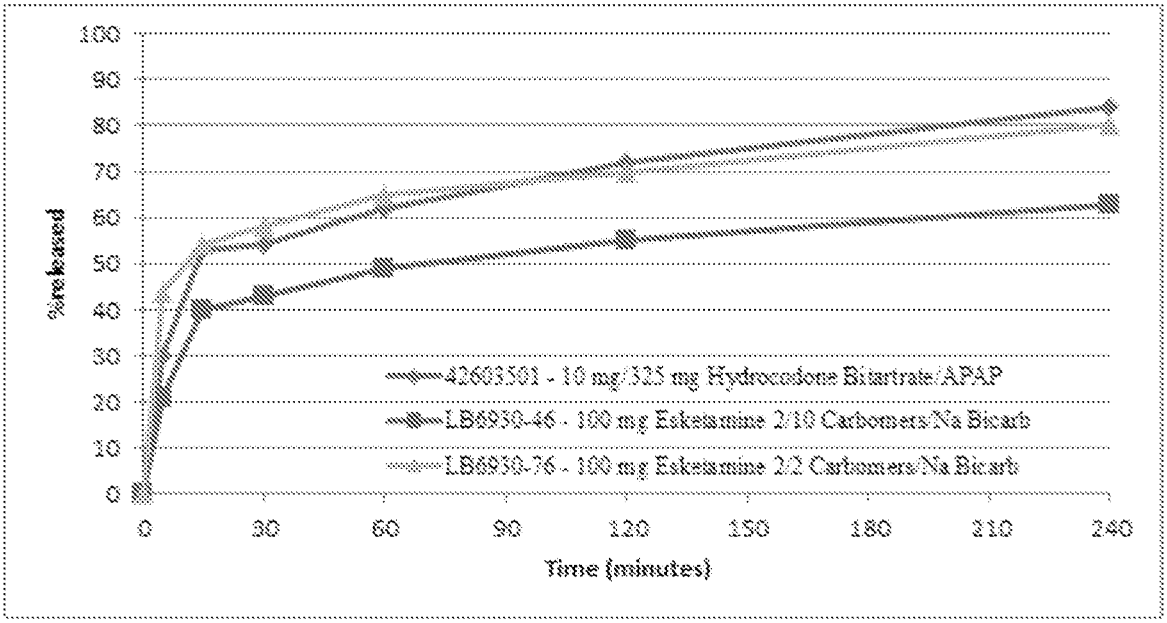
FIG. 5 shows the results of multiple-tablet dissolution testing of a supratherapeutic dose of an inventive dosage form according to the present disclosure and of a supratherapeutic dose of comparative dosage form.

In vitro testing as described herein demonstrated that the presently disclosed dosage forms provide deterrence against abuse by multi-tablet dosing. More specifically, in vitro testing of exemplary dosage forms was performed by conducting dissolution testing of one or more dosage forms (tablets) in 400 mL of deaerated 0.1N HCL maintained at 37 degrees Celsius using a 50 RPM paddle speed. See Example 5, infra. As shown in FIG. 4 and FIG. 5, the amount (percentage per tablet) of esketamine released in the media is reduced when multiple dosage units are administered together, as opposed to when a single dosage unit is subjected to release testing. The data also demonstrate that the tested dosage forms are effective to prevent increased levels of esketamine uptake by an individual who would accidentally ingest multiple tablets, and are thereby effective to prevent or reduce the risk of an unintentional overdose of the esketamine.

Accordingly, dosage forms as described herein provide a method of preventing or attenuating a short-term concentration spike of esketamine in the bloodstream of a patient who is prescribed the drug, or in the bloodstream of an abuser who consumes the drug for recreational purposes, in the event that a patient or the abuser intentionally or unintentionally consumes a supratherapeutic dose of the drug. Thus, dosage forms as described herein can provide a method whereby a drug overdose may be prevented, reduced, or attenuated when a subject intentionally or unintentionally consumes a supratherapeutic dose of the drug. As a result, dosage forms as described herein can provide a greater amount of time for medical intervention in the case of intentional or accidental overdose by ingestion of a supratherapeutic dose.

A "supratherapeutic dose" refers to a dose that exceeds what would normally be prescribed for therapy with respect to a particular disease or disorder, e.g., a dose that results in a $C_{max}$ that exceeds what would normally be needed for effective therapy of the particular disease or disorder. For example, a supratherapeutic dose may represent four, five, six, seven, eight, nine, ten, eleven, twelve, or more than twelve individual dosage units (e.g., tablets, capsules, and the like).

Dosage forms as described herein can include one or more gelling polymers. A gelling polymer can act as an abuse deterrent feature by compromising abuse practices involving dissolution of the active pharmaceutical ingredient of the dosage in a small volume of solvent in an attempt to render the API more accessible or easily isolatable. A gelling polymer can deter or prevent abuse of the esketamine by increasing the viscosity of a combination of the ground dosage form with solvent to an extent that is sufficient to prevent the combination or the esketamine from being taken up by and injected using a syringe. When exposed to a volume of solvent such as a $C_{1-4}$ alcohol (e.g., ethanol) or water, a gelling polymer from a ground (e.g., crushed) dosage form can form a non-injectable mass that ranges in type from an insoluble mass, to a gel, to a viscous slurry, that exhibits a viscosity that substantially prevents uptake by or injection from a needle of a hypodermic syringe.

Suitable gelling polymers include one or a combination of polymers that, as part of a dosage form, upon contact of the dosage form with a volume of solvent, absorb the solvent and swells to form a viscous or semi-viscous substance that significantly reduces or minimizes the amount of free solvent that can contain an amount of a solubilized esketamine and that can be drawn into a syringe. The gelled polymer can also or alternatively function to reduce the overall amount of drug that is extractable with the solvent by entrapping the drug in a gel matrix.

At the same time, the gelling polymers used herein do not interfere with desired dissolution of the dosage forms, the desired release (immediate release) of esketamine from the dosage forms, or the uptake of the esketamine by a patient ingesting the intact immediate release dosage form for an intended therapeutic purpose. The gelling polymer may be present in the dosage forms within a core-shell particle that includes active pharmaceutical ingredient, such as in a core or in a layer ("shell") surrounding the core, wherein an amount of active pharmaceutical ingredient is contained within the core, in a layer that is coated core, or both. Another exemplary location is within a matrix. Gelling polymer may also or alternatively be present in a core-shell particle that does not include esketamine, such as in the core, or in a layer surrounding the core.

The gelling polymer can be present in a dosage form at any desired amount and within any portion of the present dosage forms. The amount of gelling polymer can be any useful amount, meaning an amount that can produce an abuse-deterrent viscous mixture or gel if the dosage form is crushed, ground, powdered, or otherwise similarly manipulated, and mixed with solvent. A useful amount of total gelling polymer in a dosage form may be in a range from 0.5 to 90 weight percent gelling polymer based on a total weight of the dosage form, e.g., from 0.7 to 20, 1 to 20, 2 to 15, 2 to 10, or 3 to 7 weight percent gelling polymer based on total weight of the dosage form.

The presently disclosed dosage forms include core-shell particles, and the cores of such particles preferably contain a gelling polymer. A core (uncoated) of a core-shell particle can contain any useful amount of gelling polymer, up to and including 100 percent gelling polymer in a core of a core-shell particle, e.g., from 10 to 95 weight percent gelling polymer based on the total weight of the core, such as 20 to 90, 25 to 85, 30 to 85, 40 to 85, 40 to 80, 45 to 75, 50 to 75, 55 to 70, 55 to 65, or 57 to 62 weight percent gelling polymer based on the total weight of the core.

Described in terms of total weight of a dosage form, an amount of gelling polymer present in a core of a core shell polymer may be, e.g., in a range from 0.5 to 15 weight percent gelling polymer (present in the core) per total weight of the dosage form, such as from 1 to 10 weight percent gelling polymer (present in the core) per total weight dosage form.

In certain embodiments, gelling polymer may also or alternatively be provided in the matrix portion of the present dosage forms. The types of gelling polymers in the respective portions of the present dosage forms may be the same or different. For example, when present, the gelling polymer in the core of the core-shell particles may be the same or a different type as a gelling polymer in the matrix of the dosage form.

A gelling polymer for use in the present dosage forms can be any polymeric material that exhibits the ability to retain a significant fraction of adsorbed solvent in its molecular structure, e.g., the solvent being a solvent otherwise useful by an abuser to extract API from a dosage form or a crushed or powdered dosage form, the solvent for example being water or a $C_1$ to $C_4$ alcohol such as ethanol or methanol. Exemplary gelling polymers include materials that can swell or expand to a very high degree when placed in contact with such a solvent. The swelling or expansion may cause the gelling polymer to experience from a two- to one-thousand-fold volume increase relative to the dry state. More specific examples of gelling polymers include swellable polymers sometimes referred to as osmopolymers or hydrogels. The gelling polymer may be non-cross-linked, lightly cross-linked, or highly crosslinked. The crosslinking may involve covalent or ionic bonds with the polymer possessing the ability to swell in the presence of a solvent, and when cross-linked will not dissolve in the solvent.

A gelling polymer, upon dissolution or dispersion in an aqueous solution or dispersion (e.g., water) at a concentration of 2% w/w (based on the dry material), preferably creates a solution/dispersion with a viscosity of from about 100 to about 200,000 mPa·s (e.g., 4,000 to 175,000 mPa·s, and 4,000 to 50,000 mPa·s) as measured at 20 degrees Celsius (+/−0.2 degree Celsius) using the analysis method described in the USP 33 monograph for Hypromellose, incorporated herein by reference.

Generally suitable gelling polymers include pharmaceutically acceptable polymers that undergo an increase in viscosity upon contact with a solvent, as described. Various examples of polymers are known to be useful in this manner, generally including natural and synthetic starches (i.e., modified or pregelatinized modified starch), natural and synthetic celluloses, acrylates, and polyalkylene oxides. Examples of natural starches include natural starches include corn starch, potato starch, rice starch, tapioca starch and wheat starch, hydroxypropyl starch such as hydroxypropyl corn starch, hydroxypropyl pea starch and hydropropyl potato starch (derivative of natural starch). Examples of synthetic starches, i.e., modified or pregelatinized modified starch, include acetylated distarch adipate, waxy maize basis, acid-treated maize starch, acid-treated waxy maize starch, distarch phosphate, waxy maize basis, oxidized waxy maize starch, and sodium octenyl succinate starch. Examples of celluloses include carboxymethyl cellulose calcium, carboxymethylcellulose sodium, ethycellulose, methylcellulose, cellulose ethers such as hydroxypropyl cellulose, hydroxyethylcellulose, hydroxy ethyl methyl cellulose, hydroxypropyl methyl cellulose, carboxymethylcellulose sodium, and low substituted hydroxypropyl cellulose. Examples of acrylates include Eudragit RS, RL, NE, NM. Examples of polyalkylene oxides include polyethylene oxide such as POLYOX N10, N80, N60K, WSR-1105 LEO, or WSR-301 LEO, or WSR-303 LEO.

Accordingly, examples of suitable gelling polymers for use in any component of the present dosage forms include, among others, polyethylene oxide, polyvinyl alcohol, hydroxypropyl methyl cellulose, hydroxypropyl cellulose, methyl cellulose, hydroxyethyl methyl cellulose, sodium carboxymethylcellulose, hydroxyethyl cellulose, and polyacrylic acid, and other high molecular weight polymers capable of attaining a viscosity level effective to prevent uptake in a syringe, if combined with a small volume of solvent as described.

Other examples of suitable gelling polymers can include, if of sufficiently high molecular weight; ethylcellulose, cellulose acetate, cellulose acetate propionate, cellulose acetate butyrate, cellulose acetate phthalate and cellulose triacetate, cellulose ether, cellulose ester, cellulose ester ether, cellulose; acrylic resins comprising copolymers synthesized from acrylic and methacrylic acid esters, for example acrylic acid and methacrylic acid copolymers, methyl methacrylate copolymers, ethoxyethyl methacrylates, cyanoethyl methacrylate, poly(acrylic acid), poly (methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

Exemplary gelling polymers also include natural polymers such as those derived from a plant or animal, as well as polymers prepared synthetically. Examples include polyhydroalkylcellulose having a molecular weight greater than 50,000; poly(hydroxy-alkylmethacrylate) having a molecular weight of from 5,000 to 5,000,000; poly(vinyl-pyrrolidone) having a molecular weight of from 100,000 to 3,000,000; anionic and cationic hydrogels; poly(electrolyte) complexes; poly(vinyl alcohol) having a low acetate residual; a swellable mixture of agar and carboxymethyl cellulose; a swellable composition comprising methyl cellulose mixed with a sparingly cross-linked agar; a polyether having a molecular weight of from 10,000 to 6,000,000; water-swellable copolymer produced by a dispersion of finely divided copolymer of maleic anhydride with styrene, ethylene, propylene, or isobutylene; water swellable polymer of N-vinyl lactams; and the like.

Other polymers useful as gelling polymers include pectin having a molecular weight ranging from 30,000 to 300,000; polysaccharides such as agar, acacia, karaya, tragacanth, algins and guar; polyacrylamides; water-swellable indene maleic anhydride polymers; Good-rite® polyacrylic acid having a molecular weight of 80,000 to 200,000; Polyox® polyethylene oxide polymers having a molecular weight of 100,000 to 7,000,000; starch graft copolymers; Aqua-Keep® acrylate polymers with water absorbability of 400 times its original weight; diesters of polyglucan; a mixture of cross-linked polyvinyl alcohol and poly(-vinyl-2-pyrrolidone); poly(ethylene glycol) having a molecular weight of 4,000 to 100,000.

In certain embodiments, a gelling polymer may include hydroxypropyl methyl cellulose (e.g., Hypromellose or HPMC), and hydroxy methyl cellulose, methyl cellulose, hydroxyethylmethyl cellulose, or sodium carboxymethyl cellulose. When present, a hydroxypropyl methyl cellulose can have a molecular weight ranging from 10,000 to 1,500,000. Examples of suitable, commercially available hydroxypropyl methylcellulose polymers include HPMC K100M, Methocel K100LV and Methocel K4M.

A specific class of gelling polymer of which one or more members may be used in the present dosage forms is carbomer polymers, which are polymers derived from acrylic acid (e.g., acrylic acid homopolymers) and cross-linked with polyalcohol allyl ethers, e.g., crosslinked with polyalkenyl ethers of pentaerythritol or sucrose. Carbomer polymers are hydrophilic and are not substantially soluble in water. Rather, these polymers swell when dispersed in water forming a colloidal, mucilage-like dispersion. Carboxyl groups provided by acrylic acid residues of the polymer backbone are responsible for certain behavior of the polymers. Particles of this polymer can be viewed as a network structure of polymer chains interconnected by crosslinks. The structure can swell in water by up to one thousand times of an original (dry) volume (and ten times an original diameter of polymer particles) to form a gel when exposed to a pH environment above 4-6. The pKa of these polymers can be 6±0.5. Accordingly, carboxy late groups pendant from the polymer backbone can ionize at a pH above 6, producing a repulsion between the negatively-charged particles, which adds to the swelling of the polymer if exposed to solvent at this pH range.

For this reason, the presently disclosed dosage forms can include a pH adjuster in an amount and location within the dosage form to raise the pH of a carbomer polymer to at least 6, to substantially neutralize the carboxy late groups. Exemplary types and amounts of pH adjusters are discussed more fully, infra.

Carbomer polymers are often referred to in the art using alternative terminology such as, for example, carbomer homopolymer, acrylic acid polymers, carbomer, carboxy polymethylene, carboxyvinyl polymer, polyacrylic acid, and poly(acrylic acid), The USP-NF lists three umbrella monographs i.e. for "carbomer copolymer," for "carbomer homopolymer," and for "carbomer interpolymer."

Certain carbomer polymers that may be useful as a gelling polymer can have an average equivalent weight of 76 per carboxyl group. Examples of suitable commercially available carbomers include Carbopol® 934, 934P NF, Carbopol® 974P NF and Carbopol® 971P NF, Carbopol® 940, and Carbopol® 941, Carbopol® 71G, commercially available from Lubrizol. Examples of such polymers are described in U.S. Pat. Nos. 2,798,053 and 2,909,462, the entireties of which are incorporated herein by reference. Theoretical molecular weight ranges of Carbopol® products are in a range from 700,000 to 3 billion, theoretical estimation. For dosage forms as described herein, a gelling polymer (e.g., Carbopol®) can have a molecular weight and viscosity-increasing performance that will reduce or substantially inhibit an ability of an abuser to extract API from a combination of dosage form and a small volume of solvent, as described, while also being capable of being processed into a compressed dosage form.

A gelling polymer can also be characterized by viscosity of a solution prepared from the gelling polymer. Product information for commercially available Carbopol® polymers reports that viscosities of different Carbopol® polymers are as follows:

| Type of Carbomer | Viscosity specified (cP) |
|---|---|
| Carbomer Homopolymer Type A (compendial name for Carbopol ® 71G, Carbopol ® 971P and Carbopol ® 981) | 4,000-11,000 |
| Carbomer Homopolymer Type B (compendial name for Carbopol ® 934P, and Carbopol ® 934) | 25,000-45,000 |
| Carbomer Homopolymer Type C (compendial name for Carbopol ® 980) | 40,000-60,000 |

(Type A and Type B viscosities measured using a Brookfield RVT, 20 rpm, neutralized to pH 7.3-7.8, 0.5 weight percent mucilage, spindle #5.)

A further exemplary gelling polymer is the class of xanthan gum polymers, which includes natural polymers useful as hydrocolloids, and derived from fermentation of a carbohydrate. A molecular weight of a Xanthan gum may be approximately 1,000,000. Xanthan gum has been shown to provide particularly useful extraction resistance in a dosage form as described, and therefore may be preferred in dosage forms as described, especially if present in an amount of at least 2 or 3 weight percent based on a total weight of a dosage form.

Without limiting the scope of useful gelling polymers to any specific type or molecular weight, examples of useful gelling polymers, and useful respective molecular weights, are shown below.

| Gelling Polymer | Weight Average Molecular Weight |
|---|---|
| Carbomer | 700,000 to 3 billion (estimated) |
| HPMC 2910 K types | 164,000-1,200,000 |
| HPMC 2910 E types | 20,000-746,000 |
| hydroxyethylcellulose | 90,000-1,300,000 |
| ethylcellulose | 75,000-215,000 |
| carboxymethylcellulose | 49,000-725,000 |
| sodium carboxymethylcellulose | 49,000-725,000 |
| povidone | 4,000-1,300,000 |
| copovidone | 47,000 |
| hydroxypropyl cellulose | 40,000-1,150,000 |
| xanthan gum | 1,000,000 |
| polyethylene oxide | Average molecular wt: 100,000-7,000,000 |

The present dosage forms may optionally include another abuse deterrent feature in the form of a wax, such as a wax/fat material, e.g., as described in U.S. Pat. No. 8,445,018, the entirety of which is incorporated herein by reference. The wax can be a solid wax material that is present in the dosage form at a location that inhibits an abuser from crushing, grinding, or otherwise forming the dosage form into a ground powder that might be abused by a nasal insufflation mode, or from which active pharmaceutical agent can be easily accessed and removed such as by dissolution or extraction using a solvent.

A wax may be present in the dosage form at a location and in an amount to also not interfere with desired uptake of the active pharmaceutical ingredient by a patient upon oral ingestion, in an immediate release dosage form. An exemplary location is at a core of a core-shell particle, especially a core that also contains gelling polymer and that either may or may not contain active pharmaceutical ingredient. In one embodiment, a wax is provided in the core of core-shell particles in the present dosage forms, along with a gelling polymer, in the absence of esketamine in the core. Wax located at a core of a particle (e.g., a core-shell particle) that also includes active pharmaceutical ingredient (e.g., at a layer covering the core, or within the core) will become mixed with the active pharmaceutical ingredient upon crushing or grinding, etc., of the particle. In one embodiment, a wax is provided in the core of core-shell particles in the present dosage forms, along with a gelling polymer, in the absence of esketamine in the core. Wax that is located at a core of such a particle (e.g., a core-shell particle) wherein the core does not contain API will also become mixed with the API (e.g., API present in API-containing core-shell particles that are also present in the dosage form) upon destructive manipulation (e.g., crushing or grinding) of the dosage form. When the wax is mixed with the active pharmaceutical ingredient, the active ingredient is inhibited or prevented from becoming thereafter dissolved in a solvent such as water, or otherwise efficiently accessed by an abuser.

A core (uncoated) of a core-shell particle can contain any useful amount of wax, up to and including 100 percent wax, e.g., from 0.1 to 85 weight percent wax based on the total weight of the core, such as 5 to 80, 10 to 70, 15 to 60, 20 to 50, 20-40, or 20-30, or in an amount of about 5, 10, 15, 20, 21, 22, 23, 24, 25, 26, 27, 28, 29, 30, 31, 32, 33, 34, 35, 36, 37, 38, 39, 40, 45, 50, 55, 60, 65, 70, 75, or 80 weight percent wax, based on the total weight of the core.

The wax may be a wax (e.g., fat) material that is generally hydrophobic and that may be either solid or liquid at room temperature, preferably solid at room temperature (25 degrees Celsius). Generally useful fats include those hydrophobic materials that are fatty acid-based compounds generally having a hydrophilic/lipophilic balance (HLB) of 6 or less, more preferably 4 or less, and most preferably 2 or less. A fat can have any melting temperature, with preferred fats being solid at room temperature and having a melting point that is at least 30 degrees Celsius, e.g., at least 40 degrees Celsius, e.g., at least 50 degrees Celsius. Useful fats include fatty acids and fatty esters that may be substituted or unsubstituted, saturated or unsaturated, and that have a chain length of at least 10, 12, or 14 carbons. The esters may include a fatty acid group bound to any of an alcohol, glycol, or glycerol. With regard to glycercols, for example, mono-, di-, and tri-fatty substituted glycerols can be useful as well as mixtures thereof.

Suitable wax ingredients include fatty acid esters, glycerol fatty acid esters, fatty glyceride derivatives, waves, and fatty alcohols such as, for example, glycerol behenate (also referred to as glyceryl behenate, glycerin behenate, or glycerol docosanoate) (available commercially as COMPRITOL®), glycerol palmitostearate (PRECIROL®), glycerol monostearate, stearoyl macroglycerides (GELUCIRE® 50/13). Other waxes more generally include insect and animal waves, vegetable waxes, mineral waxes, petroleum waxes, and synthetic waxes; particularly examples include beeswax, carnauba wax, candelilla wax, montan wax, ouricury wax, rice-bran wax, jojoba wax, microcrystalline wax, cetyl ester wax, cetyl alcohol, anionic emulsifying wax, nonionic emulsifying wax and paraffin wax.

The dosage form may optionally include another component contributing to abuse deterrence in the form of a filler or binder material provided in a manner to compromise abuse practices wherein an abuser crushes, grinds, or otherwise forms the dosage form into a ground powder that might be abused by nasal insufflation, or from which active pharmaceutical agent can be easily accessed and removed such as by dissolution or extraction using a solvent.

The binder or filler may be present in the dosage form at a location and in an amount to not interfere with desired uptake of the active pharmaceutical ingredient by a patient upon oral ingestion, in an immediate release dosage form. An exemplary location is at a core of a core-shell particle. Suitable filler or binder located at a core of a core-shell particle that also includes active pharmaceutical ingredient (such as in a layer covering the core, or within the core) will become mixed with the active pharmaceutical ingredient upon destructive manipulation (e.g., crushing or grinding) of the particle. As discussed previously, the dosage form may also include core shell particles that do not contain esketamine. A filler or binder that is located at a core of such a particle that does not contain API will also become mixed with the API (e.g., API present in API-containing core shell particles that are also present in the dosage form) upon manipulation (e.g., crushing or grinding) of the dosage form. When a filler or binder is mixed with the active pharmaceutical ingredient, the active pharmaceutical ingredient is inhibited or prevented from becoming thereafter dissolved in a solvent such as water or otherwise efficiently accessed by an abuser.

When present within the core of a core-shell particle of the present dosage forms, filler or binder may be present in any useful amount, up to and including 100 percent filler or binder (singly or in combination) in a core of a core-shell particle. For example, filler or binder may be present in the core of a core-shell particle in an amount of from 5 to 95 weight percent filler or binder based on total weight of the core, such as from 5 to 70, 5 to 50, 7 to 40, 10 to 30, 10 to 20, 10 to 17, 12 to 17, or 13 to 16 weight percent, or in an amount of about 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, or 80 percent by weight based on the total weight of the core. Examples of cores that contain high levels of filler include spherical particles that contain 100 percent sugar, and spherical particles that contain 100 percent microcrystalline cellulose. Inert spherical filler products such as these, having useful particle sizes, are commercially available under the trade name Celphere R, and under the trade name Suglets® (sugar spheres, also containing starch), including as follows: CELPHERE SCP-100 (Particle size (μm) 75-212); CELPHERE SCP-102 (Particle size (μm) 106-212); CELPHERE SCP-203 (Particle size (μm) 150-300); CELPHERE SCP-305 (Particle size (μm) 300-500); CELPHERE SCP-507 (Particle size (μm) 500-710); CELPHERE SCP-708 (Particle size (μm) 710-850). The particle sizes of these can be considered to be useful for any core as described herein, prepared of any single filler, gelling polymer, binder, any combination thereof, or any single or combination of materials combined with API.

Another abuse deterrent feature that can be included in a dosage form as provided herein is a film layer or coating as part of the core-shell particles that is located over and surrounds the portion of the particles that contains the active pharmaceutical ingredient. When the dosage forms contain core-shell particles that do not contain an API, the film layer may be present as a layer or coating on such core-shell particles, as well. The film layer can be any film layer capable of being applied as a partial or complete film layer to core-shell particles, and to surround API (where present).

The film layer may be prepared from, and will include any pharmaceutically acceptable film forming polymer material, such as one or more of a binder (e.g. as described herein, such as hydroxypropyl cellulose, poly(methyl methacrylates), ethyl cellulose, hydroxypropyl methyl cellulose, hydroxyl methyl cellulose, polyvinyl alcohol, and the like), a solvent-resistant layer, and a pH-sensitive layer (also sometimes referred to as a reverse enteric material or layer), e.g., Eudragit® E 100. The film layer may include any one of these materials alone (e.g., a film layer may include 100 percent of a single one of these types of materials), or a film layer may include a combination of two or more of these types of materials.

A solvent-resistant layer is a film layer that retards or prevents release of a drug in a solvent (e.g., one or more of water, ethanol, and methanol) while still allowing the drug to release normally in a gastrointestinal tract when ingested as an immediate release oral dosage form. This type of abuse deterrent feature, e.g., solvent-resistant film, can inhibit access to an API of a dosage form by preventing or impeding an abuser from dissolving an intact or powdered dosage form in a solvent type that is often used by an abuser (e.g., water, ethanol, methanol). At the same time, the solvent-resistant film can dissolve in a human gastrointestinal tract with sufficient rapidity to allow for an immediate release profile. As an abuse deterrent feature this type of solvent-resistant film covers and encloses API of a core-shell particle and acts as a film barrier or retardant to prevent or retard access to the API by use of solvent.

A solvent-resistant film is one that does not readily or immediately dissolve in a small volume of a solvent of the type often used by an abuser to dissolve an API, such as any one of water or a $C_1$-$C_4$ alcohol such as ethanol or methanol. A "small volume" refers to an amount of such a solvent that can contain an amount of dissolved API that is sufficiently concentrated to be useful to an abuser to realize the intended biological effect of the drug abuse, and that is also capable of being administered for abuse of the API, e.g., a volume that can contain an amount (concentration) of API that is effective to achieve a desired "high" if administered by injection or nasal insufflation, the volume also being sufficiently small to allow the volume to be administered by injection or nasal insufflation. For a dosage form to be useful for abuse as such, an API in the dosage form must be capable of being accessed and dissolved at sufficient concentration by an abuser without undue complication, into a "small volume" of solvent, which is a volume that can be administered by injection or by nasal insufflation. Generally, a "small volume" of solvent means 50 milliliters or less, or 20 milliliters or less, or 10 milliliters or less, or 5 milliliters or less (volumes which could be injected or used for nasal insufflation).

A solvent-resistant film layer can be a film placed on a core-shell particle that is difficult to dissolve in a "small volume" of water or a $C_1$-$C_4$ alcohol such as ethanol or methanol, e.g., that does not immediately dissolve in one or more of water or any one of a $C_1$-$C_4$ alcohol, such as methanol or ethanol. The solvent-resistant film thereby retards or prevents an abuser from accessing an API portion of a core-shell particle if the core-shell particle is placed in one of these solvents. The solvent-resistant film need not be completely or substantially insoluble in any one of these solvents, or in all of the solvents, and it must be capable of allowing the API to be accessed with sufficient rapidity, in a gastrointestinal tract, for the dosage form to be useful as an immediate release dosage form.

A particular example of a solvent-resistant film is a film that exhibits solubility properties that depend on the pH of a solvent. An example of a solvent-resistant film may be a film that is substantially or completely insoluble at a pH that is greater than a pH condition of a human stomach, and that is sufficiently soluble at a pH condition of a stomach (and gastrointestinal tract) to allow the film to dissolve and release API with sufficient rapidity that the dosage form can be useful as an immediate release oral dosage form. A pH-sensitive layer is a type of solvent-resistant film, and can be disposed in a dosage form to surround an active pharmaceutical ingredient and inhibit or prevent access to and dissolution of the active pharmaceutical ingredient in a solvent outside of a stomach (e.g., at a neutral pH environment), while still allowing the active pharmaceutical ingredient to be efficiently released from an immediate release dosage form at a lower pH environment of a user's stomach. This type of abuse deterrent feature can prevent or significantly impede an abuser's access to an active pharmaceutical agent of a dosage form (e.g., at the core of a core-shell particle or in a layer disposed on the core, or in both the core and the layer disposed on the core) by use of a solvent that is outside of a stomach and that does not have a relatively acidic pH, such as water or a $C_1$-$C_4$ alcohol such as ethanol or methanol, or a mixture thereof, having a pH that is higher than a pH found in a human stomach, for example a pH greater than 4, greater than 5, or greater than 5.5, or greater than 6.

A pH-sensitive layer may be useful as a solvent-resistant film, placed in a dosage form as a layer of a core-shell particle to surround, cover, or enclose a portion of the core-shell particle that contains active pharmaceutical ingredient. For example, in a core-shell particle, an active pharmaceutical ingredient may be located at a core or in a layer outside of an uncoated or coated core, and a solvent-resistant film in the form of a pH-sensitive layer may be disposed as a separate layer surrounding or covering the portion of the core-shell particle that contains the active pharmaceutical ingredient. The pH-sensitive layer may be in direct contact with (adjacent to) a core or a layer that includes active pharmaceutical ingredient. Alternatively, a core-shell particle may include one or more intermediate layers between a pH-sensitive layer and a core or layer that includes active pharmaceutical ingredient. In addition, a pH-sensitive layer may be included in the dosage form as a layer of a core-shell particle that does not contain either an API layer or any API.

A useful pH-sensitive layer may include a polymer or other material that can be placed as a layer of a particle as described herein, such as to cover a more inner layer or core that contains active pharmaceutical ingredient, to form a pH-sensitive film surrounding or covering active pharmaceutical ingredient. The pH-sensitive film can be solubilized by exposure to a liquid that exhibits a pH that may be present in a stomach of a user of the dosage form, such as a pH below 6 or below 5.5. To function as an abuse-deterrent feature, i.e., to inhibit or prevent efficient access to the active pharmaceutical ingredient by exposing the dosage form (optionally ground or powdered) to an easily-available solvent, the pH-sensitive layer can contain polymer that is not easily or substantially soluble at a pH that is higher than a pH found in a human stomach, e.g., a pH greater than 6. By being insoluble at a pH greater than 6, the pH-sensitive polymer will not dissolve in many solvents that are readily available and commonly used by attempted abusers to extract a water-soluble drug from a dosage form. Examples of such solvents include water, ethanol, and methanol.

Examples of pH-sensitive polymers that may be used in a pH-sensitive layer in the present dosage forms include the class of reverse enteric polymers that contain cationic-functional groups and that exhibit pH-dependent solubility as described herein. Examples include polymers that contain basic functional groups, such as amino groups, and that exhibit solubility at pH conditions found in a (human) stomach but not at relatively higher pH conditions, e.g., not above a pH of 4, 5, or 5.5, or not above a pH of 6. More specific examples of such pH-sensitive polymers include copolymers of dimethyl aminoethyl methacrylates, and neutral methacrylic acid esters; e.g., dimethyl aminoethyl methacrylate, butyl methacrylates, and methyl methacrylates, such as at a ratio of 2:1:1. Examples of such polymers are commercially available under the trade name Eudragit® E 100, Eudragit® E PO, Eudragit® E 12.5, and similar amino-functional pH-sensitive polymers. A preferred pH-sensitive polymer is the polymer Eudragit E 100, but any polymer that is sufficiently hydrophilic at a low pH and hydrophobic at a higher pH to exhibit pH-dependent solubility, may also be effective if otherwise acceptable for use in a pharmaceutical dosage form, for example, as a non-toxic ingredient of an oral dosage form. Reverse enteric compositions are also described in EP 1694724 B1, titled "pH Sensitive Polymer and Process for Preparation Thereof", incorporated herein by reference.

When present in a coating layer of a core-shell particle, whether that particle contains active pharmaceutical ingredient or not, a solvent-resistant film layer may be present at any amount useful as an abuse deterrent feature, such as in a range from 0.1 to 90 weight percent of a total weight of a core-shell particle, e.g., from 3 to 50, 10 to 50, 20 to 50, 25 to 45, 25 to 40, 30 to 40, or 30 to 35 weight percent, or in an amount of about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weight percent, relative to the total weight of the core-shell particle. More generally, a useful amount solvent-resistant film layer or polymer in a dosage form may be in a range from 1 to 50 weight percent solvent-resistant film layer or polymer based on a total weight of a dosage form, e.g., from 2 to 30 or from 3 to 15 weight percent solvent-resistant polymer based on total weight dosage form.

A dosage form as presently described further includes a disintegrant, which functions to cause the dosage form to expand and break up during use, e.g., under the conditions within a human stomach, to allow the active pharmaceutical ingredient of the dosage form to be released in a manner to achieve an immediate release profile. Disintegrants are known ingredients of pharmaceutical dosage forms, with various examples being known and commercially available. Examples of disintegrants include compositions of or containing sodium starch glycolate, starch (e.g., maize starch, potato starch, rice starch, tapioca starch, wheat starch, corn starch and pregelatinized starch), croscarmellose sodium, crospovidone (crosslinked polyvinyl N-pyrrolidone or PVP) (polyplasdone XL-10), sodium starch glycolate (EXPLOTAB® or PRIMOJEL®), any combination of the foregoing, and other pharmaceutically acceptable materials formed into particles having a particle size, density, and other characteristics that are suitable to allow processing of the disintegrant into a useful immediate release dosage form.

The disintegrant can be present in an immediate release dosage form at any location that allows the disintegrant to function as desired, to expand within the intact dosage form, upon ingestion, to cause the ingested dosage form to break apart and allow for desired immediate release of active pharmaceutical ingredient from the dosage form, in a stomach. An exemplary location for the disintegrant can be within the matrix, where it can function as an excipient used to contain the core-shell particles in a dosage form such as a compressed tablet or capsule.

When included as an excipient of a dosage form, a disintegrant may be present in an amount useful to achieve immediate release of an API of a dosage form. For example, the disintegrant may be present in an amount of 0.5 to 50, 5 to 40, 10 to 35, 15 to 30, 15 to 25, 17 to 22, or 19 to 21 weight percent, or in an amount of about 5, 10, 12, 14, 16, 18, 19, 20, 21, 22, 24, 26, 28, 30, 35, 40, 45, or 50 weight percent, based on a total weight of the dosage form. The amount of disintegrant in the matrix of a dosage form can be consistent with these amounts. For example, disintegrant can be included in a matrix (e.g., total of a dosage form that is other than the core-shell particles) of a dosage form in an amount in a range from 0.5 to 50 weight percent disintegrant based on a total weight of the matrix, for example, 1 to 30 weight percent disintegrant based on total weight matrix.

The presently disclosed dosage forms can also include a pH adjuster. A pH adjuster can be included at a location of the dosage form to affect pH at a specific location of the dosage form that is only a portion of a total dosage form. As an example, a pH adjuster in the form of a base may be included at a location of a gelling polymer that contains acid functionalities, to neutralize the acid functionalities. Suitable agents that can act as a pH adjuster include, for example, phosphate buffering agents such as, disodium hydrogen phosphate, sodium dihydrogen phosphate and the equivalent potassium salts; carbonate or bicarbonate salts, such as sodium bicarbonate, sodium carbonate, potassium bicarbonate, potassium carbonate, magnesium carbonate and calcium carbonate; hydroxide bases such as, sodium hydroxide, potassium hydroxide, ammonium hydroxide; and amine bases such as, triethanolamine, tromethamine, aminomethyl propanol, and tetrahydroxypropyl ethylenediamine.

The amount of pH-adjuster included at the location of the gelling polymer can be an amount effective to neutralize the acid functionalities of the gelling polymer at that location. More specifically, a component of a dosage form as described that includes an acid-functional gelling polymer such as a carbomer may include a base in an amount and location to neutralize the acid functionalities of that polymer. The pH-adjuster can be located at a location effective to cause such neutralization, e.g., at the location of the dosage form that contains the acid-functional gelling polymer, for example at a core of a core-shell particle or as part of a matrix.

According to some embodiments, the pH adjuster is in the present dosage forms in an amount that is from about 0.5 to about 5 percent by weight, from about 1 to about 4 percent by weight, from about 1.5 to about 4 percent by weight, from about 2 to about 3 percent by weight, or in an amount of about 0.5, 1, 1.5, 2, 2.5, 3, 3.5, 4, 4.5, or 5 percent by weight, based on the total weight of the dosage form.

According to some embodiments, the pH adjuster is in the present dosage forms in an amount that is from about 0.5 to about 2 percent by weight, from about 1 to about 2 percent by weight, from about 1.5 to about 2 percent by weight, or in an amount of about 0.5, 1, 1.5, or 2 percent by weight, based on the total weight of the dosage form.

In one embodiment, the pH adjuster is in the dosage form in an amount of no more than 2 percent by weight. As used throughout the present disclosure, "the pH adjuster is in the dosage form in an amount of no more than 2 percent by weight" includes those embodiments that do not include a pH adjuster, i.e., wherein the pH adjuster is 0 percent by weight. In one embodiment, the pH adjuster is in the dosage form in an amount of no more than 2 percent, no more than 1.9 percent, no more than 1.8 percent, no more than 1.7 percent, no more than 1.6 percent, no more than 1.5 percent, no more than 1.4 percent, no more than 1.3 percent, no more than 1.2 percent, no more than 1.1 percent, no more than 1 percent, no more than 0.9 percent, no more than 0.8 percent, no more than 0.7 percent, no more than 0.6 percent, no more than 0.6 percent, no more than 0.5 percent, no more than 0.4 percent, no more than 0.3 percent, no more than 0.2 percent, or no more than 0.1 percent by weight.

In one embodiment, the present dosage form comprises a pH adjuster in an amount that is less than 0.1 percent by weight.

In one embodiment, the present dosage form does not comprise a pH adjuster.

As noted above, it has presently been discovered that specific ratios of gelling polymer, particularly carbomer gelling polymer, to pH adjusting compound, within the matrix of the present dosage forms can be critical for allowing the dosage form, when administered in supratherapeutic doses, to produce a gel having superior physical characteristics for purposes of thwarting abuse of esketamine from the dosage forms. In one embodiment, the dosage form includes a matrix that includes a carbomer gelling polymer and a pH adjuster that are present in a ratio of 2:2 weight percent, based on the total weight of the dosage form. For example, the dosage form can include a matrix that includes a carbomer gelling polymer and sodium bicarbonate pH adjuster that are present in a ratio of 2:2 weight percent, based on the total weight of the dosage form. As described more fully in the Examples that follow, the gels that result from such dosage forms when administered in supratherapeutic doses possess traits that are optimal for functioning as an abuse deterrent feature, as compared with gels that are formed following administration of previous dosage forms in supratherapeutic doses.

For example, with respect to the dosage forms that contain a carbomer gelling polymer and sodium bicarbonate pH adjuster that are present in a ratio of 2:2 weight percent, based on the total weight of the dosage form, supratherapeutic doses of such dosage forms can produce a gel in 15 minutes or less, such as in 15, 14, 13, 12, 11, 10, 9, 8, 7, 6, 5, 4, 3, 2, or 1 minute following exposure to an aqueous medium comprising 0.025 N HCl and 70 mM NaCl at 37° C. The supratherapeutic dose may be, for example, 15, 14, 13, 12, 11, 10, 9, or 8 individual dosage units.

In certain embodiments, the dosage forms are such that when a dual screen apparatus with a top screen and a bottom screen is used to extract at least a portion of a gel that is formed in an aqueous medium comprising 0.025 N HCl and 70 mM NaCl at 37° C. from a supratherapeutic dose of the dosage forms from the medium, a first quantity of the gel adheres to a lower surface of the top screen of the apparatus, and a second quantity of the gel adheres to a upper surface of the bottom screen of the apparatus, and the vertical thickness of the second quantity is at least twice the vertical thickness of the first quantity.

Figure 9:
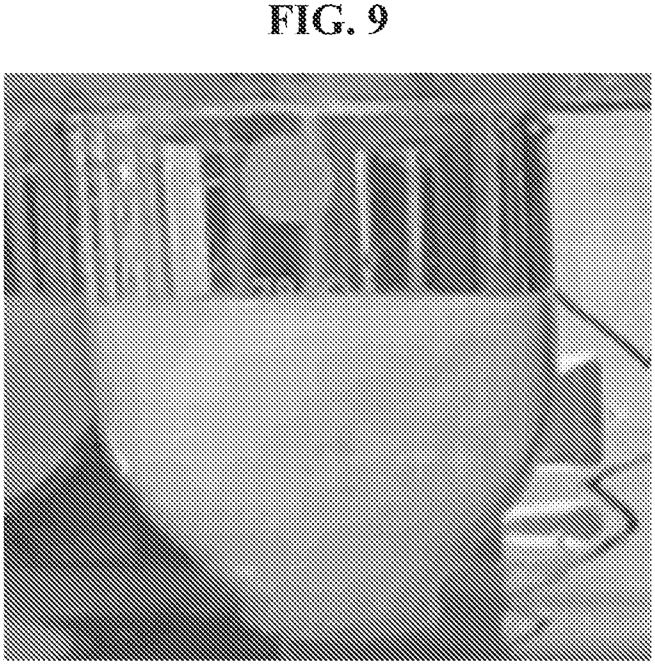
FIG. 9 provides an image of a gel resulting from a supratherapeutic dose of inventive dosage forms, suspended in a test medium.

The gels that are formed in an aqueous medium comprising 0.025 N HCl and 70 mM NaCl at 37° C. from a supratherapeutic dose of the present dosage forms may also be characterized as being substantially uniformly dispersed with the medium. This means, for example, that the gel that is formed within the medium does not include a greater concentration of gel within any particular portion of the medium, such as within the upper portion or within the lower portion of the medium. In other words, the concentration of gel within the medium is substantially homogenous upon visual inspection within all portions of the medium, including within the upper portion of the medium and within the lower portion of the medium, respectively. A gel that is substantially uniformly dispersed within the medium in which it is formed may also be characterized by an absence of portions of gel that are interspersed with portions of medium that do not contain gel. This can be described as the condition wherein visually readily apparent clumps of gel are suspended in the medium. As described below, FIG. 9 illustrates the characteristic of a gel formed from dosage forms as disclosed herein of being substantially uniformly dispersed.

The above-described characteristics are indicative of the fact that the gels that are formed from the present dosage forms in a medium as described herein are thick and viscous, with a uniform dispersion within the medium. These attributes, in turn, enhance the ability of the present dosage forms to resist uptake by or injection from a needle of a hypodermic syringe when combined with a solvent in supra-therapeutic doses, and also or alternatively to reduce the overall amount of drug that is extractable with a solvent by entrapping the drug in a gel matrix.

A dosage form as described can also include any of various known and conventional pharmaceutical excipients that may be useful to achieve desired processing and performance properties of an immediate release dosage form. These excipients may include disintegrants, fillers, binders, lubricants, glidants, and coloring agents, and can be included in core-shell particles or in a matrix (e.g., compressed matrix) of a tablet or capsule. A more detailed description of pharmaceutical excipients that may also be included in the tablets of the present invention can be found in The Handbook of Pharmaceutical Excipients, 5th ed. (2006). As noted above, one or more of these excipients, such as the binder, filler, or both, may contribute to abuse deterrence in a manner to compromise abuse practices wherein an abuser crushes, grinds, or otherwise forms the dosage form into a ground powder that might be abused by nasal insufflation, or from which active pharmaceutical agent can be easily accessed and removed such as by dissolution or extraction using a solvent.

Examples of fillers that may be useful in an immediate release dosage form as described include lactose, starch, dextrose, sucrose, fructose, maltose, mannitol, sorbitol, kaolin, microcrystalline cellulose, powdered cellulose, calcium sulfate, calcium phosphate, dicalcium phosphate, lactitol or any combination of the foregoing. As compared to non-filler ingredients such as gelling polymers, a filler will have a molecular weight that does not result in a substantial viscosity increase or formation of a gel as described herein for a gelling polymer, if combined with a solvent such as water.

A filler may be present in any portion of a dosage form as described, including a core-shell particle; the filler may be present in a core, in a layer containing an active pharmaceutical ingredient that is disposed on the core, in a solvent resistant film, in the matrix, or in two or more of these portions of the dosage form. The filler may be present at any one or more of these portions of a dosage form in an amount to provide desired processing or functional properties of a portion of the dosage form and of the entire dosage form. The amount of total filler in a dosage form can also be as desired to provide desired functionality, including an immediate release profile, for example, in an amount of greater than 0 to 80, 5 to 50, 5 to 40, 10 to 30, 12 to 25, or 12 to 15 weight percent, or in an amount of about 2, 4, 5, 7, 9, 10, 12, 13, 14, 15, 16, 17, 18, 19, 20, 25, 30, 35, or 40 weight percent filler based upon the total weight of the dosage form.

Examples of binders that may be included in a dosage form as described herein include polymeric material such as alginic acid, sodium carboxymethylcellulose, microcrystalline cellulose, dextrin, ethylcellulose, gelatin, starch, pregelatinized starch, polyvinyl alcohol, polyethylene oxide, polyvinylpyrrolidone, polyacrylamides, polyvinyloxoazolidone, polyvinylalcohols, methylcellulose, hydroxypropyl cellulose, hydroxymethyl cellulose and any combination of two or more of these. A binder may be a water-soluble material. As compared to non-binder ingredients such as a gelling polymer, a binder is of a molecular weight that does not result in formation of a gel or a highly viscous composition upon combining with a small volume of water. A binder can exhibit a relatively low molecular weight as compared to a gelling polymer, and a relatively lower viscosity (e.g., when measured in a 2% aqueous solution). Polymer useful as a binder may typically have a molecular weight of less than 50,000, e.g., less than 30,000, or less than 10,000.

A binder may be present in any portion of the present dosage forms, including in a core or a film or coating of a core-shell particle, or as part of an excipient mixture to contain or bind core-shells particles in a dosage form, i.e., within the matrix of a dosage form as described herein. Filler may be included in a core of a core-shell particle in combination with active pharmaceutical ingredient, gelling polymer or both; as part of an active pharmaceutical layer located over a core or another layer of a core-shell particle; as part of a solvent-resistant film; or, within an excipient mixture (matrix) useful to bind particles into a dosage form. A binder may be present at any one or more of these portions of an immediate release dosage form as described, in an amount to provide desired processing or functional properties in each portion of the dosage form and of the overall dosage form. The amount of total binder in a dosage form can also be as desired to provide desired functionality, including immediate release functionality. For example, a binder may be provided in an amount of about 0.1 to 40, 5 to 40, 10 to 30, 12 to 25, or 12 to 15 weight percent, or in an amount of about 2, 4, 5, 7, 9, 10, 12, 13, 14, 15, 16, 17, 18, 19, 20, 25, 30, 35, or 40 weight percent binder based upon the total weight of the dosage form.

Examples of lubricants include inorganic materials such as talc (a hydrated magnesium silicate; polymers, such as, PEG 4000; fatty acids, such as stearic acid; fatty acid esters, such as glyceride esters (e.g., glyceryl monostearate, glyceryl tribehenate, and glyceryl dibehenate); sugar esters (e.g., sorbitan monostearate and sucrose monopalmitate); glyceryl dibehenate (Compritol® 888 ATO); and metal salts of fatty acids (e.g., magnesium stearate, calcium stearate, and zinc stearate). Accordingly, commonly used lubricants include talc, glyceryl monostearates, calcium stearate, magnesium stearate, stearic acid, glyceryl behenate, polyethylene glycol, poloxamer and combinations of the foregoing. A lubricant may be included in an immediate release dosage form as described, in any useful amount, such as an amount of about 0.1 to 10 weight percent lubricant based on a total weight of a dosage form, e.g., from 0.2 to 7, 0.3 to 5, 0.5 to 3, 0.7 to 2, or 0.9 to 1.5 weight percent, or in an amount of about 0.1, 0.2, 0.3, 0.4, 0.5, 0.6, 0.7, 0.8, 0.9, 1, 2, 3, 4, or 5 weight percent, based on the total weight of the dosage form.

Examples of glidants include colloidal silicon dioxide, untreated fumed silica (e.g., as available under the trade name Cab-O-Sil®), and crystalline or fused quartz. Glidant may be included in an immediate release dosage form as described, in any useful amount. For example, a glidant may be included in an amount of 0.05 to 5, 0.08 to 3, 0.1 to 2, 0.15 to 1.5, 0.15 to 1, or 0.2 to 0.5 weight percent, or in an amount of about 0.01, 0.03, 0.05, 0.1, 0.13, 0.15, 0.17, 0.2, 0.22, 0.25, 0.27, 0.3, 0.35, 0.4, 0.5, 0.7, 0.9, 1.0, 1.2, 1.4, 1.5, 1.6, 1.8, or 2 percent by weight, based on the total weight of the dosage form.

Examples of coloring agents include FD&C-type dyes and lakes, fruit and vegetable extracts, titanium dioxide, iron oxides and mixtures thereof. A coloring agent may be incorporated into a dosage form by blending (e.g., co-milling and blending) the coloring agent with any other ingredient. Alternately, coloring agent may be applied to an outer surface of a dosage form.

Esketamine, alone or in combination with one or more other active pharmaceutical ingredients, are included in the immediate release dosage forms as described herein. The esketamine may be present in its free base form or as a salt. An exemplary esketamine salt is esketamine hydrochloride.

With abuse deterrent features as described herein, some being operative based on specific structural or compositional features of a core-shell particle, the esketamine can be located in the dosage form at a location to cause the API to be subject to abuse deterrent features of the core-shell particles, e.g., at a core or inner layer of a core-shell particle.

The amount of esketamine in the dosage forms disclosed herein can be any useful amount, as is known and as may be found in relevant literature. For example, typical therapeutic amounts of esketamine are 5 mg, 10 mg, 20 mg, 30 mg, 40 mg. 50 mg, 60 mg, 70 mg. 80 mg, 90 mg, or 100 mg. Often, when processed into a suitable immediate release dosage form, the esketamine can be present in such dosage form in an amount normally prescribed, typically 0.5 to 25 percent on a dry weight basis, based on the total weight of the dosage form. In other embodiments, a dosage form contains any appropriate amount of esketamine to provide a therapeutic effect. When present in the core-shell particles of the dosage forms, the amount of esketamine in a core-shell particle may be about 10 to about 40% by weight, based on the total weight of the core-shell particle. For example, the esketamine may be present in an amount of about 10 to 35, 12 to 35, or 15 to 35 weight percent, or in an amount of about 10, 11, 12, 13, 14, 15, 16, 17, 18, 19, 20, 21, 22, 23, 24, 25, 26, 27, 28, 29, 30, 31, 32, 33, 34, or 35 weight percent, based on the total weight of the core-shell particle.

The presently disclosed dosage forms can optionally include one or more additional active pharmaceutical ingredients of a type that is not commonly susceptible to abuse. These additional APIs may be any suitable or desired API, such as those in the class of non-steroidal analgesic drugs. The expression "non-steroidal analgesic drugs" as used herein refers to drugs that include those commonly referred to as non-steroidal anti-inflammatory drugs, or "NSAIDS," and acetaminophen, which is non-steroidal, but does not act via an inflammation mechanism. Accordingly, the term "non-steroidal analgesic drugs" would include acetaminophen, and also include NSAIDS such as aspirin, ibuprofen, and naproxen. The present dosage forms also exhibit immediate release properties with respect to these APIs that are not commonly subject to abuse. Such APIs can be present in the dosage form at any useful level, typically 0.5 to 25, e.g., 1 to 10 weight percent of the API on a dry weight basis, based on a total weight of the dosage form, e.g., at a level of or between 5, 25, 50, 75, 100, 125, 150, 175, 200, 300, 325, 500, 750 or up to or exceeding 1000 milligram (mg) per dosage form unit. As a general matter, the present dosage forms can contain an appropriate amount of an API that is not commonly subject to abuse in order to provide a therapeutic effect that is associated with such additional API.

The present dosage forms can include one or more of the described abuse deterrent features alone or in combination; e.g., one or more of gelling polymer as part of a core-shell particle (e.g., at a core of the core-shell particle); wax as part of a core-shell particle (e.g., at a core of the core-shell particle); binder or filler as part of a core-shell particle (e.g., at a core of the core-shell particle); a film layer that may optionally be a solvent-resistant film (e.g., pH-sensitive film) as part of a core-shell layer; or gelling polymer as a component of an excipient or binder (i.e., a matrix) used to hold core-shell particles together. With these abuse deterrent features, other types of known abuse deterrent features may not be necessary and may be specifically excluded from the present dosage forms. Thus, certain embodiments of the described dosage forms can specifically exclude any of the abuse deterrent features described herein.

As for additional abuse deterrent features, the present dosage forms can optionally include a nasal irritant to discourage or prevent abuse by nasal insufflation. The nasal irritant can be a mucous membrane irritant or nasal passageway irritant that, if inhaled through a nasal passageway when contained in a ground or powdered dosage form, can induce pain or irritation of the abuser's nasal passageway tissue. Examples include surfactants such as sodium lauryl sulfate, poloxamer, sorbitan monoesters, and glyceryl monooleates. Certain particular embodiments of dosage forms of the present description do not require, and can specifically exclude, nasal irritant agents such as those described above.

The present dosage forms can include an emetic agent, to cause vomiting. Certain particular embodiments of dosage forms of the present description do not require and can specifically exclude an emetic agent.

The present dosage forms can include an effervescent agent that acts as a deterrent to abuse by nasal insufflation. The effervescent includes an acidic component and a basic component that release a gas such as oxygen or carbon dioxide when combined in the presence of an aqueous media, such as upon nasal insufflation. See, e.g., WO 2013/077851, the entirety of which is incorporated herein by reference. The acid source may be, for example, citric acid, tartaric acid, malic acid, maleic acid, lactic acid, glycolic acid, ascorbic acid, fumaric acid, adipic acid, succinic acid, salts thereof, and combinations thereof. The base may be, for example, a carbonate or bicarbonate. Dosage forms of the present description do not require, and can specifically exclude, an effervescent agent in the form of an acid and a base that can combine to a gas such as oxygen or carbon dioxide.

In one exemplary embodiment, the present oral dosage forms represent compressed tablets and comprise (i) a first population of core-shell particles, each of the core-shell particles of the first population comprises a core that includes a gelling polymer that is hydroxypropylmethycellulose and a wax that is glyceryl behenate; an active pharmaceutical layer surrounding the core, the active pharmaceutical layer comprising esketamine; and at least one layer surrounding the active pharmaceutical layer, the at least one layer comprising a pH-sensitive film comprising Eudragit E 100; and, (ii) a matrix comprising a carbomer gelling polymer, and sodium bicarbonate, wherein the carbomer gelling polymer and sodium bicarbonate are present in said dosage form in a ratio by weight percentage of about 2:2 based on the total weight of the dosage form, and optionally one or more of a disintegrant, a filler, or a binder;

wherein the dosage form exhibits an immediate release profile of the esketamine when administered to a human in therapeutic doses, and an extended release profile of the esketamine when administered to a human in supratherapeutic doses.

In a further embodiment, the present oral dosage forms represent compressed tablets and comprise (i) a first population of core-shell particles, each of the core-shell particles of the first population comprises a core that includes a gelling polymer that is hydroxypropylmethycellulose and a wax that is glyceryl behenate; an active pharmaceutical layer surrounding the core, the active pharmaceutical layer comprising esketamine; and at least one layer surrounding the active pharmaceutical layer, the at least one layer comprising a pH-sensitive film comprising Eudragit E 100; and, (ii) a matrix comprising a carbomer gelling polymer, and sodium bicarbonate, wherein the carbomer gelling polymer and sodium bicarbonate are present in said dosage form in a ratio by weight percentage of about 2:2 based on the total weight of the dosage form, and optionally one or more of a disintegrant, a filler, a glidant, a lubricant, or a binder;

wherein the dosage form exhibits an immediate release profile of the esketamine when administered to a human in therapeutic doses, and an extended release profile of the esketamine when administered to a human in supratherapeutic doses In a further embodiment, the present oral dosage forms represent compressed tablets and comprise (i) a first population of core-shell particles, each of the core-shell particles of the first population comprises a core that includes a gelling polymer that is hydroxypropylmethycellulose and a wax that is glyceryl behenate; an active pharmaceutical layer surrounding the core, the active pharmaceutical layer comprising esketamine and hydroxypropylmethycellulose; and at least one layer surrounding the active pharmaceutical layer, the at least one layer comprising a pH-sensitive film comprising Eudragit E 100 and magnesium stearate; and, (ii) a matrix comprising crospovidone, mannitol, microcrystalline cellulose, silicon dioxide, magnesium stearate, a carbomer gelling polymer, and sodium bicarbonate, wherein the carbomer gelling polymer and sodium bicarbonate are present in said dosage form in a ratio by weight percentage of about 2:2 based on the total weight of the dosage form;

wherein the dosage form exhibits an immediate release profile of the esketamine when administered to a human in therapeutic doses, and an extended release profile of the esketamine when administered to a human in supratherapeutic doses.

In a further exemplary embodiment, the present oral dosage forms represent compressed tablets and comprise (i) a first population of core-shell particles, each of the core-shell particles of the first population comprises a core that includes a gelling polymer that is hydroxypropylmethycellulose and a wax that is glyceryl behenate; an active pharmaceutical layer surrounding the core, the active pharmaceutical layer comprising esketamine; and at least one layer surrounding the active pharmaceutical layer, the at least one layer comprising a pH-sensitive film comprising Eudragit E 100;

(ii) a second population of core-shell particles that do not include an active pharmaceutical layer;

and, (iii) a matrix comprising a disintegrant, a filler, a binder, a carbomer gelling polymer, and sodium bicarbonate, wherein the carbomer gelling polymer and sodium bicarbonate are present in said dosage form in a ratio by weight percentage of about 2:2 based on the total weight of the dosage form;

wherein the dosage form exhibits an immediate release profile of the esketamine when administered to a human in therapeutic doses, and an extended release profile of the esketamine when administered to a human in supratherapeutic doses.

In yet another embodiment, the present oral dosage forms represent compressed tablets and comprise (i) a first population of core-shell particles, each of the core-shell particles of the first population comprises a core that includes a gelling polymer that is hydroxypropylmethycellulose and a wax that is glyceryl behenate; an active pharmaceutical layer surrounding the core, the active pharmaceutical layer comprising esketamine and hydroxypropylmethycellulose; and at least one layer surrounding the active pharmaceutical layer, the at least one layer comprising a pH-sensitive film comprising Eudragit E 100 and magnesium stearate;

(ii) a second population of core-shell particles that do not include an active pharmaceutical layer; and, (iii) a matrix comprising crospovidone, mannitol, microcrystalline cellulose, silicon dioxide, magnesium stearate, a carbomer gelling polymer, and sodium bicarbonate, wherein the carbomer gelling polymer and sodium bicarbonate are present in said dosage form in a ratio by weight percentage of about 2:2 based on the total weight of the dosage form;

wherein the dosage form exhibits an immediate release profile of the esketamine when administered to a human in therapeutic doses, and an extended release profile of the esketamine when administered to a human in supratherapeutic doses.

In still another embodiment, the present oral dosage forms represent compressed tablets and comprise (i) a first population of core-shell particles, each of the core-shell particles of the first population comprises a core that includes a gelling polymer that is hydroxy propylmethycellulose and a wax that is glyceryl behenate; an active pharmaceutical layer surrounding the core, the active pharmaceutical layer comprising esketamine and hydroxypropylmethycellulose; and at least one layer surrounding the active pharmaceutical layer, the at least one layer comprising a pH-sensitive film comprising Eudragit E 100 and magnesium stearate;

(ii) a second population of core-shell particles that do not include an active pharmaceutical layer, wherein each of the core-shell particles of the second population comprises a core that includes a gelling polymer that is hydroxypropylmethycellulose and a wax that is glyceryl behenate, and a shell that includes a pH-sensitive film comprising Eudragit E 100 and magnesium stearate; and, (iii) a matrix comprising crospovidone, mannitol, microcrystalline cellulose, silicon dioxide, magnesium stearate, a carbomer gelling polymer, and sodium bicarbonate, wherein the carbomer gelling polymer and sodium bicarbonate are present in said dosage form in a ratio by weight percentage of about 2:2 based on the total weight of the dosage form;

wherein the dosage form exhibits an immediate release profile of the esketamine when administered to a human in therapeutic doses, and an extended release profile of the esketamine when administered to a human in supratherapeutic doses.

According to further embodiments, provided herein are abuse resistant oral dosage forms for the administration of esketamine to a subject comprising: (i) a first population of core-shell particles, each of the core-shell particles of the first population comprising a core, an active pharmaceutical layer surrounding the core, the active pharmaceutical layer comprising esketamine or a pharmaceutically acceptable salt thereof, and at least one layer surrounding the active pharmaceutical layer, the at least one layer comprising a pH-sensitive film comprising a pH-sensitive polymer that is insoluble in water at a pH greater than 5; and, (ii) a matrix comprising a carbomer gelling polymer and sodium bicarbonate, wherein the carbomer gelling polymer and sodium bicarbonate are present in a ratio by weight percentage of about 2:2 based on the total weight of the dosage form; wherein the dosage form exhibits an immediate release profile of esketamine having not less than 90% of the esketamine released in 60 minutes, wherein the release profile is evaluated by dissolution of the tablet in 300 mL of 0.1N HCl media using USP II apparatus at 50 RPM paddle speed and 37° C.; wherein the dosage form exhibits an immediate release profile of the esketamine when administered to a human in therapeutic doses, and an extended release profile of the esketamine when administered to a human in supratherapeutic doses, or wherein the dosage form exhibits abuse resistant properties when physically manipulated, or wherein the dosage form exhibits abuse resistant properties when physically manipulated and administered in a manner not consistent with oral dosing, or wherein the dosage form exhibits abuse resistant properties when administered in a manner intended to result in administration of the esketamine in a higher than therapeutic dose.

In accordance with some of these embodiments, when the dosage form is physically manipulated by crushing to form a population of particles, a relatively low proportion of the population comprises a subpopulation of particles having a particle size of less than 75 μm. For example, less than 25, 20, 19, 18, 17, 16, 15, 14, 13, 12, 11, 10, 9, 8, 7, 6, or 5 wt % of such particles can comprise a subpopulation of particles having a particle size of less than 75 μm. In some embodiments, 1, 2, 3, 4, 5, 6, 7, 8, 9, 10, 11, 12, 13, 14, 15, 16, 27, 18, 19, or 20% of the population of particles comprises a subpopulation of particles having a particle size of less than 75 μm.

As used throughout the present disclosure, "crushing" or "crushed" refers to a sample that has been physically manipulated by mechanical means thereby leading to the sample's partial or complete disintegration, wherein the manipulation takes place for a time period of up to about 90 seconds and wherein at the completion of the manipulation, less than 10% of the recovered sample has a particle size of >500 μm and, by weight, more than about 99% of the sample can be recovered.

In certain of these embodiments, when the dosage form is physically manipulated by crushing to form a population of particles, less than 40 wt. % (e.g., 0 wt % to 39.5 wt. %, 10 wt. % to 39.5 wt. %, 10 wt % to 30 wt. %, 10 wt % to 20 wt. %, about 39.5 wt. %, 39 wt. %, 38.5 wt. %, 38 wt. %, 37.5 wt. %, 37 wt. %, 36.5 wt. %, 36 wt. %, or 35.5 wt. %) of the population of particles comprises a subpopulation of particles having a particle size of less than 106 μm, and wherein said subpopulation contains less than 10 wt. % base equivalent (e.g., less than about 9.5 wt. %, 9 wt. %, 8.5 wt. %, 8 wt. %, 7.5 wt. %, 7 wt. %, 6.5 wt. %, 6 wt. %, 5.5 wt. %, 5 wt. %) of the esketamine of said dosage form. In some embodiments, when the dosage form is physically manipulated by crushing to form a population of particles, less than 35 wt. % (e.g., less than about 34.5, 34, 33.5, 33, 32.5, or 32 wt. %) comprises a subpopulation of particles having a particle size of 212-500 μm and containing less than 70 wt. % base equivalent (e.g., less than about 69, 68, 67, 66, 65, 64, 63, 62, 61, 60, 58, 55 or 50 wt. %) of the esketamine of said dosage form. In some embodiments, when the dosage form is physically manipulated by crushing to form a population of particles, less than 30 wt. % (e.g., less than about 29, 28, 27, 26, 25, 24, 22 or 20 wt. %) comprises a subpopulation of particles having a particle size of 106-212 μm and wherein the subpopulation of particles contains less than 20 wt. % base equivalent (e.g., less than about 19.5, 19, 18, 17, 16, 15, 14, 13, 12, 11, or 10 wt. %) of the esketamine of said dosage form.

In certain embodiments, the present dosage forms exhibit one or more of the abuse resistant properties when the dosage form is physically manipulated by crushing and subsequently heating prior to the administration in a manner not consistent with oral dosing or in a manner that would result in administration of the esketamine in a higher than therapeutic dose (e.g., higher than therapeutic $C_{max}$), if a control dosage form were similarly administered. As described more fully in the examples below, one or more of the abuse resistant properties of the present dosage forms remain effective to prevent successful attempts to administer the active ingredient in a dose that is not consistent with therapeutic use of the dosage form, even when subjected to physical manipulation (e.g., crushing) and subsequent heating, which otherwise represents a commonly used approach to defeat, for example, gelling properties of a dosage form. In certain embodiments, the heating comprises subjecting the physically manipulated (e.g., crushed) dosage form to a temperature of about 200° C.-300° C. For example, the heating may be performed at a temperature of about 200, 210, 220, 230, 240, 250, 260, 270, 280, 290, or 300° C. The heating of the physically manipulated dosage form may have a duration of at least one minute. For example, the heating may have a duration of about 1, 2, 3, 4, 5, 6, 7, 8, 9, 10, 11, 12, 13, 14, 15, 16, 17, 18, 19, or 20 minutes, or longer. The heated, physically manipulated dosage forms according to the present disclosure may release less esketamine (base equivalent) after incubation in water or 0.1 N HCl for up to 18 hours, as compared to the release of esketamine from a physically manipulated dosage form control that has not been heated prior to incubation in water or 0.1 N HCl for up to 18 hours. In some embodiments, the heated, physically manipulated dosage form releases at least 20 wt. % less esketamine, as compared to the release of esketamine (base equivalent) from a physically manipulated dosage form control that has not been heated prior to incubation in water or 0.1 N HCl for up to 18 hours. For example, the heated, physically manipulated dosage form may release about 20-55, 20-50, 23-50, 25-45, 30-40, or 35-40 wt. % less esketamine, or about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 wt. % less esketamine, as compared to the release of esketamine (base equivalent) from a physically manipulated dosage form control that has not been heated prior to incubation in water or 0.1 N HCl for up to 18 hours.

The present dosage forms may also resist attempted abuse by physical manipulation (e.g., crushing and optionally wetting) followed by nasal insufflation, which represents a further commonly used approach for attempted abuse of an active ingredient from a dosage form. This characteristic is described more fully in connection with the examples, infra. With respect to certain embodiments, upon physically manipulating the dosage form by crushing, the physically manipulated dosage form exhibits less than 5 wt. % (e.g., less than about 4.9, 4.8, 4.7, 4.6, 4.5, 4.4, 4.3, 4.2, 4.1, 4, 3.9, 3.8, 3.7, 3.6, 3.5, 3.4, 3.3, 3.2, 3.1, 3 wt. %) the esketamine diffusion of powdered pure esketamine or a pharmaceutically acceptable salt thereof, over 60 minutes across a membrane having a molecular weight cutoff of 12-14 kD from a receptor chamber containing a phosphate buffer at pH 6.4 and maintained at 37° C. In some embodiments, wherein upon physically manipulating the dosage form by crushing, the physically manipulated dosage form exhibits less esketamine diffusion across nasal membranes of a human subject when nasally insufflated by the subject, relative to a solution of 140 mg/ml esketamine (base equivalent) in pH 4.5 citrate buffer. With respect to some embodiments, wherein upon physically manipulating the dosage form by crushing, the physically manipulated dosage form exhibits less than 5% the relative esketamine diffusion of a solution of 140 mg/ml esketamine (base equivalent) in pH 4.5 citrate buffer, over 60 minutes across a membrane having a molecular weight cutoff of 12-14 kD from a receptor chamber containing a phosphate buffer at pH 6.4 and maintained at 37° C. In some embodiments, wherein upon physically manipulating the dosage form by crushing, the absorption of esketamine from the physically manipulated dosage form over 60 minutes across a membrane having a molecular weight cutoff of 12-14 kD from a receptor chamber containing a phosphate buffer at pH 6.4 and maintained at 37° C. is less than 20%, e.g., about 19, 18, 17, 16, 15, 14, 13, 12, 11, 10, 9, 8, 7, 6, 5, 4, 3, or 2%. With respect to these embodiments, the physically manipulated dosage form according to the present disclosure may be dry or pre-wetted prior to the aforementioned assessment of absorption across a membrane.

The present disclosure also provides oral tablets for the administration of esketamine to a subject comprising: a total weight of not less than 800 mg (e.g., not less than about 800, 816, 833, 851, 870, 889, 909, 930, 952, 976, 1000, 1026, 1053, 1081, 1111, 1143, 1176, 1212, 1250, 1290, 1333 mg), and having 40 mg of esketamine (base equivalent), the esketamine (base equivalent) representing less than 5.0% (e.g., less than about 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0%) by weight of the total weight of the tablet. In other aspects, the disclosure provides oral tablets for the administration of esketamine to a subject comprising: a total weight of not less than 571 mg (e.g., not less than about 571, 588, 606, 625, 667, 690, 714, 741, 769, 800, 833, 870, 909, 952, 1000, 1053, 1111, 1176, 1250, 1333 mg), and having 20 mg of esketamine (base equivalent), the esketamine (base equivalent) representing less than 3.5% (e.g., less than about 3.5, 3.4, 3.3, 3.2, 3.1, 3.0. 2.9. 2.8, 2.7, 2.6, 2.5, 2.4, 2.3, 2.2, 2.1, 2.0, 1.9, 1.8, 1.7, 1.6, 1.5%) by weight of the total weight of the tablet. In these aspects, the tablet exhibits an immediate release profile of esketamine, having not less than 90% of the esketamine released in 60 minutes, and wherein the release profile is evaluated by dissolution of the tablet in 300 mL of 0.1N HCl media using USP II apparatus at 50 RPM paddle speed and 37° C.; and wherein the tablet exhibits an immediate release profile of the esketamine when administered to a human in therapeutic doses, and an extended release profile of the esketamine when administered to a human in supratherapeutic doses, or wherein the tablet exhibits abuse resistant properties when physically manipulated, or wherein the tablet exhibits abuse resistant properties when physically manipulated and administered in a manner not consistent with oral dosing, or wherein the tablet exhibits abuse resistant properties when administered in a manner intended to result in administration of the esketamine in a higher than therapeutic dose.

Also disclosed herein are methods for reducing the potential for abuse by a human of an active pharmaceutical ingredient comprising esketamine by simultaneous oral ingestion of multiple dosage units comprising the active pharmaceutical ingredient, comprising providing to the human a dosage form according to any of the embodiments described herein.

The present disclosure also provides methods for reducing the potential for abuse by nasal insufflation by a human of an active pharmaceutical ingredient comprising esketamine, comprising providing to the human a dosage form according to any of the embodiments described herein.

Also provided are methods for treating or preventing pain or discomfort in a subject in need thereof by administering to the subject a dosage form according to any of the embodiments described herein. Likewise, the present disclosure provides methods for treating depression in a subject in need thereof by administering to the subject a dosage form according to any of the embodiments described herein.

Impurities can be present in the active pharmaceutical ingredient (API) or in the pharmaceutical dosage form, for example, in tablets comprising the API and pharmaceutically acceptable excipients. In the case of impurities found in the pharmaceutical dosage form that do not arise from having been present in the corresponding API, those impurities may be the result of one or more excipients reacting with esketamine hydrochloride. Such reactions may give rise to esketamine hydrochloride degradation and/or the formation of esketamine by-products. In some instances, degradation, side product formation, by-product formation, and/or adjunct reagent formation occurs only after storage, for example, long-term storage, or after exposure to accelerated stability studies.

Generally, side products, by-products, and adjunct reagents (singularly "impurity" or collectively "impurities") are defined spectroscopically and/or with another physical method, and then associated with a peak position, such as that in a chromatogram or a spot on a thin layer chromatography (TLC) plate. (Strobel, H. A.; Heineman, W. R., Chemical Instrumentation: A systematic Approach, 3rd ed. (Wiley & Sons: New York 1989) p. 953.) Thereafter, the impurity can be identified by its position in the chromatogram where the position in a chromatogram is conventionally measured in minutes between injection of the sample on the column and elution of the particular component through the detector. The retention time can vary based upon the condition of the instrumentation, as well as many other factors. To mitigate the effects such variations have upon accurate identification of an impurity, practitioners use the "Relative retention time," (RRT) to identify impurities. (Strobel p. 922) The RRT of an impurity is defined as the retention time of the impurity divided by the retention time of a reference marker. It may be advantageous to select a compound other than the API that is added to the mixture in an amount sufficiently large to be detectable and sufficiently low as not to saturate the column and to use that compound as the reference marker for determination of the RRT.

A reference standard is a compound in a relatively pure state, used to quantify the amount of the compound in an unknown mixture. A reference standard can be used as either an external standard or as an internal standard. An external standard is employed when a solution of a known concentration of the reference standard and an unknown mixture are analyzed using the same technique. The amount of the compound in the mixture can be determined by comparing the magnitude of the detector responses. An internal standard is employed when an unknown mixture contains a detectable amount of the reference standard compound without addition of the reference standard. The amount of internal standard is determined by preparing at least two samples by adding known and differing amounts of the internal standard. The proportion of the detector response due to the reference standard present in the mixture can be determined by plotting the detector response attained for each of the samples against the amount of the reference standard added to each of the samples and extrapolating the plot to zero.

The present disclosure provides immediate release tablets comprising esketamine or a pharmaceutically acceptable salt thereof, a pH adjuster in an amount of no more than about 2 wt % and 2-(2-chlorophenyl)-2-(methylamino)-6-methylidenecyclohexan-1-one in amount in an amount of no more than about 5 wt % after storage in accelerated conditions for at least 6 months.

In one embodiment, the pH adjuster is in the dosage form in an amount of no more than 2 percent by weight. In one embodiment, the pH adjuster is in the dosage form in an amount of no more than 2 percent, no more than 1.9 percent, no more than 1.8 percent, no more than 1.7 percent, no more than 1.6 percent, no more than 1.5 percent, no more than 1.4 percent, no more than 1.3 percent, no more than 1.2 percent, no more than 1.1 percent, no more than 1 percent, no more than 0.9 percent, no more than 0.8 percent, no more than 0.7 percent, no more than 0.6 percent, no more than 0.6 percent, no more than 0.5 percent, no more than 0.4 percent, no more than 0.3 percent, no more than 0.2 percent, or no more than 0.1 percent by weight. In one embodiment, the present dosage form comprises a pH adjuster in an amount that is less than 0.1 percent by weight. In one embodiment, the present dosage form does not comprise a pH adjuster.

In one embodiment, the pH adjuster is in the form of a base. Suitable agents that can act as a pH adjuster include, for example, phosphate buffering agents such as, disodium hydrogen phosphate, sodium dihydrogen phosphate and the equivalent potassium salts; carbonate or bicarbonate salts, such as sodium bicarbonate, sodium carbonate, potassium bicarbonate, potassium carbonate, magnesium carbonate and calcium carbonate; hydroxide bases such as, sodium hydroxide, potassium hydroxide, ammonium hydroxide; and amine bases such as, triethanolamine, tromethamine, aminomethyl propanol, and tetrahydroxypropyl ethylenediamine. In one embodiment, the pH adjuster is sodium bicarbonate.

In one embodiment, the 2-(2-chlorophenyl)-2-(methylamino)-6-methylidenecyclohexan-1-one in the dosage form is present in an amount of no more than 5 percent by weight. In one embodiment, the 2-(2-chlorophenyl)-2-(methylamino)-6-methylidenecyclohexan-1-one in the dosage form is in an amount of no more than 5 percent, no more than 4.9 percent, no more than 4.8 percent, no more than 4.7 percent, no more than 4.6 percent, no more than 4.5 percent, no more than 4.4 percent, no more than 4.3 percent, no more than 4.2 percent, no more than 4.1 percent, no more than 4 percent, no more than 3.9 percent, no more than 3.8 percent, no more than 3.7 percent, no more than 3.6 percent, no more than 3.5 percent, no more than 3.4 percent, no more than 3.3 percent, no more than 3.2 percent, no more than 3.1 percent, no more than 3 percent, no more than 2.9 percent, no more than 2.8 percent, no more than 2.7 percent, no more than 2.6 percent, no more than 2.5 percent, no more than 2.4 percent, no more than 2.3 percent, no more than 2.2 percent, no more than 2.1 percent, no more than 2 percent, no more than 1.9 percent, no more than 1.8 percent, no more than 1.7 percent, no more than 1.6 percent, no more than 1.5 percent, no more than 1.4 percent, no more than 1.3 percent, no more than 1.2 percent, no more than 1.1 percent, no more than 1 percent, no more than 0.9 percent, no more than 0.8 percent, no more than 0.7 percent, no more than 0.6 percent, no more than 0.5 percent, no more than 0.45 percent, no more than 0.4 percent, no more than 0.35 percent, no more than 0.3 percent, no more than 0.25 percent, no more than 0.2 percent, no more than 0.19 percent, no more than 0.18 percent, no more than 0.17 percent, no more than 0.16 percent, no more than 0.15 percent, no more than 0.14 percent, no more than 0.13 percent, no more than 0.12 percent, no more than 0.11 percent, no more than 0.1 percent, no more than 0.09 percent, no more than 0.08 percent, no more than 0.07 percent, no more than 0.06 percent, no more than 0.05 percent, no more than 0.04 percent, no more than 0.03 percent, no more than 0.02 percent, or no more than 0.01 percent by weight. In one embodiment, the present dosage form is substantially free of 2-(2-chlorophenyl)-2-(methylamino)-6-methylidenecyclohexan-1-one.

In one embodiment, the present dosage form does not comprise by weight any 2-(2-chlorophenyl)-2-(methylamino)-6-methylidenecyclohexan-1-one, namely the present dosage form comprises no detectable 2-(2-chlorophenyl)-2-(methylamino)-6-methylidenecyclohexan-1-one by weight, as determined by HPLC, using UV detection at 215 nm. As used throughout the present disclosure, "substantially free" refers to the present dosage form having less than 0.01 percent by weight of a particular ingredient or excipient as determined by HPLC, using UV detection at 215 nm.

As used throughout the present disclosure, "accelerated conditions" refers to 40° C.±2° C. and 75%±5% relative humidity (RH). In one embodiment, the storage in accelerated conditions is at 40° C.±2° C. and 75%±5% RH. In one embodiment, the storage is at 40° C. and 75% RH. In one embodiment, the storage is for at least 6 months. In one embodiment, the storage is for at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, or at least 36 months.

The amount of esketamine in the dosage forms can be any useful amount, as is known and as may be found in relevant literature. For example, typical therapeutic amounts of esketamine are 5 mg, 10 mg, 20 mg, 30 mg, 40 mg. 50 mg, 60 mg, 70 mg. 80 mg, 90 mg, or 100 mg. In one embodiment, the amount of esketamine in the dosage form comprises between 5 and 100 mg of esketamine (base equivalent) or pharmaceutically acceptable salt thereof. In one embodiment, the amount of esketamine in the dosage form comprises 20 mg of esketamine (base equivalent) or pharmaceutically acceptable salt thereof. In one embodiment, the amount of esketamine in the dosage form 40 mg of esketamine (base equivalent) or pharmaceutically acceptable salt thereof.

The present disclosure provides immediate release tablets comprising esketamine or a pharmaceutically acceptable salt thereof, a pH adjuster in an amount of no more than about 2 wt %, a polymer, and 2-(2-chlorophenyl)-2-(methylamino)-6-methylidenecyclohexan-1-one in amount that is no more than about 5 wt % after storage in accelerated conditions for at least 6 months.

In one embodiment, the present dosage form comprises a polymer. In one embodiment, the present dosage form comprises more than one polymers. In one embodiment, the one or more polymers are gelling polymers (e.g. natural starches, synthetic starches, natural celluloses, synthetic celluloses, acrylates, polyalkylene oxides, carbomers and combinations thereof) and can be independently selected from ethylcellulose, cellulose acetate, cellulose acetate propionate, cellulose acetate butyrate, cellulose acetate phthalate, cellulose triacetate, cellulose ether, cellulose ester, cellulose ester ether, cellulose, hydroxypropyl methyl cellulose, hydroxy methyl cellulose, methyl cellulose, hydroxyethylmethyl cellulose, sodium carboxymethyl cellulose, a carbomer polymer, polyethylene oxide, and combinations thereof. In one embodiment, the one or more polymers are pH-sensitive polymers. In one embodiment, the one or more pH-sensitive polymers is a copolymer of dimethyl aminoethyl methacrylate, butyl methacrylate, and methyl methacrylate monomers.

In one embodiment, the one or more polymers are C1 moiety donating polymers. As used throughout the present disclosure, "C1 moiety" refers to a chemical fragment comprising only one Carbon atom (e.g. methyl, methylene). As used throughout the present disclosure, a "C1 moiety donating polymer" is a polymer capable of transferring from itself to another substance a C1 moiety.

In one embodiment, the esketamine or a pharmaceutically acceptable salt thereof, is in contact with a polymer. As used throughout the present disclosure, "in contact with" refers to two or more substances that are close enough to interact with each other. In one embodiment, the contact may be direct contact or physical contact, where there is generally no measurable space or distance between the contact points of the two substances. In one embodiment, the contact may be indirect contact, or non-physical contact, where there is a measurable space or distance between the contact points of the two substances.

In one embodiment, the ratio, by weight, of polymer in contact with esketamine or pharmaceutically acceptable salt thereof, is between about 2 and about 15.8 to 1. In one embodiment, the ratio, by weight, of polymer in contact with esketamine is between about 2 and about 15.8 to 1 (i.e., ~2 to ~15.8:1). In one embodiment, the ratio, by weight, of polymer in contact with esketamine is about 2, about 2.1, about 2.2, about 2.3, about 2.4, about 2.5, about 2.6, about 2.7, about 2.8, about 2.9, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, about 9, about 9.1, about 9.2, about 9.3, about 9.4, about 9.5, about 9.6, about 9.7, about 9.8, about 9.9, about 10, about 10.1, about 10.2, about 10.3, about 10.4, about 10.5, about 10.6, about 10.7, about 10.8, about 10.9, about 11, about 11.1, about 11.2, about 11.3, about 11.4, about 11.5, about 11.6, about 11.7, about 11.8, about 11.9, about 12, about 12.1, about 12.2, about 12.3, about 12.4, about 12.5, about 12.6, about 12.7, about 12.8, about 12.9, about 13, about 13.1, about 13.2, about 13.3, about 13.4, about 13.5, about 13.6, about 13.7, about 13.8, about 13.9, about 14, about 14.1, about 14.2, about 14.3, about 14.4, about 14.5, about 14.6, about 14.7, about 14.8, about 14.9, about 15, about 15.1, about 15.2, about 15.3, about 15.4, about 15.5, about 15.6, about 15.7 or about 15.8 to 1.

In one embodiment, the ratio, by weight, of polymer in contact with esketamine or pharmaceutically acceptable salt thereof, is at least about 2 to 1. In one embodiment, the ratio, by weight, of polymer in contact with esketamine is at least about 2, at least about 2.1, at least about 2.2, at least about 2.3, at least about 2.4, at least about 2.5, at least about 2.6, at least about 2.7, at least about 2.8, at least about 2.9, at least about 2, at least about 2.1, at least about 2.2, at least about 2.3, at least about 2.4, at least about 2.5, at least about 2.6, at least about 2.7, at least about 2.8, at least about 2.9, at least about 3, at least about 3.1, at least about 3.2, at least about 3.3, at least about 3.4, at least about 3.5, at least about 3.6, at least about 3.7, at least about 3.8, at least about 3.9, at least about 4, at least about 4.1, at least about 4.2, at least about 4.3, at least about 4.4, at least about 4.5, at least about 4.6, at least about 4.7, at least about 4.8, at least about 4.9, at least about 5, at least about 5.1, at least about 5.2, at least about 5.3, at least about 5.4, at least about 5.5, at least about 5.6, at least about 5.7, at least about 5.8, at least about 5.9, at least about 6, at least about 6.1, at least about 6.2, at least about 6.3, at least about 6.4, at least about 6.5, at least about 6.6, at least about 6.7, at least about 6.8, at least about 6.9, at least about 7, at least about 7.1, at least about 7.2, at least about 7.3, at least about 7.4, at least about 7.5, at least about 7.6, at least about 7.7, at least about 7.8, at least about 7.9, at least about 8, at least about 8.1, at least about 8.2, at least about 8.3, at least about 8.4, at least about 8.5, at least about 8.6, at least about 8.7, at least about 8.8, at least about 8.9, at least about 9, at least about 9.1, at least about 9.2, at least about 9.3, at least about 9.4, at least about 9.5, at least about 9.6, at least about 9.7, at least about 9.8, at least about 9.9, at least about 10, at least about 10.1, at least about 10.2, at least about 10.3, at least about 10.4, at least about 10.5, at least about 10.6, at least about 10.7, at least about 10.8, at least about 10.9, at least about 11, at least about 11.1, at least about 11.2, at least about 11.3, at least about 11.4, at least about 11.5, at least about 11.6, at least about 11.7, at least about 11.8, at least about 11.9, at least about 12, at least about 12.1, at least about 12.2, at least about 12.3, at least about 12.4, at least about 12.5, at least about 12.6, at least about 12.7, at least about 12.8, at least about 12.9, at least about 13, at least about 13.1, at least about 13.2, at least about 13.3, at least about 13.4, at least about 13.5, at least about 13.6, at least about 13.7, at least about 13.8, at least about 13.9, at least about 14, at least about 14.1, at least about 14.2, at least about 14.3, at least about 14.4, at least about 14.5, at least about 14.6, at least about 14.7, at least about 14.8, at least about 14.9, at least about 15, at least about 15.1, at least about 15.2, at least about 15.3, at least about 15.4, at least about 15.5, at least about 15.6 or at least about 15.7 to 1.

In one embodiment, the weight percentage ratio of polymer to esketamine is less than 2.6 to 1. In one embodiment, the weight percentage ratio of polymer to esketamine is less than 2.6, less than 2.5, less than 2.4, less than 2.3, less than 2.2, less than 2.1, less than 2, less than 1.9, less than 1.8, less than 1.7, less than 1.6, less than 1.5, less than 1.4, less than 1.3, less than 1.2, less than 1.1, less than 1, less than 0.9, less than 0.8, less than 0.7, less than 0.6, less than 0.5, less than 0.4, less than 0.3, less than 0.2 or less than 0.1 to 1. In one embodiment, the weight percentage ratio of polymer to esketamine (base equivalent) is 0.75 to 1. In one embodiment, the weight percentage ratio of polymer to pharmaceutically acceptable salt of esketamine is 0.65 to 1.

In one embodiment, the ratio, by weight of polymer is to esketamine (base equivalent). In another embodiment, the ratio, by weight of polymer is to a pharmaceutically acceptable salt of esketamine. In one embodiment, the ratio, by weight, is of any polymer in contact with the esketamine or pharmaceutically acceptable salt thereof. In another embodiment, the ratio, by weight, is of the total polymer in contact with the esketamine or pharmaceutically acceptable salt.

The present disclosure also provides methods of manufacturing an immediate release tablet comprising esketamine or a pharmaceutically acceptable salt thereof and a pH adjuster in an amount of no more than about 2 wt %. In one embodiment, the method comprises wet milling excipients. In one embodiment, the method comprises dry milling excipients. In one embodiment, the method comprises wet followed by dry milling excipients. In one embodiment, the immediate release tablet manufactured according to the method comprises 2-(2-chlorophenyl)-2-(methylamino)-6-methylidenecyclohexan-1-one in an amount that is no more than about 5 wt % after storage in accelerated conditions for at least 6 months.

The present disclosure also provides for methods of treating depression comprising orally administering to a subject in need thereof, an immediate release tablet comprising esketamine or a pharmaceutically acceptable salt thereof, a pH adjuster in an amount of no more than about 2 wt % and 2-(2-chlorophenyl)-2-(methylamino)-6-methylidenecyclohexan-1-one in amount that is no more than about 5 wt % after storage in accelerated conditions for at least 6 months. In one embodiment, the present dosage form comprises between 5 and 100 mg of esketamine or pharmaceutically acceptable salt thereof. In one embodiment, the present dosage form comprises 5 mg, 10 mg, 20 mg, 30 mg, 40 mg. 50 mg, 60 mg, 70 mg. 80 mg, 90 mg, or 100 mg of esketamine or pharmaceutically acceptable salt thereof. In one embodiment, the present dosage form comprises between 5 and 100 mg of esketamine (base equivalent) or pharmaceutically acceptable salt thereof. In one embodiment, the present dosage form comprises 20 mg of esketamine (base equivalent) or pharmaceutically acceptable salt thereof. In one embodiment, the present dosage form comprises 40 mg of esketamine (base equivalent) or pharmaceutically acceptable salt thereof.

The present disclosure also provides for immediate release oral tablets comprising core shell particles, comprising a) a core surrounded by a first layer comprising esketamine and pharmaceutically acceptable salts thereof and a second layer comprising a pH-sensitive polymer that is soluble in an aqueous environment at a pH below 5, wherein the first layer is at least partially surrounded by the second layer;

b) no more than 2 wt % of a pH adjuster; and c) no more than about 5 wt % of 2-(2-chlorophenyl)-2-(methylamino)-6-methylidenecyclohexan-1-one after storage in accelerated conditions for at least 6 months.

In one embodiment, the core comprises a gelling polymer (e.g. natural starches, synthetic starches, natural celluloses, synthetic celluloses, acrylates, polyalkylene oxides, carbomers and combinations thereof). In one embodiment, the core comprises one or more gelling polymers. In one embodiment, the gelling polymer can be independently selected from ethylcellulose, cellulose acetate, cellulose acetate propionate, cellulose acetate butyrate, cellulose acetate phthalate, cellulose triacetate, cellulose ether, cellulose ester, cellulose ester ether, cellulose, hydroxypropyl methyl cellulose, hydroxy methyl cellulose, methyl cellulose, hydroxyethylmethyl cellulose, sodium carboxymethyl cellulose, a carbomer polymer, polyethylene oxide, and combinations thereof.

In one embodiment, the first layer comprises esketamine or pharmaceutically acceptable salts thereof and a polymer. In one embodiment, the polymer is a gelling polymer. In one embodiment, the polymer is hypromellose (HPMC).

In one embodiment, the one or more pH-sensitive polymers is a copolymer of dimethyl aminoethyl methacrylate, butyl methacrylate, and methyl methacrylate monomers.

The present disclosure provides for an isolated compound of the formula: 2-(2-chlorophenyl)-2-(methylamino)-6-methylidenecyclohexan-1-one. The disclosure also provides a composition comprising 2-(2-chlorophenyl)-2-(methylamino)-6-methylidenecyclohexan-1-one wherein the composition is free of esketamine and to a composition comprising 2-(2-chlorophenyl)-2-(methylamino)-6-methylidenecyclohexan-1-one in an amount of at least 0.2 wt % and a carrier.

The present disclosure also provides a pharmaceutical composition comprising a granulate of a mixture of: a) esketamine hydrochloride; b) at least one pharmaceutically acceptable carrier; and c) less than 5 wt % of 2-(2-chlorophenyl)-2-(methylamino)-6-methylidenecyclohexan-1-one.

The present disclosure also provides a process for preparing an immediate release tablet comprising esketamine hydrochloride and a pharmaceutically acceptable carrier, wherein the tablet comprises less than 5 wt % of 2-(2-chlorophenyl)-2-(methylamino)-6-methylidenecyclohexan-1-one, comprising:

a. obtaining esketamine hydrochloride drug substance;

b. determining the total amount of 2-(2-chlorophenyl)-2-(methylamino)-6-methylidenecyclohexan-1-one present in the esketamine hydrochloride drug substance; and c. including in the preparation of the tablet the esketamine hydrochloride drug substance determined to have less than about 5 wt % of 2-(2-chlorophenyl)-2-(methylamino)-6-methylidenecyclohexan-1-one.

The present disclosure also provides a process for validating a batch of immediate release tablets containing esketamine hydrochloride and at least one pharmaceutically acceptable carrier for distribution comprising:

a. determining whether the total amount of 2-(2-chlorophenyl)-2-(methylamino)-6-methylidenecyclohexan-1-one in a sample of the batch after stability testing is less than about 5 wt % of 2-(2-chlorophenyl)-2-(methylamino)-6-methylidenecyclohexan-1-one; and b. validating the batch for distribution that has been determined to have less than about 5 wt % of 2-(2-chlorophenyl)-2-(methylamino)-6-methylidenecyclohexan-1-one.

As used throughout the present disclosure, "stability testing" shall include testing at accelerated conditions for at least 6 months.

The present disclosure provides a compound of the following structural formula:

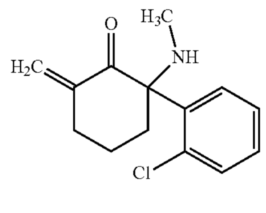 [SMILES: C=C1CCCC(NC)(c2ccccc2Cl)C1=O]

The chemical name of this compound is: 2-(2-chlorophenyl)-2-(methylamino)-6-methylidenecyclohexan-1-one. As used throughout the present disclosure, "2-(2-chlorophenyl)-2-(methylamino)-6-methylidenecyclohexan-1-one" refers to both racemic and enantiomerically enriched, e.g. enantiomerically pure, forms of the compound. In one embodiment, the compound is racemic 2-(2-chlorophenyl)-2-(methylamino)-6-methylidenecyclohexan-1-one. In one embodiment, the compound is enantiomerically enriched in one enantiomer. In one embodiment, the compound is enriched in the S enantiomer. In another embodiment, the compound is enriched in the R enantiomer.

The present disclosure also provides an isolated compound of formula: 2-(2-chlorophenyl)-2-(methylamino)-6-methylidenecyclohexan-1-one and to a composition comprising a compound of formula: 2-(2-chlorophenyl)-2-(methylamino)-6-methylidenecyclohexan-1-one wherein the composition is free of esketamine hydrochloride.

The present disclosure also provides a composition comprising 2-(2-chlorophenyl)-2-(methylamino)-6-methylidenecyclohexan-1-one in an amount of at least 0.2 wt % and a carrier. In one embodiment, the composition comprises at least 1.5 wt % of 2-(2-chlorophenyl)-2-(methylamino)-6-methylidenecyclohexan-1-one, based on the weight of the composition.

In another embodiment, the composition comprises at least 50 wt % of 2-(2-chlorophenyl)-2-(methylamino)-6-methylidenecyclohexan-1-one. In another embodiment, the composition comprises from more than 0) to 99.5 wt % by weight of esketamine hydrochloride. In another embodiment, the composition comprises from more than 0 to 95 wt % by weight of esketamine hydrochloride.

In another embodiment, the composition is a pharmaceutical composition and the carrier is a pharmaceutically acceptable carrier. In one embodiment of the pharmaceutical composition, 2-(2-chlorophenyl)-2-(methylamino)-6-methylidenecyclohexan-1-one is present in an amount between 0.01 wt % and 5.0 wt % in the composition. In another embodiment of the pharmaceutical composition, 2-(2-chlorophenyl)-2-(methylamino)-6-methylidenecyclohexan-1-one is present in an amount between 0.01 wt % and 0.5 wt % in the composition. In another embodiment of the pharmaceutical composition, 2-(2-chlorophenyl)-2-(methylamino)-6-methylidenecyclohexan-1-one is present in an amount between 0.01 wt % and 0.2 wt % in the composition. In another embodiment of the pharmaceutical composition, the 2-(2-chlorophenyl)-2-(methylamino)-6-methylidenecyclohexan-1-one is present in an amount between 0.01 wt % and 0.1 wt % in the composition.

The present disclosure also provides a pharmaceutical composition comprising a granulate of a mixture of: a) esketamine hydrochloride; b) at least one pharmaceutically acceptable carrier; and c) less than 5 wt % of 2-(2-chlorophenyl)-2-(methylamino)-6-methylidenecyclohexan-1-one. In one embodiment of the pharmaceutical composition, 2-(2-chlorophenyl)-2-(methylamino)-6-methylidenecyclohexan-1-one is present in an amount less than 0.5 wt %. In one embodiment of the pharmaceutical composition, 2-(2-chlorophenyl)-2-(methylamino)-6-methylidenecyclohexan-1-one is present in an amount less than 0.1 wt %.

In one embodiment of the pharmaceutical composition, the granulate is a product of wet granulation. In one embodiment of the pharmaceutical composition, the granulate is a milled granulate. In one embodiment of the pharmaceutical composition, the granulate is both wet granulated and milled. In one embodiment of the pharmaceutical composition, the granulate is both wet and dry milled.

In one embodiment, the pharmaceutical composition further comprises no more than 2 wt % of a pH adjuster. In one embodiment, the pharmaceutical composition is in the form of an immediate release tablet.

In one embodiment of the pharmaceutical composition, the tablet comprises, by weight, between 1% and 4% esketamine hydrochloride, no more than 2% of a pH adjuster and no more than 5% of 2-(2-chlorophenyl)-2-(methylamino)-6-methylidenecyclohexan-1-one.

The present disclosure also provides a sealed package comprising the composition described herein or the pharmaceutical composition described herein. In one embodiment of the sealed package, a net increase of the total content of 2-(2-chlorophenyl)-2-(methylamino)-6-methylidenecyclohexan-1-one in the pharmaceutical composition is 5 wt % or less after storage of the sealed package at accelerated conditions for at least 6 months. In one embodiment, the net increase is 0.5 wt % or less after storage at accelerated conditions for at least 6 months. In one embodiment, the net increase is 0.1 wt % or less after storage at accelerated conditions for at least 6 months. In one embodiment, the net increase is less than 0.1 wt % after storage at accelerated conditions for at least 6 months.

In one embodiment, the sealed package comprises the pharmaceutical composition described herein, wherein the pharmaceutical composition contains less than 5 wt % of 2-(2-chlorophenyl)-2-(methylamino)-6-methylidenecyclohexan-1-one after storage of the sealed package at accelerated conditions for at least 6 months. In one embodiment, the pharmaceutical composition contains 0.5 wt % of 2-(2-chlorophenyl)-2-(methylamino)-6-methylidenecyclohexan-1-one or less after storage at accelerated conditions for at least 6 months. In one embodiment, the pharmaceutical composition contains 0.1 wt % of 2-(2-chlorophenyl)-2-(methylamino)-6-methylidenecyclohexan-1-one or less after storage at accelerated conditions for at least 6 months. In one embodiment, the pharmaceutical composition contains less than 0.1 wt % of 2-(2-chlorophenyl)-2-(methylamino)-6-methylidenecyclohexan-1-one after storage at accelerated conditions for at least 6 months.

In one embodiment of the sealed package, the pharmaceutical composition further comprises 2-(2-chlorophenyl)-2-(methylamino)-6-methylidenecyclohexan-1-one in an amount of 1.0 wt %, or below; in the pharmaceutical composition. In another embodiment of the sealed package, 2-(2-chlorophenyl)-2-(methylamino)-6-methylidenecyclohexan-1-one is present in the pharmaceutical composition in an amount of less than 0.1 wt %. In another embodiment of the sealed package, the pharmaceutical composition contains less than 1.0 wt % of 2-(2-chlorophenyl)-2-(methylamino)-6-methylidenecyclohexan-1-one after storage of the sealed package at accelerated conditions for at least 6 months. In one embodiment of the sealed package, a net increase of the total content of 2-(2-chlorophenyl)-2-(methylamino)-6-methylidenecyclohexan-1-one in the pharmaceutical composition is 5 wt % or less after storage of the sealed package at accelerated conditions for at least 6 months.

In one embodiment of the sealed package, the pharmaceutical composition further comprises no more than 2 wt % of a pH adjuster. In one embodiment of the sealed package, the pharmaceutical composition is in the form of an immediate release tablet. In one embodiment of the sealed package, the pharmaceutical composition comprises, by weight, between 1% and 4% esketamine hydrochloride, no more than 2% of a pH adjuster and no more than 5% of 2-(2-chlorophenyl)-2-(methylamino)-6-methylidenecyclohexan-1-one.

In one embodiment of the sealed package, the pharmaceutical composition is prepared by wet granulation. In one embodiment of the sealed package, the granulate is a milled granulate. In one embodiment of the sealed package, the granulate is both wet granulated and milled. In one embodiment of the sealed package, the granulate is both wet and dry milled. In one embodiment of the sealed package, the sealed package is an HDPE bottle.

The present disclosure also provides a process for preparing the pharmaceutical composition described herein or the sealed package described herein, comprising: a. obtaining esketamine hydrochloride drug substance; b. determining the total amount of 2-(2-chlorophenyl)-2-(methylamino)-6-methylidenecyclohexan-1-one present in the esketamine hydrochloride drug substance; and c. including the esketamine hydrochloride drug substance in the preparation of the pharmaceutical composition, drug substance determined to have less than 0.10 wt % by weight of 2-(2-chlorophenyl)-2-(methylamino)-6-methylidenecyclohexan-1-one.

The present disclosure also provides a process for preparing a pharmaceutical composition comprising esketamine hydrochloride and a pharmaceutically acceptable carrier, wherein the pharmaceutical composition comprises less than 5 wt % of 2-(2-chlorophenyl)-2-(methylamino)-6-methylidenecyclohexan-1-one, comprising: a. obtaining esketamine hydrochloride drug substance; b. determining the total amount of 2-(2-chlorophenyl)-2-(methylamino)-6-methylidenecyclohexan-1-one present in the esketamine hydrochloride drug substance; and c. including the esketamine hydrochloride drug substance in the preparation of the pharmaceutical composition drug substance determined to have less than 0.10 wt % of 2-(2-chlorophenyl)-2-(methylamino)-6-methylidenecyclohexan-1-one.

The present disclosure also provides a process for validating a batch of a pharmaceutical composition containing esketamine hydrochloride and at least one pharmaceutically acceptable carrier for distribution comprising:

a. determining the total amount of 2-(2-chlorophenyl)-2-(methylamino)-6-methylidenecyclohexan-1-one in a sample of the batch after stability testing; and
b. validating the batch for distribution the batch determined in step a) to contain less than 5 wt % of 2-(2-chlorophenyl)-2-(methylamino)-6-methylidenecyclohexan-1-one.

In one embodiment of the process, the batch validated for distribution is determined in step a) to contain less than 1.0 wt % of 2-(2-chlorophenyl)-2-(methylamino)-6-methylidenecyclohexan-1-one. In another embodiment of the process, the batch validated for distribution is determined in step a) to contain less than 0.5 wt % of 2-(2-chlorophenyl)-2-(methylamino)-6-methylidenecyclohexan-1-one. In another embodiment of the process, the batch validated for distribution is determined in step a) to contain less than 0.2 wt % of 2-(2-chlorophenyl)-2-(methylamino)-6-methylidenecyclohexan-1-one. In another embodiment of the process, the batch validated for distribution is determined in step a) to contain less than 0.1 wt % of 2-(2-chlorophenyl)-2-(methylamino)-6-methylidenecyclohexan-1-one.

The present disclosure also provides a process for making the isolated compound 2-(2-chlorophenyl)-2-(methylamino)-6-methylidenecyclohexan-1-one comprising: a. contacting esketamine hydrochloride with a pH-sensitive polymer and b. isolating the compound from the reaction mixture of step a). In one embodiment of the method, the compound is isolated from the mixture via chromatography. In one embodiment of the method, the compound is isolated from the mixture via lyophilization.

The present disclosure also provides for a method of determining the level of 2-(2-chlorophenyl)-2-(methylamino)-6-methylidenecyclohexan-1-one in esketamine hydrochloride drug substance, comprising a) Measuring by HPLC the area under a peak corresponding to esketamine in a reference standard at a known level;
b) Measuring by HPLC the area under a peak corresponding to 2-(2-chlorophenyl)-2-(methylamino)-6-methylidenecyclohexan-1-one in a sample comprising esketamine hydrochloride and 2-(2-chlorophenyl)-2-(methylamino)-6-methylidenecyclohexan-1-one;
c) Determining the amount of 2-(2-chlorophenyl)-2-(methylamino)-6-methylidenecyclohexan-1-one in the sample by comparing the area of Step (a) to the area of Step (b) and taking into account the relative response factor between 2-(2-chlorophenyl)-2-(methylamino)-6-methylidenecyclohexan-1-one and esketamine.

The present disclosure also provides for the use of 2-(2-chlorophenyl)-2-(methylamino)-6-methylidenecyclohexan-1-one as a reference standard in the preparation of batches of pharmaceutical compositions comprising esketamine or a pharmaceutically acceptable salt thereof.

As used throughout the present disclosure, "drug substance" or "DS" refers to the active ingredient in a drug product, which provides pharmacological activity or other direct effect in the diagnosis, cure, mitigation, treatment, or prevention of disease, or to affect the structure or any function of the body of man or animals. As used throughout the present disclosure, "drug product" or "DP" refers to the finished dosage form containing the drug substance as well as at least one pharmaceutically acceptable carrier.

As used throughout the present disclosure, a "sealed" package, container or coating substantially prevents the atmosphere from coming in contact with the contents of the package or container or with the material coated by the coating. As used throughout the present disclosure, an "HDPE" bottle refers to a bottle constructed of high density polyethylene plastic.

Figure 1B:
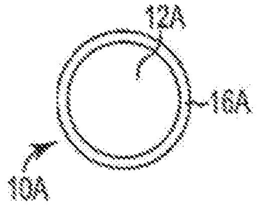
Figure 1C:
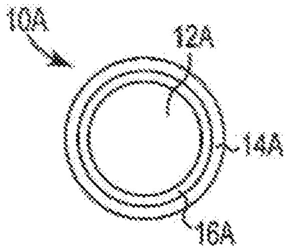

Referring to FIGS. 1A and 1B, a dosage form can include particles 10A that contain esketamine. The particle (e.g., coated particle or "core-shell" particle) can include a core 12A (or "uncoated core"), which may be coated with one or more layers, films or coatings, e.g., 14*a*, 16*a*, or any additional layer or coating that is coated over, underneath, or intermediate to these. In FIGS. 1B and 1C, the layer designated 16A may be a drug-containing layer, and the layer designated as 14A may be a solvent resistant, e.g., a pH sensitive film layer. Particle 10A can contain one or more of the ingredients described herein, such as esketamine, a gelling polymer, optional wax, optional solvent-resistant layer, as well as one or more additional layer or layers under, over, or intermediate to these layers or between either layer and the core. Each layer can be present in size or amount (e.g., thickness) that will result in a useful immediate release dosage form having one or more of the presently described abuse deterrent features. Other optional components of a core or layer of particle 10A can be filler, binder, other excipient, or solvent (not more than a residual amount, if any) such as water or ethanol for use in preparing the coated particle, and that is substantially removed after formation of the core, coating, or coated particle. Examples of e core 10A can include any amount or combination of the different ingredients of: a gelling polymer (e.g., from 0 to 100 percent of a core), filler as described herein such as sugar (mannitol) or microcrystalline cellulose (e.g., from 0 to 100 percent of a core), binder (e.g., from 0 to 100 percent of a core), and wax (e.g., from to 100 percent of a core).

While the present dosage forms containing core-shell particles 10A are new and inventive, certain method steps useful to prepare these particles may be known. Available methods include certain methods and processing steps known to be useful for preparing particles and coated particles in the pharmaceutical arts. A core-shell particle 10A can be prepared by an initial step of mixing ingredients of core 12A with a solvent such as water or ethanol and forming the mixture into a spherical core particle by known methods. The particle may be dried and separated by size, and then one or more coating in the form of a continuous film or layer can be applied to the core, optionally successively to produce multiple layers surrounding the core. General processing to produce a multi-layer coated particle can include a series of steps such as compounding, mixing, granulation, wet milling, dry milling, coating (by any method such as fluidized bed coating, spray coating, etc.), and one or more drying steps such as by use of a fluidized bed or other drying method. Intermittently between core-forming and coating steps, e.g., after a drying step, coated or uncoated particles can be sorted or separated based on size to produce a composition or a collection of particles having a desired size range and distribution. Accordingly, coated granulate compositions according to the invention may be prepared by a process comprising:

(i) granulating a wax or a gelling polymer, or a mixture thereof, in the presence of a hydroalcoholic solution or suspension comprising a suitable binder, to form granules;

(ii) layering the granules formed in step (i) with a solution or suspension comprising esketamine; and (iii) coating the layered granules formed in step (ii) with a solution or suspension comprising a film forming polymer material to form a coated layered granulate.

The process above may further comprise steps of milling and drying the granulate formed in step (i). The hydroalcoholic solution can contain any ratio of water to ethanol (e.g. 10:30, 10:35, 10:40, 10:45, 10:50, 10:55, 10:60, 10:65, 10:70, 10:75, 10:80, 10:85, 10:90, 15:30, 15:35, 15:40, 15:50, 15:55, 15:65, 15:70, 15:80, 15:85, 20:30, 20:35, 20:45, 20:50, 20:55, 20:65, 20:70, 20:75, 20:85, 20:90, 25:30, 25:35, 25:40, 25:45, 25:55, 25:60, 25:65, 25:70, 25:80, 25:85, 25:90, 30:35, 30:40, 30:50, 30:55, 30:65, 30:70, 30:75, 30:80, 30:85) and can contain any ratio of the gelling polymer (e.g. 1 part in mix to 3 parts in solution, 1 part in mix to 2 parts in solution, 1 part in mix to 1 part in solution, 2 part in mix to 1 parts in solution, 2 part in mix to 3 parts in solution, 3 part in mix to 1 parts in solution, or 3 part in mix to 2 parts in solution).

In instances wherein the core comprises a sugar sphere or a microcrystalline cellulose sphere, the steps of the process above would be modified as follows:

(i) providing a sugar sphere (or microcrystalline cellulose sphere);

(ii) layering the sugar sphere (or microcrystalline cellulose sphere) with a solution or suspension comprising an API; and (iii) coating the layered sphere formed in step (ii) with a solution or suspension comprising a film forming polymer material to form a coated layered sphere.

Compressed tablets according to the invention may be prepared by a process comprising:

(i) combining the coated layered granulate (or the coated layered sphere) prepared according to either of the above processes with a second API (e.g., acetaminophen), a gelling polymer, and a disintegrant, and optionally, with at least one additional excipient selected from a filler, a colorant, and a pH adjusting agent, to form a first mixture and then blending the first mixture for a suitable time;

(ii) adding a lubricant to the blended mixture formed in step (i) to form a second mixture, and then blending the second mixture for a suitable time;

(iii) compressing the blended mixture formed in step (ii) to form compressed tablets.

A suitable time for the blending in step (i) may be, for example, from about 5 to about 90) minutes, or from about 10 to about 60 minutes, or from about 20 to about 40 minutes, or about 30) minutes. A suitable time for the blending in step (ii) may be, for example, from about 1 to about 30 minutes, or from about 5 to about 20 minutes, or about 10 minutes.

In certain embodiments as shown at FIGS. 1A, 1B, and IC, an immediate release dosage form as described can include a core-shell particle 10A that includes a core 12A that contains no drug, only a minor amount of API, or an insubstantial amount of API. Core 12A may contain less than 5 weight percent, e.g., less than 1 or less than 0.5 weight percent active pharmaceutical ingredient based on a total weight of the core of the core-shell particle. Alternatively, core 12A may contain less than 5 weight percent of a total amount of pharmaceutical ingredient in a core-shell polymer, e.g., less than 5, less than 1, or less than 0.5 weight percent active pharmaceutical ingredient based on total weight of API in the core-shell particle. In these embodiments a major portion of API can be contained outside of core 12A, e.g., in an API layer 16A, which can contain at least 50, at least 75, or at least 90, or at least 95 weight percent of a total amount of the API in a core-shell polymer.

Core 12A can include binder, gelling polymer (e.g., HPMC), wax, filler, or any combination thereof, each in an amount to allow the materials of the core to function as one or more abuse deterrent features as described herein. See the examples included herewith for examples of useful amounts and ranges of amounts of these ingredients. In a preferred embodiment, core 12A includes HPMC, glyceryl behenate, and ethylcellulose.

Referring to FIG. 1A, core 12A contains gelling polymer, wax, binder, or filler, or any combination of these, and no API (meaning not more than an insignificant amount, such as less than 0.5, less than 0.1, or zero weight percent based on the weight of core 12A). As shown at FIGS. 1B and 1C, core 12A, not containing API, can be coated with a coating layer that contains API, e.g., an active pharmaceutical layer or API layer 16A. As shown at FIG. 1B, core-shell particle 10A includes core 12A, which does not contain any API, and API layer 16A, which contains an amount of API, such as a total amount of API (e.g., API commonly susceptible to abuse) to be contained in a dosage form prepared from particles 10A. API layer 16A can contain one or more ingredients as described herein useful to form API layer 16A as a layer over an outer surface of core 12A. API in API layer 16A can account for all of or most of (e.g., at least 70, at least 80, at least 90, or at least 95 percent) the total amount of that type of API in the core-shell particles and in the dosage form; in this embodiment, the core can contain less than 10, less than 5, or less than 1 percent of the total amount of API in the core-shell particles, and less than 10, 5, or 1 percent of the total amount of API in the dosage form. Useful non-API ingredients in an API layer can include a binder or a gelling polymer along with the API. The API and non-API ingredients can be carried in a solvent (e.g., water, ethanol, or both) and coated and dried to form a preferably continuous film layer on an outer surface of core 12A, i.e., API layer 16A. See the examples included herewith for examples of useful amounts and ranges of amounts of these ingredients. In a preferred embodiment, the API layer 16A includes esketamine and hypromellose (HPMC).

A core-shell particle 10A can also optionally include a film layer, e.g., a solvent-resistant layer (e.g., a pH-sensitive layer) 14A as described herein.

In certain alternate embodiments a dosage form as described can include a core-shell particle 10B that includes a core 12B that does contain a useful amount of API, such as an amount of API useful in an immediate release dosage form having one or more abuse deterrent features as described herein, prepared to include particles 10B. See FIGS. 2A and 2B. According to such embodiments, core 12B of particle 10B can contain a gelling polymer, optional wax, optional binder or filler, and an amount of API.

Figure 2A:
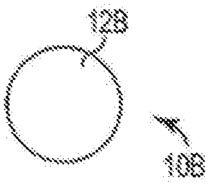
FIG. 2A and FIG. 2B also illustrate embodiments of core-shell particles, in cross section.
Figure 2B:
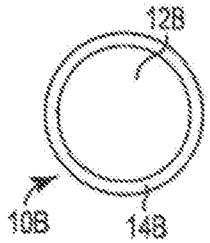
Figure 3:
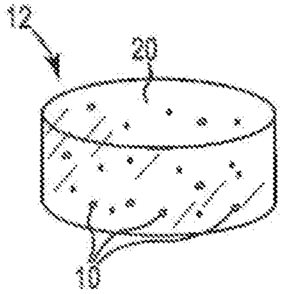
FIG. 3 is a perspective view of an embodiment of a dosage form as disclosed herein.

Referring to FIG. 2A, core 12B contains gelling polymer, optional wax, optional binder, and API. Referring to FIG. 2B, core 12B, containing API, can optionally be coated with solvent-resistant layer (e.g., a pH-sensitive layer) 14B as described herein for use in an immediate release dosage form. Core 12B may also optionally be coated with a coating layer that contains API, e.g., an active pharmaceutical layer or API layer prior to application of the solvent-resistant layer. Accordingly, API containing core-shell particles as described herein may contain API of a type that is susceptible to abuse:

- in an API layer surrounding the core and in a substantial amount in the core;
- in an API layer surrounding the core and in an insubstantial amount in the core;
- only in an API layer surrounding the core; or
- only in the core.

In certain alternative embodiments, a dosage form as described can include a core-shell particle 10B, as depicted in FIG. 2B, that that does not contain an API layer, and does not contain any API. Referring to FIG. 2C, such a particle 10B, containing no API, may include core 12B containing gelling polymer, optional wax, and optional binder, which core 12B may optionally be coated with solvent-resistant layer (e.g., a pH-sensitive layer) 14B as described herein for use in an immediate release dosage form. In a preferred embodiment of a core-shell particle 10B that does not contain an API layer, the core includes Hypromellose, glyceryl behenate, and ethylcellulose.

A coated particle 10A or 10B that includes API, and optionally, a coated particle 10B that does not include API, can be included in any of a variety of dosage forms, examples including a compressed tablet or compressed capsule, a suppository, capsule, caplet, pill, gel, soft gelatin capsule, etc. As one example, a dosage form 12 can be prepared as a compressed tablet or compressed capsule. Tablet or capsule 12 can contain core-shell particles 10 (e.g., 10A or 10B) distributed within a matrix 20, compressed to form the compressed tablet or capsule 12. Core-shell particles 10A or 10B can be as described herein, generally or specifically, and can contain an amount of API suited to provide a desired dosage upon ingestion of tablet or capsule 12; e.g., matrix 20 does not include any substantial amount of API, or contains no API at all.

Matrix 20 can include ingredients useful in combination with the core-shell particles 10A, 10B, to produce an immediate release dosage form. Examples of useful excipients of an immediate release dosage form can include ingredients that allow the dosage form to break up or disintegrate upon ingestion and facilitate exposure to fluid in a stomach, such as a useful amount of disintegrant. Examples of such excipients for such a dosage form can also include one or more ingredients that act as an abuse deterrent feature, such as a gelling polymer as described herein. Other excipients can be useful for processing to form a compressed dosage form, and also may allow the compressed dosage form to function as an immediate release dosage form, with one or more abuse deterrent features. In certain embodiments, the matrix includes a filler, a disintegrant, a binder, a gelling polymer, a pH adjuster, a glidant, and a lubricant.

The present disclosure also pertains to and includes at least the following aspects:

Aspect 1. An abuse resistant oral dosage form for the administration of esketamine to a subject comprising:

(i) a first population of core-shell particles, each of the core-shell particles of the first population comprising a core, an active pharmaceutical layer surrounding the core, the active pharmaceutical layer comprising esketamine or a pharmaceutically acceptable salt thereof, and at least one layer surrounding the active pharmaceutical layer, the at least one layer comprising a pH-sensitive film comprising a pH-sensitive polymer that is insoluble in water at a pH greater than 5; and, (ii) a matrix comprising a carbomer gelling polymer and sodium bicarbonate, wherein the carbomer gelling polymer and sodium bicarbonate are present in a ratio by weight percentage of about 2:2 based on the total weight of the dosage form;

wherein the dosage form exhibits an immediate release profile of esketamine having not less than 90% of the esketamine released in 60 minutes, wherein the release profile is evaluated by dissolution of the tablet in 300 mL of 0.1N HCl media using USP II apparatus at 50 RPM paddle speed and 37° C.;

and, wherein the dosage form exhibits an immediate release profile of the esketamine when administered to a human in therapeutic doses, and an extended release profile of the esketamine when administered to a human in supratherapeutic doses, or wherein the dosage form exhibits abuse resistant properties when physically manipulated, or wherein the dosage form exhibits abuse resistant properties when physically manipulated and administered in a manner not consistent with oral dosing, or wherein the dosage form exhibits abuse resistant properties when administered in a manner intended to result in administration of the esketamine in a higher than therapeutic dose.

Aspect 2. The dosage form according to aspect 1, wherein when the dosage form is physically manipulated by crushing to form a population of particles, less than 15% of the population comprises a subpopulation of particles having a particle size of less than 75 μm.

Aspect 3. The dosage form according to any preceding aspect, wherein when the dosage form is physically manipulated by crushing to form a population of particles, less than 40 wt. % of the population of particles comprises a subpopulation of particles having a particle size of less than 106 μm, and wherein said subpopulation contains less than 10 wt. % base equivalent of the esketamine of said dosage form.

Aspect 4. The dosage form according to any preceding aspect, wherein when the dosage form is physically manipulated by crushing to form a population of particles, less than 35 wt. % comprises a subpopulation of particles having a particle size of 212-500 μm and containing less than 70 wt. % base equivalent of the esketamine of said dosage form.

Aspect 5. The dosage form according to any preceding aspect, wherein when the dosage form is physically manipulated by crushing to form a population of particles, less than 30 wt. % comprises a subpopulation of particles having a particle size of 106-212 μm and wherein the subpopulation of particles contains less than 20 wt. % base equivalent of the esketamine of said dosage form.

Aspect 6. The dosage form according to aspect 1, wherein the dosage form exhibits one or more of the abuse resistant properties when the dosage form is physically manipulated by crushing and subsequent heating prior to the administration in a manner not consistent with oral dosing or in a manner intended to result in administration of the esketamine in a higher than therapeutic dose.

Aspect 7. The dosage form according to aspect 6, wherein the heating comprises subjecting the physically manipulated dosage form to a temperature of about 200° C.-300° C.

Aspect 8. The dosage form according to aspect 6 or aspect 7, wherein the physically manipulated dosage form is heated for at least one minute.

Aspect 9. The dosage form according to aspect 7 or aspect 8, wherein the heated, physically manipulated dosage form releases less esketamine (base equivalent) after incubation in water or 0.1 N HCl for up to 18 hours, as compared to the release of esketamine from a physically manipulated dosage form control that has not been heated prior to incubation in water or 0.1 N HCl for up to 18 hours.

Aspect 10. The dosage for according to aspect 7 or aspect 8, wherein the heated, physically manipulated dosage form releases at least 20 wt. % less esketamine (base equivalent), as compared to the release of esketamine (base equivalent) from a physically manipulated dosage form control that has not been heated prior to incubation in water or 0.1 N HCl for up to 18 hours.

Aspect 11. The dosage form according to any one of the preceding aspects, wherein upon physically manipulating the dosage form by crushing, the physically manipulated dosage form exhibits less than 5 wt. % the esketamine diffusion of powdered pure esketamine or a pharmaceutically acceptable salt thereof, over 60 minutes across a membrane having a molecular weight cutoff of 12-14 kD from a receptor chamber containing a phosphate buffer at pH 6.4 and maintained at 37° C.

Aspect 12. The dosage form according to any one of the preceding aspects, wherein upon physically manipulating the dosage form by crushing, the physically manipulated dosage form exhibits less esketamine diffusion across nasal membranes of a human subject when nasally insufflated by the subject, relative to a solution of 140 mg/ml esketamine (base equivalent) in pH 4.5 citrate buffer.

Aspect 13. The dosage form according to aspect 12, wherein upon physically manipulating the dosage form by crushing, the physically manipulated dosage form exhibits less than 5% the relative esketamine diffusion of a solution of 140 mg/ml esketamine (base equivalent) in pH 4.5 citrate buffer, over 60 minutes across a membrane having a molecular weight cutoff of 12-14 kD from a receptor chamber containing a phosphate buffer at pH 6.4 and maintained at 37° C.

Aspect 14. The dosage form according to any one of the preceding aspects, wherein upon physically manipulating the dosage form by crushing, the absorption of esketamine from the physically manipulated dosage form over 60 minutes across a membrane having a molecular weight cutoff of 12-14 kD from a receptor chamber containing a phosphate buffer at pH 6.4 and maintained at 37° C. is less than 20%.

Aspect 15. The dosage form according to any one of the preceding aspects, wherein the dosage is in a compressed tablet form.

Aspect 16. The dosage form according to any one of the preceding aspects, wherein the dosage form further comprises a second population of core-shell particles that do not contain an active pharmaceutical layer.

Aspect 17. The dosage form according to aspect 16, wherein each of the core-shell particles of the second population comprise a core that includes a gelling polymer and a wax, and at least one layer surrounding the core, the at least one layer comprising a pH-sensitive film comprising a pH-sensitive polymer that is insoluble in water at a pH greater than 5.

Aspect 18. The dosage form according to any one of the preceding aspects, wherein the core of each of the core-shell particles of the first population does not include a sugar sphere or an active pharmaceutical ingredient.

Aspect 19. The dosage form according to any one of the preceding aspects, wherein the gelling polymer in the core of the core-shell particles of the first population is selected from the group consisting of ethylcellulose, cellulose acetate, cellulose acetate propionate, cellulose acetate butyrate, cellulose acetate phthalate, cellulose triacetate, cellulose ether, cellulose ester, cellulose ester ether, cellulose, hydroxypropyl methyl cellulose, hydroxy methyl cellulose, methyl cellulose, hydroxyethylmethyl cellulose, sodium carboxymethyl cellulose, a carbomer polymer, polyethylene oxide, and combinations thereof.

Aspect 20. The dosage form according to aspect 19, wherein the gelling polymer in the core of the core-shell particles of the first population is hydroxypropyl methyl cellulose.

Aspect 21. The dosage form according to any one of the preceding aspects, wherein the wax in the core of the core-shell particles of the first population is a fatty alcohol that is selected from glycerol behenate, glycerol palmitostearate, glycerol monostearate, and stearoyl macroglycerides.

Aspect 22. The dosage form according any one of the preceding aspects, wherein the pH-sensitive polymer in the core-shell particles of the first population is a copolymer of dimethyl aminoethyl methacrylate, butyl methacrylate, and methyl methacrylate monomers.

Aspect 23. The dosage form according to any one of the preceding aspects, wherein the supratherapeutic dose is five or more dosage form units.

Aspect 24. The dosage form according to any one of the preceding aspects, wherein the supratherapeutic dose is 10 dosage form units.

Aspect 25. The dosage form according any one of the preceding aspects, wherein supratherapeutic doses of said dosage form produce a gel in 15 minutes or less, following exposure to an aqueous medium comprising 0.025 N HCl and 70 mM NaCl at 37° C.

Aspect 26. The dosage form according to aspect 25, wherein when a dual screen apparatus comprising a top screen and a bottom screen is used to extract at least a portion of said gel from said medium, a first quantity of the gel adheres to a lower surface of the top screen of the apparatus and a second quantity of the gel adheres to a upper surface of the bottom screen of the apparatus, wherein the vertical thickness of the second quantity is at least twice the vertical thickness of the first quantity.

Aspect 27. The dosage form according to aspect 25, wherein said gel is substantially uniformly dispersed within said medium.

Aspect 28. The dosage form according to any one of the preceding aspects comprising esketamine HCl.

Aspect 29. An oral tablet for the administration of esketamine to a subject comprising:

a total weight of not less than 800 mg, and having 40 mg of esketamine (base equivalent), the esketamine (base equivalent) representing less than 5.0% by weight of the total weight of the tablet, or a total weight of not less than 571 mg, and having 20 mg of esketamine (base equivalent), the esketamine (base equivalent) representing less than 3.5% by weight of the total weight of the tablet;

wherein the tablet exhibits an immediate release profile of esketamine having not less than 90% of the esketamine released in 60 minutes, and wherein the release profile is evaluated by dissolution of the tablet in 300 mL of 0.1N HCl media using USP II apparatus at 50 RPM paddle speed and 37° C.; and wherein the tablet exhibits an immediate release profile of the esketamine when administered to a human in therapeutic doses, and an extended release profile of the esketamine when administered to a human in supratherapeutic doses, or wherein the tablet exhibits abuse resistant properties when physically manipulated, or wherein the tablet exhibits abuse resistant properties when physically manipulated and administered in a manner not consistent with oral dosing, or wherein the tablet exhibits abuse resistant properties when administered in a manner intended to result in administration of the esketamine in a higher than therapeutic dose.

Aspect 30. The tablet according to aspect 29, wherein when the tablet is physically manipulated by crushing to form a population of particles, less than 15% of the population comprises a subpopulation of particles having a particle size of less than 75 μm.

Aspect 31. The tablet according to aspect 29 or 30, wherein when the tablet is physically manipulated by crushing to form a population of particles, less than 40 wt. % of the population of particles comprises a subpopulation of particles having a particle size of less than 106 μm, and wherein said subpopulation contains less than 10 wt. % base equivalent of the esketamine of said tablet.

Aspect 32. The tablet according to any one of aspects 29 to 31, wherein when the tablet is physically manipulated by crushing to form a population of particles, less than 35 wt. % comprises a subpopulation of particles having a particle size of 212-500 μm and containing less than 70 wt. % base equivalent of the esketamine of said tablet.

Aspect 33. The tablet according to anyone of aspects 29 to 32, wherein when the tablet is physically manipulated by crushing to form a population of particles, less than 30 wt. % comprises a subpopulation of particles having a particle size of 106-212 μm and wherein the subpopulation of particles contains less than 20 wt. % base equivalent of the esketamine of said tablet.

Aspect 34. The tablet according to aspect 29, wherein the tablet exhibits one or more of the abuse resistant properties when the tablet is physically manipulated by crushing and subsequent heating prior to the administration in a manner not consistent with oral dosing or in a manner intended to result in administration of the esketamine in a higher than therapeutic dose.

Aspect 35. The tablet according to aspect 34, wherein the heating comprises subjecting the physically manipulated tablet to a temperature of about 200° C.-300° C.

Aspect 36. The tablet according to aspect 34 or aspect 35, wherein the physically manipulated tablet is heated for at least one minute.

Aspect 37. The tablet according to aspect 34 or aspect 35, wherein the heated, physically manipulated tablet releases less esketamine (base equivalent) after incubation in water or 0.1 N HCl for up to 18 hours, as compared to the release of esketamine from a physically manipulated tablet control that has not been heated prior to incubation in water or 0.1 N HCl for up to 18 hours.

Aspect 38. The tablet according to aspect 34 or aspect 35, wherein the heated, physically manipulated tablet releases at least 20 wt. % less esketamine (base equivalent), as compared to the release of esketamine (base equivalent) from a physically manipulated tablet control that has not been heated prior to incubation in water or 0.1 N HCl for up to 18 hours.

Aspect 39. The tablet according to any one of aspects 29 to 38, wherein upon physically manipulating the tablet by crushing, the physically manipulated tablet exhibits less than 5 wt. % the esketamine diffusion of powdered pure esketamine or a pharmaceutically acceptable salt thereof, over 60 minutes across a membrane having a molecular weight cutoff of 12-14 kD from a receptor chamber containing a phosphate buffer at pH 6.4 and maintained at 37° C.

Aspect 40. The tablet according to any one of aspects 29 to 39, wherein upon physically manipulating the tablet by crushing, the physically manipulated tablet exhibits less esketamine diffusion across nasal membranes of a human subject when nasally insufflated by the subject, relative to a solution of 140 mg/ml esketamine (base equivalent) in pH 4.5 citrate buffer.

Aspect 41. The tablet according to aspect 40, wherein upon physically manipulating the tablet by crushing, the physically manipulated tablet exhibits less than 5% the relative esketamine diffusion of a solution of 140 mg/ml esketamine (base equivalent) in pH 4.5 citrate buffer, over 60 minutes across a membrane having a molecular weight cutoff of 12-14 kD from a receptor chamber containing a phosphate buffer at pH 6.4 and maintained at 37° C.

Aspect 42. The tablet according to any one of aspects 29 to 41, wherein upon physically manipulating the tablet by crushing, the absorption of esketamine from the physically manipulated tablet over 60 minutes across a membrane having a molecular weight cutoff of 12-14 kD from a receptor chamber containing a phosphate buffer at pH 6.4 and maintained at 37° C. is less than 20%.

Aspect 43. The dosage form according to any one of aspects 29 to 42 comprising esketamine HCl.

Aspect 44. An oral dosage form comprising:

(i) a first population of core-shell particles, each of the core-shell particles of the first population comprising a core that includes a gelling polymer and a wax;

an active pharmaceutical layer surrounding the core, the active pharmaceutical layer comprising esketamine; and at least one layer surrounding the active pharmaceutical layer, the at least one layer comprising a pH-sensitive film comprising a pH-sensitive polymer that is insoluble in water at a pH greater than 5;

and, (ii) a matrix comprising a carbomer gelling polymer and sodium bicarbonate, wherein the carbomer gelling polymer and sodium bicarbonate are present in a ratio by weight percentage of about 2:2 based on the total weight of the dosage form;

wherein the dosage form exhibits an immediate release profile of the esketamine when administered to a human in therapeutic doses, and an extended release profile of the esketamine when administered to a human in supratherapeutic doses.

Aspect 45. The dosage form according to aspect 44, wherein the dosage is in a compressed tablet form.

Aspect 46. The dosage form according to aspect 44 or aspect 45, wherein the dosage form further comprises a second population of core-shell particles that do not contain an active pharmaceutical layer.

Aspect 47. The dosage form according to aspect 46, wherein each of the core-shell particles of the second population comprise a core that includes a gelling polymer and a wax, and at least one layer surrounding the core, the at least one layer comprising a pH-sensitive film comprising a pH-sensitive polymer that is insoluble in water at a pH greater than 5.

Aspect 48. The dosage form according to any one of aspects 44-47, wherein the core of each of the core-shell particles of the first population does not include a sugar sphere or an active pharmaceutical ingredient.

Aspect 49. The dosage form according to any one of aspects 44-48, wherein the gelling polymer in the core of the core-shell particles of the first population is selected from the group consisting of ethylcellulose, cellulose acetate, cellulose acetate propionate, cellulose acetate butyrate, cellulose acetate phthalate, cellulose triacetate, cellulose ether, cellulose ester, cellulose ester ether, cellulose, hydroxypropyl methyl cellulose, hydroxy methyl cellulose, methyl cellulose, hydroxyethylmethyl cellulose, sodium carboxymethyl cellulose, a carbomer polymer, polyethylene oxide, and combinations thereof.

Aspect 50. The dosage form according to aspect 49, wherein the gelling polymer in the core of the core-shell particles of the first population is hydroxypropyl methyl cellulose.

Aspect 51. The dosage form according to any one of aspects 44-50, wherein the wax in the core of the core-shell particles of the first population is a fatty alcohol that is selected from glycerol behenate, glycerol palmitostearate, glycerol monostearate, and stearoyl macroglycerides.

Aspect 52. The dosage form according any one of aspects 44-51, wherein the pH-sensitive polymer in the core-shell particles of the first population is a copolymer of dimethyl aminoethyl methacrylate, butyl methacrylate, and methyl methacrylate monomers.

Aspect 53. The dosage form according to any one of aspects 44-52, wherein the supratherapeutic dose is five or more dosage form units.

Aspect 54. The dosage form according to any one of aspects 44-53, wherein the supratherapeutic dose is 10 dosage form units.

Aspect 55. The dosage form according any one of aspects 44-54, wherein supratherapeutic doses of said dosage form produce a gel in 15 minutes or less, following exposure to an aqueous medium comprising 0.025 N HCl and 70 mM NaCl at 37° C.

Aspect 56. The dosage form according to aspect 55, wherein when a dual screen apparatus comprising a top screen and a bottom screen is used to extract at least a portion of said gel from said medium, a first quantity of the gel adheres to a lower surface of the top screen of the apparatus and a second quantity of the gel adheres to a upper surface of the bottom screen of the apparatus, wherein the vertical thickness of the second quantity is at least twice the vertical thickness of the first quantity.

Aspect 57. The dosage form according to aspect 56, wherein said gel is substantially uniformly dispersed within said medium.

Aspect 58. The dosage form according to any one of aspects 44-57 comprising esketamine HCl.

Aspect 59. A method of reducing the potential for abuse by a human of an active pharmaceutical ingredient comprising esketamine, comprising providing to the human a dosage form according to any one of aspects 1-58.

Aspect 60. A method of reducing the potential for abuse by a human of an active pharmaceutical ingredient comprising esketamine by simultaneous oral ingestion of multiple dosage units comprising the active pharmaceutical ingredient, comprising providing to the human a dosage form according to any one of aspects 1-58.

Aspect 61. A method for treating or preventing pain or discomfort in a subject in need thereof by administering to the subject a dosage form according to any one of aspects 1-58.

Aspect 62. A method for treating depression in a subject in need thereof by administering to the subject a dosage form according to any one of aspects 1-58.

Aspect 63. A method of reducing the potential for abuse by nasal insufflation by a human of an active pharmaceutical ingredient comprising esketamine, comprising providing to the human a dosage form according to any one of aspects 1-58.

The following non-limiting examples show various dosage forms as described herein. The described and exemplified dosage forms can be made from methods that include granulating, coating, and compressing steps as follows.

Example 1—General Procedure for Preparation of Tablet Dosage Form

Granulation

1. Glyceryl behenate and hypromellose K100M were dry mixed in a high shear granulator. Hydroalcoholic solution of ethylcellulose was added. Alternatively, the granulation can be produced through top spraying the hydroalcoholic solution in a fluid bed granulator. Optionally, a portion of the ethyl cellulose, for example from about 10 to about 50% by weight, or from about 10 to about 40% by weight, or from about 30 to about 40% by weight, or from about 15 to about 30% by weight, may be dry mixed with the glyceryl behenate and hypromellose K100M prior to adding the hydroalcoholic solution containing the balance of the ethyl cellulose.

Alternative approach when API is included in the core: Glyceryl behenate and hypromellose K100M and API are dry mixed in a high shear granulator. Hydroalcoholic solution of ethylcellulose is added. Alternatively, the granulation can be produced through top spraying the hydroalcoholic solution in a fluid bed granulator. Optionally, a portion of the ethyl cellulose, for example from about 10 to about 50% by weight, or from about 10 to about 40% by weight, or from about 15 to about 30% by weight, is dry mixed with the glyceryl behenate and hypromellose K100M prior to adding the hydroalcoholic solution containing the balance of the ethyl cellulose.

2. The granules were then wet milled using a size reduction mill (Granumill) and then dried using a fluid bed, and optionally screened. Optionally, the granules were subsequently then dry milled using a size reduction mill.

Layering

3. The polymer granules were then layered using Wurster fluid bed layering process with esketamine and hypromellose K100M (or alternatively, granulated using high shear granulation or top spray fluid bed granulation process).

Alternative approach when API is not in the coated granule: the layering step is omitted and the coating of Step 4 below is applied to the granulate prepared in Step 1.

Coating

4. The layered granules of Step 3 (or alternatively, when the coated granule will not contain API, the granules prepared in Step 1) were then coated using a fluid bed coater equipped with a Wurster insert (bottom spray assembly) with ethanolic suspension of Eudragit E100 copolymer and magnesium stearate. Coated particles were then screened and blended.

Blending and Tablet Compression

The blending, compression and bottling process for esketamine tablets manufactured using the coated intermediate is as follows:

1. The API-containing coated granules, crospovidone, Carbopol® 71G, sodium bicarbonate, mannitol, microcrystalline cellulose, optionally, coated granules containing no API, optionally, a glidant such as colloidal silicon dioxide, and optionally a desired colorant, were then added to the blender and mixed.
2. Magnesium stearate (and optionally colorant) was then added to the blender and mixed. The blend was compressed into tablets using a rotary tablet press.

Example 2—Preparation of Polymer Granules

Granules were manufactured in a high shear granulator, where hypromellose and glyceryl behenate were dry mixed for 3 minutes. Then, either a 10% hydroalcoholic solution of ethylcellulose N10 was slowly added while maintaining the granulator impeller and chopper speed at pre-selected values that provide enough shear for granule formation and growth or 1 part ethylcellulose N10 was included in the dry mix and 2 parts of a 10% 25:65 hydroalcoholic solution of ethylcellulose N10 were slowly added while maintaining the granulator impeller and chopper speed at pre-selected values. Solution addition was continued until all the ethylcellulose was added. The granules were then wet milled using a size reduction mill (Granumill or Vector mixer) and were subsequently loaded into fluid bed for drying followed, in certain cases, by the granules being dry milled using a size reduction mill (Fitzmill). Table 1, below, provides the relative proportions of the reagents used for forming the granules.

TABLE 1

Components for granule formulation

| Component | % w/w |
|---|---|
| Hypromellose K100M | 60.09 |
| Glyceryl behenate | 25.75 |
| Ethylcellulose N-10 | 14.16 |
| TOTAL | 100 |

The prepared granules were then layered in a bottom spray fluid bed coater with an aqueous coating dispersion esketamine HCl and hypromellose 2910.

TABLE 2

Components for coating dispersion used for coating of polymer granules

| Component within Coating Dispersion | % w/w | g/Batch, 19.5% Esketamine | g/Batch, 39.1% Esketamine |
|---|---|---|---|
| Esketamine HCl | 13 | 195 | 390 |
| Hypromellose 2910 | 5 | 75 | 150 |
| Purified Water | 82 | 1260 | 2520 |
| TOTAL | 100 | 1500 | 3000 |

TABLE 3

Components for layered granule formulation, 19.5% or 39.1% Esketamine HCl

| Layered Granule | % w/w | g/Batch, 19.5% Esketamine | g/Batch, 39.1% Esketamine |
|---|---|---|---|
| Polymer granules from Table 1 | 68.83 | 596.1 | 325.4 |

TABLE 3-continued

Components for layered granule formulation, 19.5% or 39.1% Esketamine HCl

| Layered Granule | % w/w | g/Batch, 19.5% Esketamine | g/Batch, 39.1% Esketamine |
|---|---|---|---|
| Solids from Coating Dispersion from Table 2 | 31.17 | 270 | 540 |
| TOTAL | 100 | 866.1 | 865.4 |

The esketamine HCl layered granules were then coated in a bottom spray fluid bed coater with the alcoholic suspension of Eudragit E-100 copolymer and magnesium stearate. The resulting coated granules (containing either 16% or 32% esketamine HCl) were subsequently used for further blending and compression process.

TABLE 4

Components for coating dispersion used for coating of Esketamine HCl layered granules

| Component within Coating Dispersion | % w/w | g/Batch, 19.5% Esketamine | g/Batch, 39.1% Esketamine |
|---|---|---|---|
| Eudragit E100 | 16.67 | 102 | 102 |
| Magnesium Stearate | 8.33 | 51 | 51 |
| Alcohol USP | 75 | 489 | 489 |
| TOTAL | 100 | 612 | 612 |

TABLE 5

Components for coated esketamine granules containing 16% Esketamine HCl

| Component | % w/w |
|---|---|
| Esketamine HCl layered granules, 19.5% | 82 |
| Solids from coating dispersion from Table 4 | 18 |
| TOTAL | 100 |

TABLE 6

Components for coated esketamine granules containing 32% Esketamine HCl

| Component | % w/w |
|---|---|
| Esketamine HCl layered granules, 39.1% | 82 |
| Solids from coating dispersion from Table 4 | 18 |
| TOTAL | 100 |

Coated polymer granules that did not contain esketamine HCl were formed using the polymer granules of Table 1.

In order to form the coated polymer granules, polymer granules of Table 1 were coated in a bottom spray fluid bed coater with the alcoholic suspension of Eudragit E-100 copolymer and magnesium stearate (Table 7). The resulting coated granules were, along with the coated esketamine granules, subsequently used for further blending and compression process.

TABLE 7

Components for coating dispersion used for coating of polymer granules

| Component within Coating Dispersion | % w/w | g/Batch |
|---|---|---|
| Eudragit E100 | 16.67 | 366 |
| Magnesium Stearate | 8.33 | 182.8 |
| Alcohol USP | 75 | 1676 |
| TOTAL | 100 | 2194.8 |

TABLE 8

Components for coated polymer granules (no esketamine)

| Component | % w/w |
|---|---|
| Polymer granules from Table 1 | 50 |
| Solids from coating dispersion from Table 7 | 50 |
| TOTAL | 100 |

Example 3—Esketamine HCl Tablet Formulation

The coated granules prepared according to Example 2, supra, were mixed with excipients as listed in Tables 9-13, below, and blended in a V-blender for 30 minutes. Both coated esketamine granules (Tables 4/5 or 4/6) and coated polymer granules (Tables 7/8) were included as indicated. Magnesium stearate was then added to lubricate the blend and the mixture was blended for an additional 5 minutes prior to compressing into esketamine HCl tablets.

TABLE 9

Tablets, 100 mg Esketamine

| | % w/w |
|---|---|
| Coated Esketamine Granules, 33% | 30.77 |
| Coated Polymer Granules from Tables 7/8 | 17.6 |
| Mannitol (Mannogem EZ) | 13.39 |
| Crospovidone (Polyplasdone XL) | 20 |
| Microcrystalline Cellulose (Avicel PH113) | 13 |
| Carbomer (Carbopol ® 71G) | 2 |
| Sodium Bicarbonate | 2 |
| Colloidal silicon dioxide | 0.2 |
| Magnesium stearate | 1 |
| Total | 100 |

TABLE 10

Tablets, 40 mg Esketamine

| | % | mg/Tab | g/batch |
|---|---|---|---|
| Coated Esketamine Granules, 16.0% | 25.00 | 250.0 | 2500 |
| Coated Polymer Granules | 7.06 | 70.6 | 706 |
| Mannitol (Mannogem EZ) | 29.74 | 297.4 | 2974 |
| Crospovidone (Polyplasdone XL) | 20 | 200 | 2000 |
| Microcrystalline Cellulose (Avicel PH113) | 13 | 130 | 1300 |
| Carbomer (Carbopol ® 71G) | 2 | 20 | 200 |
| Sodium Bicarbonate | 2 | 20 | 200 |

TABLE 10-continued

| Tablets, 40 mg Esketamine | | | |
|---|---|---|---|
| | % | mg/Tab | g/batch |
| Colloidal silicon Dioxide | 0.2 | 2 | 20 |
| Magnesium stearate | 1 | 10 | 100 |
| Total | 100 | 1000 | 10000 |

TABLE 11

| Tablets, 20 mg Esketamine | | | |
|---|---|---|---|
| | % | mg/Tab | g/batch |
| Coated Esketamine Granules, 16.0% | 12.5 | 125 | 1250* |
| Coated Polymer Granules | 21.17 | 211.7 | 2117* |
| Mannitol (Mannogem EZ) | 28.13 | 281.3 | 2813 |
| Crospovidone (Polyplasdone XL) | 20 | 200 | 2000 |
| Microcrystalline Cellulose (Avicel PH113) | 13 | 130 | 1300 |
| Carbomer (Carbopol ® 71G) | 2 | 20 | 200 |
| Sodium Bicarbonate | 2 | 20 | 200 |
| Colloidal silicon Dioxide | 0.2 | 2 | 20 |
| Magnesium stearate | 1 | 10 | 100 |
| Total | 100 | 1000 | 10000 |
| *Polymer granules required | | | 1766 (707 + 1059) |

TABLE 12

| Tablets, 10 mg Esketamine | | | |
|---|---|---|---|
| | % | mg/Tab | g/batch |
| Coated Esketamine Granules, 16.0% | 6.25 | 62.5 | 625* |
| Coated Polymer Granules | 27.42 | 274.2 | 2742* |
| Mannitol (Mannogem EZ) | 28.13 | 281.3 | 2813 |
| Crospovidone (Polyplasdone XL) | 20 | 200 | 2000 |
| Microcrystalline Cellulose (Avicel PH113) | 13 | 130 | 1300 |
| Carbomer (Carbopol ® 71G) | 2 | 20 | 200 |
| Sodium Bicarbonate | 2 | 20 | 200 |
| Colloidal silicon Dioxide | 0.2 | 2 | 20 |
| Magnesium stearate | 1 | 10 | 100 |
| Total | 100 | 1000 | 10000 |
| *Polymer granules required | | | 1725 (354 + 1371) |

TABLE 13

| Tablets, 5 mg Esketamine | | | |
|---|---|---|---|
| | % | mg/Tab | g/batch |
| Coated Esketamine Granules, 16.0% | 3.125 | 31.25 | 312.5* |
| Coated Polymer Granules | 30.545 | 305.45 | 3054.5* |
| Mannitol (Mannogem EZ) | 28.13 | 281.3 | 2813 |
| Crospovidone (Polyplasdone XL) | 20 | 200 | 2000 |
| Microcrystalline Cellulose (Avicel ® PH113) | 13 | 130 | 1300 |
| Carbomer (Carbopol ® 71G) | 2 | 20 | 200 |
| Sodium Bicarbonate | 2 | 20 | 200 |

TABLE 13-continued

| Tablets, 5 mg Esketamine | | | |
|---|---|---|---|
| | % | mg/Tab | g/batch |
| Colloidal silicon Dioxide | 0.2 | 2 | 20 |
| Magnesium stearate | 1 | 10 | 100 |
| Total | 100 | 1000 | 10000 |
| *Polymer granules required | | | 1704 (177 + 1527) |

Example 4—Preparation of Comparative Embodiment

Comparative 20 and 100 mg esketamine HCl embodiments having a matrix containing carbomer gelling polymer and sodium bicarbonate in a ratio of 2:10 percentage by weight, based on the total weight of the dosage form.

Esketamine HCl layered granules, as described in Example 2, were coated in a bottom spray fluid bed coater with the alcoholic suspension of Eudragit E-100 copolymer and magnesium stearate. The resulting coated granules (containing 33% esketamine HCl) were subsequently used for further blending and compression process.

The coated granules were mixed with excipients as listed in Tables 14 and 15, below, and blended in a V-blender for 30 minutes. Magnesium stearate was then added to lubricate the blend and the mixture was blended for an additional 5 minutes prior to compressing into esketamine HCl tablets.

TABLE 14

| 20 mg esketamine tablet formulations with 2:10 carbomer to sodium bicarbonate ratio | |
|---|---|
| | % w/w |
| Coated Esketamine Granules, 16% | 11.7 |
| Coated Polymer Granules from Tables 7/8 | 22.1 |
| Mannitol (Mannogem EZ) | 20 |
| Crospovidone (Polyplasdone XL) | 20 |
| Microcrystalline Cellulose (Avicel PH113) | 13 |
| Carbomer (Carbopol ® 71G) | 2 |
| Sodium Bicarbonate | 10 |
| Colloidal silicon dioxide | 0.2 |
| Magnesium stearate | 1 |
| Total | 100 |

TABLE 15

| 100 mg esketamine tablet formulations with 2:10 carbomer to sodium bicarbonate ratio | |
|---|---|
| | % w/w |
| Coated Esketamine Granules, 33% | 30.77 |
| Coated Polymer Granules from Tables 7/8 | 17.6 |
| Mannitol (Mannogem EZ) | 5.37 |
| Crospovidone (Polyplasdone XL) | 20 |
| Microcrystalline Cellulose (Avicel PH113) | 13 |
| Carbomer (Carbopol ® 71G) | 2 |
| Sodium Bicarbonate | 10 |
| Colloidal silicon dioxide | 0.2 |
| Magnesium stearate | 1 |
| Red Iron Oxide | 0.06 |
| Total | 100 |

Example 5—Evaluation of Esketamine Release

Tablet dosage forms according to the present disclosure (100 mg esketamine HCl—see Table 9, supra) were tested for single-tablet dissolution by depositing a single tablet into a USP II apparatus containing 500 mL of deaerated 0.01N hydrochloric acid medium and a paddle speed set at 50 RPM.

Also tested were comparative 100 mg esketamine HCl embodiments having a matrix containing carbomer gelling polymer and sodium bicarbonate in a ratio of 2:10 percentage by weight, based on the total weight of the dosage form, that were prepared as described in Example 4, supra.

FIG. 4 shows the results of single-tablet dissolution testing of the inventive 2:2 dosage form (triangles) and the comparative 2:10 dosage form (squares). Both embodiments displayed complete release within 15 minutes following deposition into the testing apparatus.

The respective dosage forms were also tested for the ability to provide multiple table abuse resistance ("MTAR") when 12 individual dosage units are deposited into a USP II apparatus containing 400 mL of deaerated 0.1N hydrochloric acid medium and a paddle speed set at 50 RPM. These conditions are intended to simulate oral ingestion by a potential abuser of a beverage with a supratherapeutic dose of the dosage forms.

FIG. 5 shows the results of multiple-tablet dissolution testing of the inventive 2:2 dosage form (triangles) and the comparative 2:10 dosage form (squares). Also tested was a second comparative dosage form containing 10 mg hydrocodone bitartrate and 325 mg acetaminophen (diamonds) as disclosed in WO 2016/094358 (see Example 23 on pages 81-82). The inventive 2:2 dosage form displayed release of less than 60% of the active agent 30 minutes following deposition into the testing apparatus, and no more than 80% of the active agent 240 minutes following deposition into the testing apparatus.

Example 6—QbD Analysis

An evaluation was conducted to identify the optimized formulation with maximized immediate release (IR) and MTAR dissolution properties. Sixteen different formulations varying the weight ratios of four variables (carbopol, sodium bicarbonate, crospovidone, coated polymer granules) in 100 mg API formulations were prepared according to the ranges disclosed in Table 16.

TABLE 16

| Ranges of Ingredients Evaluated | |
|---|---|
| Ingredient | % w/w |
| Carbopol | 1-5 |
| Sodium bicarbonate | 1-4 |
| Crospovidone | 10-30 |
| Coated polymer granules | 1.82-28.82 |

The formulations were each assayed in dissolution media to assess the release at 30 minutes for a single tablet (maximal IR) and the release for a multiple tablet at 60 minutes (minimal MTAR). The results are disclosed in Table 17a (immediate release) and 17b (MTAR).

TABLE 17a

| Fastest Release At 30 Minutes | | |
|---|---|---|
| Fastest formulation (ranking) | % Carbopol | % Sodium Bicarbonate |
| 1 | 1.2 | 2.0 |
| 2 | 1.8 | 1.0 |
| 3 | 1.1 | 3.0 |
| 4 | 2.0 | 2.0 |
| 5 | 1.3 | 4.0 |
| . . . 15 | 4.8 | 3.2 |

TABLE 17b

| minimum release at 60 minutes | | |
|---|---|---|
| Slowest formulation (ranking) | % Carbopol | % Sodium Bicarbonate |
| 1 | 1.1 | 3.0 |
| 2 | 1.3 | 4.0 |
| 3 | 3.9 | 3.6 |
| 4 | 2.2 | 2.1 |
| 5 | 2.0 | 2.0 |
| . . . 10 | 4.8 | 3.2 |

The optimized formulations with the overall desirability maximized combining the contribution from IR and MTAR were analyzed based on a truncated 13 term model for MTAR and a 15 term model for IR with equal weightage to the two responses. The predicted optimized formulation is disclosed in Table 18.

TABLE 18

| Predicted Optimized Formulations | |
|---|---|
| Approach for Optimization | Maximize IR (15-term model) and minimize MTAR (13-term model) with equal weightage |
| Optimized formulation composition (% w/w) | |
| Carbopol | 1.02 |
| Sodium bicarbonate | 2.62 |

Example 7—Evaluation of Gel Characteristics

An evaluation was conducted to assess the quality of the gels that were formed when respective supratherapeutic doses of the inventive 2:2 weight percent dosage form and the comparative 1:2 and 2:10 weight percent dosage forms were exposed to dissolution medium.

In particular, a supratherapeutic dose consisting of 10 tablets of the inventive 2:2 weight percent dosage form of Example 3 (Table 9) was placed into an aqueous medium of 0.025 N HCl+70 mM NaCl at 37° C. The medium also contained a dual mesh screen featuring a horizontally-oriented circular top screen, a horizontally-oriented circular bottom screen, and a handle for lifting the dual mesh apparatus from the medium. Fifteen minutes after mixing the deposited supratherapeutic dose into the test medium, the dual mesh apparatus was removed from the medium and the characteristics of the gel were visually assessed.

The same procedure was performed with respect to a supratherapeutic dose of 10 tablets of the comparative 1:2 and 2:10 dosage forms of Table 19 and Example 4 (Table 15), and the characteristics of the resulting gel were assessed and compared to the gel resulting from the supratherapeutic dose of the 2:2 inventive dosage form.

TABLE 19

| 100 Mg Esketamine Tablet Formulations With 1:2 Carbomer To Sodium Bicarbonate Ratio | % w/w |
|---|---|
| Coated Esketamine Granules, 32% | 29.94 |
| Coated Polymer Granules from Tables 7/8 | 16.82 |
| Mannitol (Mannogem EZ) | 16.04 |
| Crospovidone (Polyplasdone XL) | 20 |
| Microcrystalline Cellulose (Avicel PH113) | 13 |
| Carbomer (Carbopol ® 71G) | 1 |
| Sodium Bicarbonate | 2 |
| Colloidal silicon dioxide | 0.2 |
| Magnesium stearate | 1 |
| Total | 100 |

Figure 6:
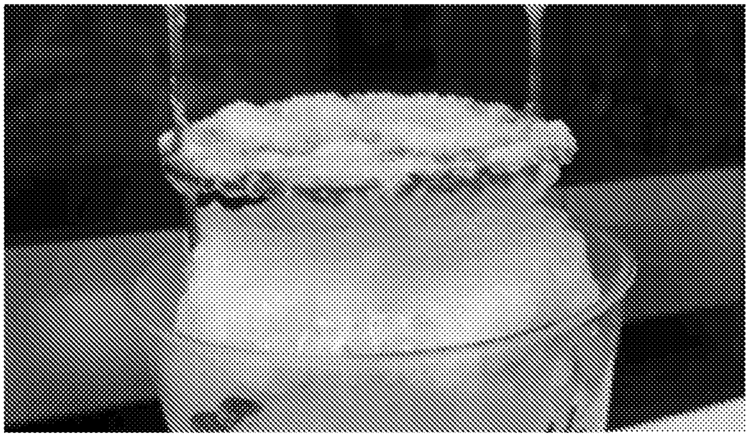
FIG. 6 provides an image of a dual screen apparatus that was used to test a supratherapeutic dose of an inventive dosage form with gel retained on the screens.

All samples formed gels in under 15 minutes. Visual inspection of the dual screen apparatus that was lifted from the medium into which the supratherapeutic dose of the 2:2 inventive dosage form was tested revealed that the gel from the supratherapeutic dose (i) was retained on the upper surface of the top screen in a very thin layer; (ii) was retained on the lower surface of the top screen in a thin layer; (iii) was retained on the upper surface of the bottom screen in a robust layer that was at least twice as thick (vertically) as the layer that was retained on the lower surface of the top screen; and, (iv) overall, represented a good quality gel that was not overly rigid, nor was it watery (was retained on the bottom screen and did not flow through the screen when the apparatus was lifted from the medium). FIG. 6 provides an image of the dual screen apparatus that was used to test the supratherapeutic dose of the 2:2 inventive dosage form with gel retained on the screens as described above.

Figure 7:
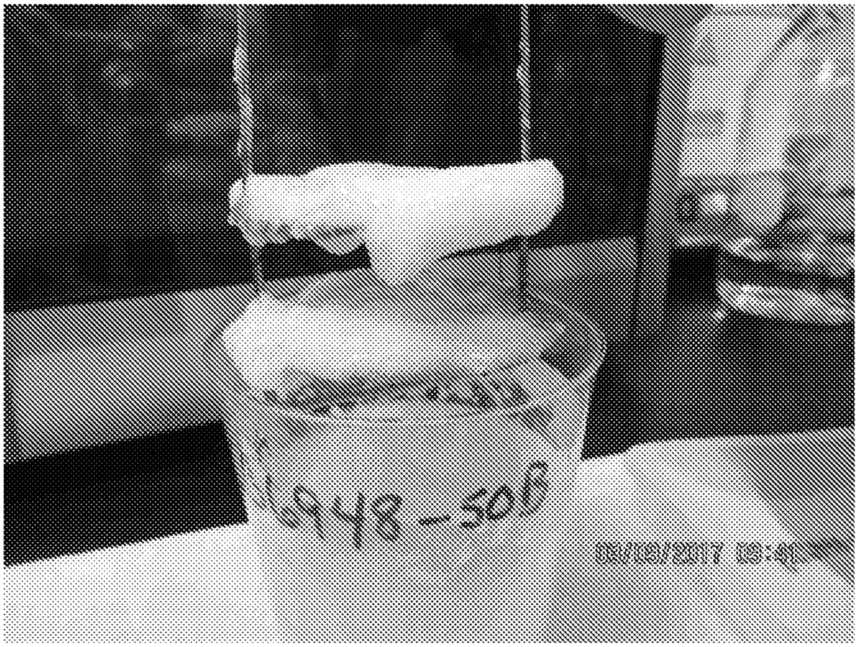
FIG. 7 provides an image of a dual screen apparatus that was used to test a supratherapeutic dose of a comparative dosage form with gel retained on the screens.

Visual inspection of the dual screen apparatus that was lifted from the medium into which the supratherapeutic dose of the 1:2 comparative dosage form was tested revealed that the gel from the supratherapeutic dose (i) was retained on the upper surface of the top screen in a weak layer that was thinner than a layer that was retained on the upper surface of the bottom screen; (ii) was retained on the lower surface of the top screen in a thin layer; (iii) was not retained between the top and bottom screens; and, (iv) appeared to flow through the screens as a weak gel. FIG. 7 provides an image of the dual screen apparatus that was used to test the supratherapeutic dose of the 1:2 comparative dosage form with gel retained on the screens as described above.

Figure 8:
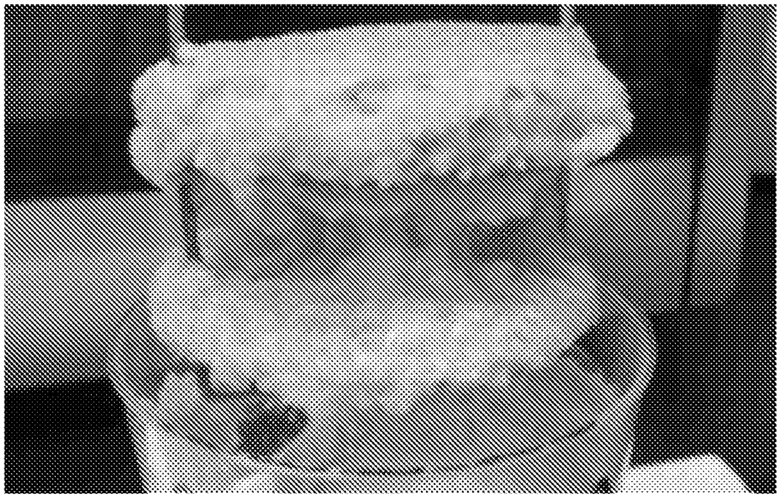
FIG. 8 provides an image of a dual screen apparatus that was used to test a supratherapeutic dose of a comparative dosage form with gel retained on the screens.

Visual inspection of the dual screen apparatus that was lifted from the medium into which the supratherapeutic dose of the 2:10 comparative dosage form was tested revealed that the gel from the supratherapeutic dose (i) was retained on the upper surface of the top screen in a robust layer that was thicker than a layer that was retained on the upper surface of the bottom screen; (ii) was retained on the lower surface of the top screen in a thin layer; (iii) was retained on the upper surface of the top screen in a layer that was not as thick as the layer that was retained on the upper surface of the top screen; (iv) included “runners” (portions of gel) between the layer of gel on the lower surface of the top screen and the layer of gel on the upper surface of the bottom screen, and, (v) overall, represented a rigid, thick gel. FIG. 8 provides an image of the dual screen apparatus that was used to test the supratherapeutic dose of the 2:10 comparative dosage form with gel retained on the screens as described above.

A further evaluation was conducted as to the quality of the gels that were formed when respective supratherapeutic doses of the inventive 2:2 dosage form and the comparative 2:10 dosage form were exposed to dissolution medium.

A supratherapeutic dose consisting of 10 tablets of the inventive 2:2 dosage forms of Example 3 (Table 9) was placed into an aqueous medium of 0.025 N HCl+70 mM NaCl at 37° C. The same procedure was performed in a second test vessel with respect to a supratherapeutic dose of 10 tablets of the comparative 2:10 dosage form of Example 4 (Table 18), and the characteristics of the material within the vessel were assessed and compared to the material within the vessel containing the supratherapeutic dose of the 2:2 inventive dosage form.

FIG. 9 provides an image of the gel resulting from the supratherapeutic dose of the inventive 2:2 dosage forms, suspended in the test medium. As shown, the gel/test medium mixture appeared turbid and opaque, indicating that the gel material was substantially homogeneously dispersed within the medium. There were no uneven concentrations of gel in any particular region of the medium (e.g., in the upper, middle, or lower portions of the medium within the test vessel), such as in the form of clumps, and likewise no regions without association between medium and gel, wherein medium is clearly visible in the absence of gel material. These results suggest that supratherapeutic doses of the inventive dosage form would provide good resistance to an attempt to extract drug from the supratherapeutic dose by combining it with a solvent and then either orally ingesting the mixture or attempting uptake of the mixture using a syringe, because of the ability of the resulting gel to entrap the drug within a consistent, uniform gel matrix, and due to the ability to resist uptake by or injection from a needle of a hypodermic syringe because of the thickness and uniformity of the gel matrix.

Figure 10:
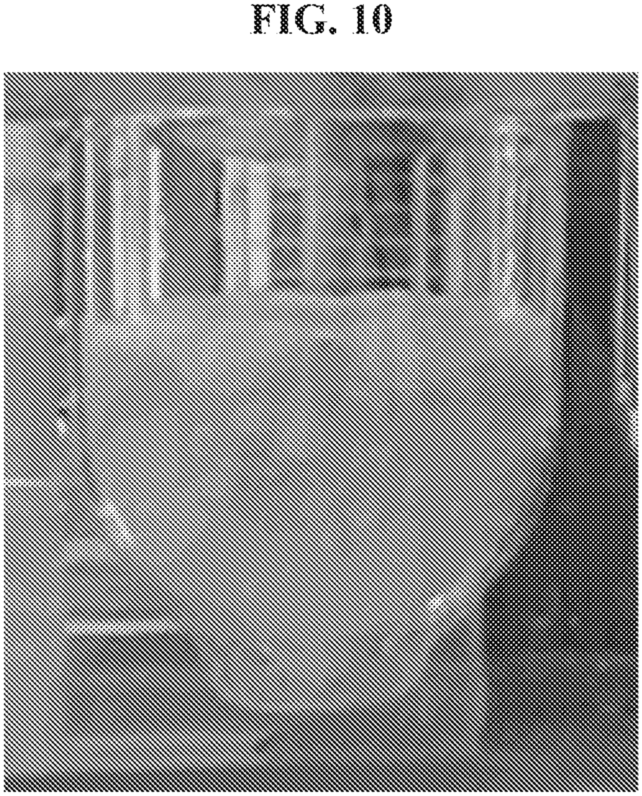
FIG. 10 provides an image of a gel resulting from a supratherapeutic dose of comparative dosage forms, suspended in a test medium.

FIG. 10 provides an image of the gel resulting from the supratherapeutic dose of the comparative 2:10 dosage forms, suspended in the test medium. As shown, the gel/test medium mixture was non-uniform, and included a concentration of gel material within the upper portion of the medium, indicating that the gel material was not uniformly dispersed within the medium. In fact, gel material was absent from a significant volume of the medium. Also apparent were clumps of gel and portions of medium that were clearly visible in the absence of gel material. These results suggest that supratherapeutic doses of the comparative dosage form would provide poor resistance to an attempt to extract drug from the supratherapeutic dose by combining it with a solvent and then either orally ingesting the mixture or attempting uptake of the mixture using a syringe, because of the likelihood of the presence of regions of the mixture of drug and solvent in which gel is absent (i.e., regions in which the solvent predominates), and from which drug could be readily extracted.

Example 8—Physical Manipulation Studies

Initial Analysis. A single 40 mg tablet of esketamine HCl of Example 3 was crushed using a mortar and pestle. The tablet was initially fractured by the gentle striking of the pestle, followed by rotation of the pestle against the tablet pieces. After visual inspection showed that no further particle size reduction was possible, the procedure was terminated. The sample was then collected onto a piece of (pre-tared on an analytical balance) 3×3 weigh paper by gently brushing the material from the mortar and weighed. 1000 μm and 500 μm sieves were stacked sequentially and set in a sieve shaker following which, the samples was transferred from the weigh paper by distributing it across the top sieve (1000 μm). Each sample was sieved for a total of 5 minutes during which for the first 60 seconds, the shaker was set to an amplitude of 80 Hz, and for the following 4 minutes, at an amplitude of 50 Hz. After sieving, each sieve was carefully removed and the weight of the sieve and manipulated material was recorded. The material from each sieve was then transferred into a tarred and labeled collection vessel and weighed. The procedure was repeated in triplicate and the results averaged to show an average manipulation time of 52 seconds, 99.7% weight recovery, 0.2% particle size above 1000 μm and 3.0% particle size between 500 and 1000 μm.

Advanced Analysis. A single 40 mg tablet of esketamine HCl of Example 3 was crushed using a mortar and pestle. The tablet was initially fractured by the gentle striking of the pestle, followed by rotation of the pestle against the tablet pieces for 52 seconds. The sample was then collected onto a piece of (pre-tared on an analytical balance) 3×3 weigh paper by gently brushing the material from the mortar and weighed. 1000 μm, 500 μm, 212 μm, 106 μm and 75 μm sieves were stacked sequentially and set in a sieve shaker following which, the samples was transferred from the weigh paper by distributing it across the top sieve (1000 μm). Each sample was sieved for a total of 5 minutes during which, for the first 60 seconds, the shaker was set to an amplitude of 80 Hz, and for the following 4 minutes, at an amplitude of 50 Hz. After sieving, each sieve was carefully removed and the weight of the sieve and manipulated material was recorded. The material from each sieve was the collected onto a piece of (pre-tared on an analytical balance) 3×3 weigh paper by gently brushing the material from the sieve and weighed. Sample fractions that resulted in 4% recovery or less were transferred into 20 mL scintillation vials, fractions that resulted in between 4% and 25% recovery were transferred into 125 mL Erlenmeyer Flasks and fractions that resulted in over 25% recovery were transferred into 250 mL Erlenmeyer Flasks. To each vessel with collected material, a calculated prorated volume of 0.1 N HCl (mass recovered on sieve]/[mass of manipulated material]*240 mL) was added. The sieve fraction solutions were then extracted overnight for a minimum of 15 hours at room temperature with agitation at 150 RPM following which, aliquots of the samples were prepared for LC-MS/MS analysis. The procedure was repeated in triplicate and the results averaged to show an average 98.8% weight recovery. The results per sieve fraction are shown in Table 20, below.

TABLE 20

Summary of results per sieve fraction

| Sieve fraction | Average % Particle Size Distribution | Average % esketamine recovery | Average % esketamine uniformity |
|---|---|---|---|
| >1000 μm | 0.3 | 0.1 | 0.8 |
| 500-1000 μm | 5.4 | 9.7 | 7.4 |
| 212-500 μm | 31.9 | 62.4 | 8.0 |
| 106-212 μm | 26.7 | 18.9 | 3.0 |
| 75-106 μm | 24.3 | 5.2 | 0.9 |
| <75 μm (pan) | 11.4 | 1.8 | 0.7 |

The preceding results demonstrate that the esketamine was not concentrated in any particular fraction of particle sizes, and in all fractions, the amount of esketamine was less than 10% and the amount of excipients greater than 90%. Therefore, physical manipulation is not expected to allow for the isolation of esketamine by an abuser, and an abuser would likely be required to insufflate the entire 1000 mg of powder, including 960 mg of excipients, in order to attempt to administer the 40 mg of esketamine from any given tablet.

Example 9—Heat Pretreatment

A series of pretreatments were performed on esketamine HCl tablets according to the present disclosure to evaluate whether heat results in greater API recoveries when extracted in small volumes of extraction media. Crushed 40 mg tablets of esketamine HCl of example 3 were heated in an oven at various temperatures (200° C.-300° C.) until they were visibly browned, visibly charred, or significantly charred. The time required to achieve the desired visual outcome was recorded and samples of the solution's viscosity was also measured using a Cambridge VL3000 viscometer. The samples were then transferred to labeled 20 ml scintillation vials, 20 ml of LC-MS water added and then assayed by LC-MS. The results are shown in Table 21.

TABLE 21

Results of heat pretreatment per visual endpoint

| | Visible browning | | Visible charring | | Significant charring | |
|---|---|---|---|---|---|---|
| Temperature | Heating time/m:s | % esketamine recovery | Heating time/m:s | % esketamine recovery | Heating time/m:s | % esketamine recovery |
| 200° C. | 5.00 | 9.7 | 12.00 | 1.3 | 20.00 | 0.0 |
| 250° C. | 1.40 | 23.0 | 2.00 | 12.0 | 3.40 | 7.2 |
| 290° C. | 1.30 | 21.0 | 2.10 | 7.4 | 2.32 | 0.9 |
| 300° C. | 1.20 | 19.2 | 2.00 | 9.3 | 2.20 | 0.0 |

Based on this preliminary analysis, samples of material heat treated at 250° C. were then transferred into both labeled 20 ml scintillation vials or 60 ml glass sample jars and 20 ml of either water or 0.1 N HCl added. The 20 ml solutions were extracted for 1 hour at room temperature with an agitation of 150 RPM and assayed by LC-MS. The 60 ml jars were extracted overnight and assayed by LC-MS at both 1 and 18 hours. As a comparator, extraction and LC-MS were also performed on non-heat-treated tablets. The results are shown in Table 22, below:

TABLE 22

Results of % esketamine recovery

| | | No treatment | Over pre-treatment |
|---|---|---|---|
| 1 hr extraction 20 ml vial | LC-MS water | 17.6 | 13.6 |
| | 0.1N HCl | 32.4 | 21.7 |
| 1 hr extraction 60 ml jar | LC-MS water | 57.7 | 28.6 |
| | 0.1N HCl | 57.7 | 46.2 |
| 18 hr extraction 60 ml jar | LC-MS water | 60.8 | 41.3 |
| | 0.1N HCl | 61.9 | 46.2 |

Direct comparison of verification experiments between oven-heat-treated and non-heat-treated crushed tablets showed lower average esketamine % recoveries from oven heat pre-treated extracts in all cases indicating that oven heat pre-treatment of crushed tablets likely would not enhance API recovery.

Example 10—Simulated In Vitro Nasal Diffusion/Release

A vertical diffusion cell (VDC, or Franz cell) apparatus was used to evaluate the capability of tablets to subside esketamine absorption across a membrane simulating nasal diffusion. The VDC used a 33 mm diameter 12-14 kD dialysis disc as its membrane and the analysis was performed using either 46.1 mg pure esketamine HCl powder (40 mg base equivalent), 161.42 mg/ml esketamine HCl (140 mg/ml esketamine base equivalent) in pH 4.5 citrate buffer, crushed 40 mg tablets of Example 3 or crushed 40 mg tablets of example 3 in 4 ml of pH 4.5 citrate buffer, with the experiments each performed in triplicate. With each VDC in a circulating water bath set at 37° C., phosphate buffer at a pH of 6.4 was added to fill each VDC receptor chamber, the membrane slid across its rim to seal the chamber, the donor chamber attached and the VDC sealed by a clamp. Stirring of the phosphate buffer at 600 RPM was then begun. After equilibration of the apparatus at 37° C. for a minimum of 15 minutes, the esketamine was deposited evenly, via the donor chamber, onto the membrane. Apart from the concentrated solution where 200 μl was deposited, the equivalent of 40 mg of esketamine base was deposited on each membrane. At 10, 30 and 60 minutes, 150 μl of extract was removed from the receiving chamber and replaced by phosphate buffer at a pH of 6.4. The extracted aliquots were then assayed for esketamine by LC-MS. The results of the assay are shown in Table 23, below.

TABLE 23

Percentage esketamine recovery

| | 10 minutes | 30 minutes | 60 minutes |
|---|---|---|---|
| Esketamine HCl powder | 45.1 | 75.9 | 79.2 |
| Concentrated solution | 23.3 | 51.3 | 71.8 |
| Crushed tablet | 0.7 | 1.0 | 2.0 |
| Pre-wet crushed tablet | 1.1 | 2.3 | 3.3 |

The results indicate that there is likely no significant esketamine diffusion from crushed tablets across a nasal membrane, in contrast to either pure esketamine powder or concentrated esketamine solution.

Example 11—Comparative Stability Testing

Tablet dosage forms according to the present disclosure (20 mg, 40 mg+100 mg esketamine HCl—see Tables 9, 10, 11, 14 and 15, supra) were tested for stability using HPLC at intervals of 3, 6 and 12 months under accelerated conditions (40° C./75% RH) in Brooklyn Part stability chambers. Each tablet assayed was prepared according to Example 2 using 1 part ethylcellulose in the dry mix to 2 parts in hydroalcoholic solution. As per Example 2, some of the tablets were prepared using tablets which were only wet milled (Granumill), and others using tablets which were both wet milled (Vector mixer) and then dry milled (Fitzmill).

The assay comprised the use of a Waters Symmetry $C_{18}$, 100×3.0 mm, 3.5 μm column at a temperature of 45° C. and a sample temperature of 4° C., with a mobile phase comprising 0.050% TFA in water and 0.0025% TFA in acetonitrile and UV detection rate of 215 nm.

In addition to known pharmacopeia peaks, a previously unreported peak was identified which eluted at RRT=1.29. Table 24 describes the results of the stability testing over the 12-month period for this impurity under accelerated conditions of 40° C. and 75% RH.

TABLE 24

RRT = 1.29 in comparative stability testing of esketamine HCl tablets

| | Initial | 3M | 6M | 12M |
|---|---|---|---|---|
| 20 mg tablets of Table 11 (wet milled) | ND | ND | 0.09 | — |
| 20 mg tablets of Table 11 (wet + dry milled) | ND | ND | ND | — |
| 40 mg tablets of Table 10 (wet + dry milled) | ND | ND | ND | — |
| 20 mg tablets of Table 14 (wet milled) | ND | ND | 0.14 | 0.18 |
| 100 mg tablets of Table 15 (wet milled) | ND | ND | 0.08 | — |

Example 12—Stress Testing Studies

Example 12a) Samples of esketamine HCl and various excipients were mixed and stored at 80° C./75% RH in a non-acidified diluent. After 4 days, the samples were assayed for the presence of the impurity. The results of the assay are described in Table 25.

TABLE 25

Esketamine HCl: excipient stress testing

| Sample | Total Impurities (% w/w) | % RRT = 1.3 |
|---|---|---|
| Esketamine + Placebo Tablets | 4.14 | DBNQ |
| Esketamine + Coated Polymer Granules | 5.23 | 0.079 |
| Esketamine + Silicon Dioxide | 0.12 | ND |
| Esketamine + Carbopol | 0.08 | ND |
| Esketamine + Magnesium Stearate | 0.14 | ND |
| Esketamine + MCC | 0.46 | ND |
| Esketamine + Mannitol | 1.30 | ND |
| Esketamine + Crospovidone | 1.00 | ND |
| Esketamine + Sodium Bicarbonate | 9.75 | ND |

Example 12b) Samples of esketamine HCl and various excipients were mixed and stored at 80° C./75% RH in an acidified diluent. After 7 days, the samples were assayed for the presence of the impurity. The results of the assay are described in Table 26.

TABLE 26

| Esketamine HCl: excipient stress testing | |
|---|---|
| Sample | % RRT = 1.3 |
| Esketamine + Ethyl Cellulose | ND |
| Esketamine + E100 | 0.143 |
| Esketamine + Compritol | ND |
| Esketamine + Hypermellose | ND |
| Esketamine + Uncoated Polymer Granules | ND |

Example 12c) 4, 16 and 32% coated esketamine HCl granules were prepared according to Example 2 and stored at 80° C./75% RH. After 7 days, the samples were assayed for the presence of the impurity. The results of the assay are described in Table 27.

TABLE 27

| Coated esketamine HCl granules stress testing | | |
|---|---|---|
| Esketamine HCl coating | Eudragit E100: Esketamine HCl | % RRT = 1.3 |
| 4% | 2.61 | 1.58 |
| 16% | 0.65 | 0.60 |
| 32% | 0.32 | 0.30 |

Example 13—Isolation and Identification of Impurity 1 g of esketamine and 5 g of Eudragit-E100 were dissolved together in about 70 mL of 0.1 N HCl. The sample was then heated at 90° C. for 10 days. Samples for analysis were prepared by extracting 1 mL of the degraded solution at various time points and diluting these samples with 13 mL 0.1 N HCl.

Samples extracted at both 6 and 10 days were identified by HPLC, according to the methods described in Example 11, to contain the impurity eluting at RRT=1.29.

Using preparative MPLC, the solutions were separated over several injections by an ISCO Redisep Gold, HP C18 100 g Column, with an injection of 5 mL and a flow rate of 60 mL/min, mobile phase of 0.1% FA in Water and 0.1% FA in acetonitrile, UV detection of 215 and 270 nm. The fractions containing the RRT=1.29 impurity were tracked by HPLC, combined, and concentrated by rotary evaporation to remove acetonitrile. By this initial isolate, the impurity was found to be approximately 50% pure and the concentrate (~400 mL) was stored at −20° C. for secondary concentration and isolation.

A second attempt at concentrating and isolating the impurity was performed by loading the concentrate (~400 mL) above onto a RediSep 100 g High Performance GOLD, C18 column. After loading, the desired impurity was eluted from the column using the gradient conditions previously described. The RRT=1.29 impurity fractions were again combined and concentrated by rotary evaporation using preparative MPLC using the same conditions previously described. Two fractions were found which showed the RRT=1.29 impurity, one at ~90% purity and a second at ~95% purity. Both fractions were concentrated separately by rotary evaporation to remove acetonitrile. The ~90% pure sample was stored at −20° C. while the ~95% pure sample was loaded on a 30 mg Waters HLB SPE cartridge prepared by washing it with ~10 mL of acetonitrile and ~10 mL water. The sample was washed with 2 mL of water and eluted with 2×2 mL of 60% acetonitrile. No significant amount of the RRT=1.29 impurity was detected in any solution apart from the first 60% acetonitrile elution fraction. This fraction was then frozen and lyophilized to give the final isolate of 0.12 mg and 95.7% purity. NMR analysis of the isolate identified the impurity to be 2-(2-chlorophenyl)-2-(methylamino)-6-methylidenecyclohexan-1-one.

What is claimed:

1. A method of treating depression comprising orally administering to a subject in need thereof, an immediate release tablet comprising esketamine or a pharmaceutically acceptable salt thereof, sodium bicarbonate in an amount of no more than 2.2 wt % and 2-(2-chlorophenyl)-2-(methylamino)-6-methylidenecyclohexan-1-one in an amount that is no more than 5.5 wt % after storage in accelerated conditions for at least 6 months.

2. The method of claim 1, wherein the immediate release tablet comprises between 5 and 100 mg of esketamine or a pharmaceutically acceptable salt thereof.

3. The method of claim 1, wherein the immediate release tablet comprises 40 mg base equivalent of esketamine.

4. The method of claim 1, wherein the immediate release tablet comprises between 20 mg and 100 mg of esketamine.

5. The method of claim 4, wherein prior to the administration, the immediate release tablet has been exposed to a storage period of six months;

after the storage period, the area under a peak corresponding to 2-(2-chlorophenyl)-2-(methylamino)-6-methylidenecyclohexan-1-one present in the tablet is measured by high performance liquid chromatography (HPLC); and the total amount of 2-(2-chlorophenyl)-2-(methylamino)-6-methylidenecyclohexan-1-one present in the tablet is determined to be no more than 5.5 wt. %;

wherein the peak corresponding to 2-(2-chlorophenyl)-2-(methylamino)-6-methylidenecyclohexan-1-one appears at a relative retention time of about 1.3 minutes when using C18, 100×3.0 mm, 3.5 μm HPLC column at a temperature of 45° C. and a sample temperature of 4° C., with a mobile phase comprising 0.050% trifluoroacetic acid (TFA) in water and 0.0025% TFA in acetonitrile and UV detection at 215 nm.

6. The method of claim 5, wherein the tablet is exposed to 40° C.±2° C. and 75%±5% relative humidity for the six month storage period.

7. The method of claim 5, wherein the tablet comprises 40-60 mg of esketamine.

8. The method of claim 5, wherein the tablet comprises 60 mg of esketamine.

9. The method of claim 5, wherein the 2-(2-chlorophenyl)-2-(methylamino)-6-methylidenecyclohexan-1-one is measured in an amount of no more than 0.2 wt % after the storage period.

10. The method of claim 5, wherein the 2-(2-chlorophenyl)-2-(methylamino)-6-methylidenecyclohexan-1-one is measured in a non-detectable amount after the storage period.

11. The method according to claim 1, wherein the immediate release tablet comprises sodium bicarbonate in an amount of no more than 2 wt %.

* * * * *